US012163137B2

(12) United States Patent
Booth, Jr. et al.

(10) Patent No.: US 12,163,137 B2
(45) Date of Patent: Dec. 10, 2024

(54) SOYBEAN GENE AND USE FOR MODIFYING SEED COMPOSITION

(71) Applicant: PIONEER HI-BRED INTERNATIONAL, INC., Johnston, IA (US)

(72) Inventors: John Russell Booth, Jr., Johnston, IA (US); Zhan-Bin Liu, Clive, IA (US); Cheng Lu, Newark, DE (US); Bo Shen, Johnston, IA (US)

(73) Assignee: PIONEER HI-BRED INTERNATIONAL, INC., IA (US)

( * ) Notice: Subject to any disclaimer, the term of this patent is extended or adjusted under 35 U.S.C. 154(b) by 209 days.

(21) Appl. No.: 17/293,532

(22) PCT Filed: Nov. 12, 2019

(86) PCT No.: PCT/US2019/060825

§ 371 (c)(1),
(2) Date: May 13, 2021

(87) PCT Pub. No.: WO2020/106488

PCT Pub. Date: May 28, 2020

(65) Prior Publication Data

US 2021/0403933 A1 Dec. 30, 2021

Related U.S. Application Data

(60) Provisional application No. 62/769,232, filed on Nov. 19, 2018.

(51) Int. Cl.
*C12N 15/82* (2006.01)

(52) U.S. Cl.
CPC ..... *C12N 15/8242* (2013.01); *C12N 15/8245* (2013.01); *C12N 15/8247* (2013.01); *C12N 15/8251* (2013.01)

(58) Field of Classification Search
None
See application file for complete search history.

(56) References Cited

U.S. PATENT DOCUMENTS

| | | | |
|---|---|---|---|
| 6,653,451 B1 | 11/2003 | Kerr et al. | |
| 9,035,129 B2 | 5/2015 | Bilyeu et al. | |
| 11,473,097 B2 * | 10/2022 | Miller | C12N 15/8251 |
| 2020/0131524 A1 | 4/2020 | Miller et al. | |

FOREIGN PATENT DOCUMENTS

WO 2014194190 A1 12/2014

OTHER PUBLICATIONS

Miller et al. Natural variation in expression of the HECT E3 ligase UPL3 influences seed size and crop yields in *Brassica napus* by altering regulatory gene expression. BioRxiv, May 30, 2018, pp. 1-39. (Year: 2018).*
Uniprot I1JSE2, HECT domain containing protein, Jun. 13, 2012. (Year: 2012).*
Shu et al. E3 Ubiquitin Ligases: Ubiquitous Actors in Plant Development and Abiotic Stress Responses. Plant Cell Physiol. Sep. 1, 2017;58(9):1461-1476. (Year: 2017).*
Meng et al. Genome-wide identification and evolution of HECT genes in soybean. Int. J. Mol. Sci. Apr. 16, 2015;16(4):8517-35. (Year: 2015).*
Miller, et al.; "Natrual variation in expression of the HECT E3 ligase UPL3 influences seed size and crop yields in *Brassica napus* by altering regulatory gene expression"; BioRxiv May 30, 2018 pp. 1-39.
Uniprot I1JSE2, HECT domain-containing protein; Jun. 13, 2012.
International Search Report and Written Opinion dated Mar. 19, 2020 for PCT/US2019/060825.

* cited by examiner

*Primary Examiner* — Cynthia E Collins

(57) ABSTRACT

Soybean seeds with increased protein and having a modified expression or activity of at least one or two HECT E3 ligase polypeptides are provided. Methods for modifying expression or activity of HECT E3 ligase polypeptides and polynucleotides include genome editing to modify the transcription regulatory region or sequence encoding the HECT E3 ligase polypeptides and transformation with recombinant DNA constructs to enhance or suppress expression or activity of the HECT E3 ligase polypeptides. Plants containing the modifications produce seeds with altered composition such as one or more of increased protein, decreased soluble carbohydrate, increased oleic acid, decreased saturated fats such as palmitic and stearic acids, and decreased linoleic or linolenic acid.

20 Claims, 2 Drawing Sheets

Specification includes a Sequence Listing.

SOYBEAN GENE AND USE FOR MODIFYING SEED COMPOSITION

REFERENCE TO SEQUENCE LISTING SUBMITTED ELECTRONICALLY

The official copy of the sequence listing is submitted electronically via EFS-Web as an ASCII formatted sequence listing with a file named "7839USPSP_SeqList_ST25" created on Nov. 19, 2018, and having a size of 176 kilobytes and is filed concurrently with the specification. The sequence listing contained in this ASCII formatted document is part of the specification and is herein incorporated by reference in its entirety.

BACKGROUND

Soybeans are a major agriculture commodity in many parts of the world, and are a source of useful products, such as protein and oil, for human and animal consumption. A valuable product obtained from processed soybeans is soybean meal, which contains a high proportion of protein and is primarily used as a component in animal feed. Soy meal can be further processed to produce soy protein isolates, soy flour or soy concentrates, which can be used in foods, glues and as emulsifiers and texturizers. Soybean plants which produce seeds higher in protein content or protein and oil content may contribute to a higher-value crop. It is nutritionally desirable to produce soybean oils rich in monounsaturated fatty acids with reduced linolenic acid and saturated fatty acids.

SUMMARY

Provided are soybean plants, seeds, plant parts and plant cells that have a genomic modification that decreases expression or activity of one or more HECT E3 ligase (HEL) polypeptides. The genomic modification can be a deletion, insertion or substitution of nucleotides in a genomic sequence encoding a HECT E3 ligase polypeptide comprising an amino acid sequence that is at least 95% identical to SEQ ID NO: 2 or 4 or a combination thereof, which modification suppresses activity of the ligase polypeptide, such that the plant produces seeds having at least one or at least two characteristics relative to that of a control seed not comprising the modification. The characteristics are selected from: (a) fatty acids with increased oleic acid content, (b) fatty acids with decreased linoleic acid content; (c) fatty acids with decreased linolenic acid content; (d) fatty acids with decreased stearic acid content; (e) fatty acids with decreased palmitic acid content; (f) a reduced soluble carbohydrate content, and (g) an increased protein content. The modification may comprise a deletion, insertion or substitution (such as an inversion) of nucleotides in a sequence encoding a polypeptide comprising an amino acid sequence that is at least 95% identical to SEQ ID NO: 2, SEQ ID NO: 4 or a combination thereof.

Provided are plants which have a HECT E3 ligase modification and further include a heterologous nucleic acid sequence selected from the group consisting of: a reporter gene, a selection marker, a disease resistance gene, a herbicide resistance gene, an insect resistance gene; a gene involved in carbohydrate metabolism, a gene involved in fatty acid metabolism, a gene involved in amino acid metabolism, a gene involved in plant development, a gene involved in plant growth regulation, a gene involved in yield improvement, a gene involved in drought resistance, a gene involved in increasing nutrient utilization efficiency, a gene involved in cold resistance, a gene involved in heat resistance and a gene involved in salt resistance in plants.

Methods of plant breeding are provided in which the modified plants are crossed with a second soybean plant to produce progeny seed. The progeny seed produced may comprise the modification and have increased protein or oleic content or decreased one or more soluble carbohydrates or saturated fatty acids relative to a progeny control seed not comprising the modification.

In some embodiments, methods for altering the composition of a seed of a soybean plant include the step of introducing a modification such as a deletion, insertion or substitution into a HECT E3 ligase gene in a soybean plant, which gene encodes a HECT E3 ligase polypeptide comprising an amino acid sequence that is at least 95% identical to SEQ ID NO: 2, 4, or a combination thereof. The modified plant is grown to produce a modified seed, which has at least one altered characteristics relative to that of a control seed not comprising the modification. The altered characteristics can include (a) fatty acids with increased oleic acid content, (b) fatty acids with decreased linoleic acid content; (c) fatty acids with decreased linolenic acid content; (d) fatty acids with decreased stearic acid content; (e) fatty acids with decreased palmitic acid content; (f) a reduced soluble carbohydrate content, and (g) an increased protein content.

In some embodiments, methods for altering the composition of a seed of a soybean plant include the step of introducing into a soybean plant a recombinant DNA construct comprising a heterologous polynucleotide that results in reduced expression (such as by gene silencing or RNAi) or activity (such as by modifying the structure of the expressed polypeptide) of a polypeptide comprising an amino acid sequence with at least 95% identity to SEQ ID NO: 2, SEQ ID NO: 4, or both, and regenerating a plant producing a seed having one or more altered characteristics relative to that of a control seed not comprising the modification, the characteristics selected from: (i) fatty acids with increased oleic acid content, (ii) fatty acids with decreased linoleic acid content; (iii) fatty acids with decreased linolenic acid content; (iv) fatty acids with decreased stearic acid content; (v) fatty acids with decreased palmitic acid content; (vi) a reduced soluble carbohydrate content, and (vii) an increased protein content. Provided are plants, seeds, plant parts and plant cells produced by the method with seeds having one or more altered characteristic.

In some embodiments, guide RNA sequences and recombinant constructs expressing the guide RNA sequences are provided that target a genomic locus of a plant cell which includes a polynucleotide that encodes a polypeptide comprising an amino acid sequence that is at least 90% identical to SEQ ID NO: 2 or 4.

Provided are soybean plant cells, plants, seeds and plant parts comprising a guide RNA sequence that targets a genomic locus of a plant cell, which includes a polynucleotide that encodes a polypeptide comprising an amino acid sequence that is at least 90% identical to SEQ ID NO: 2 or 4, wherein the soybean plant cell can be regenerated into a plant producing seeds having an altered characteristic compared to control seeds not comprising the guide RNA sequence.

In some embodiments, methods of advancing a soybean plant in a plant breeding program are provided, wherein the plant contains a modified polynucleotide comprising a modification in SEQ ID NO: 5 or 9: A DNA sample obtained from the soybean plant comprising the modified polynucleotide is contacted with a first and a second primer molecule, which bind upstream of or including the modification in SEQ ID NO: 5 or 9 and downstream of or including the modification in SEQ ID NO: 5 or 9 respectively. A nucleic acid amplification reaction condition is performed to produce a DNA amplicon molecule indicating the presence of the modified polynucleotide which is detected to advance the plant in the plant breeding program. The soybean plant can be selfed or crossed with a second plant in the breeding program to produce progeny seed. The plant or progeny plants comprising the modified polynucleotide produce seed having one or more altered characteristic relative to that of a control seed produced from a control plant not comprising the modified polynucleotide. The characteristic is selected from at least one of: (a) fatty acids with increased oleic acid content, (b) fatty acids with decreased linoleic acid content; (c) fatty acids with decreased linolenic acid content; (d) fatty acids with decreased stearic acid content; (e) fatty acids with decreased palmitic acid content; (f) a reduced soluble carbohydrate content, and (g) an increased protein content.

BRIEF DESCRIPTION OF THE SEQUENCES

TABLE 1

Figure 1:
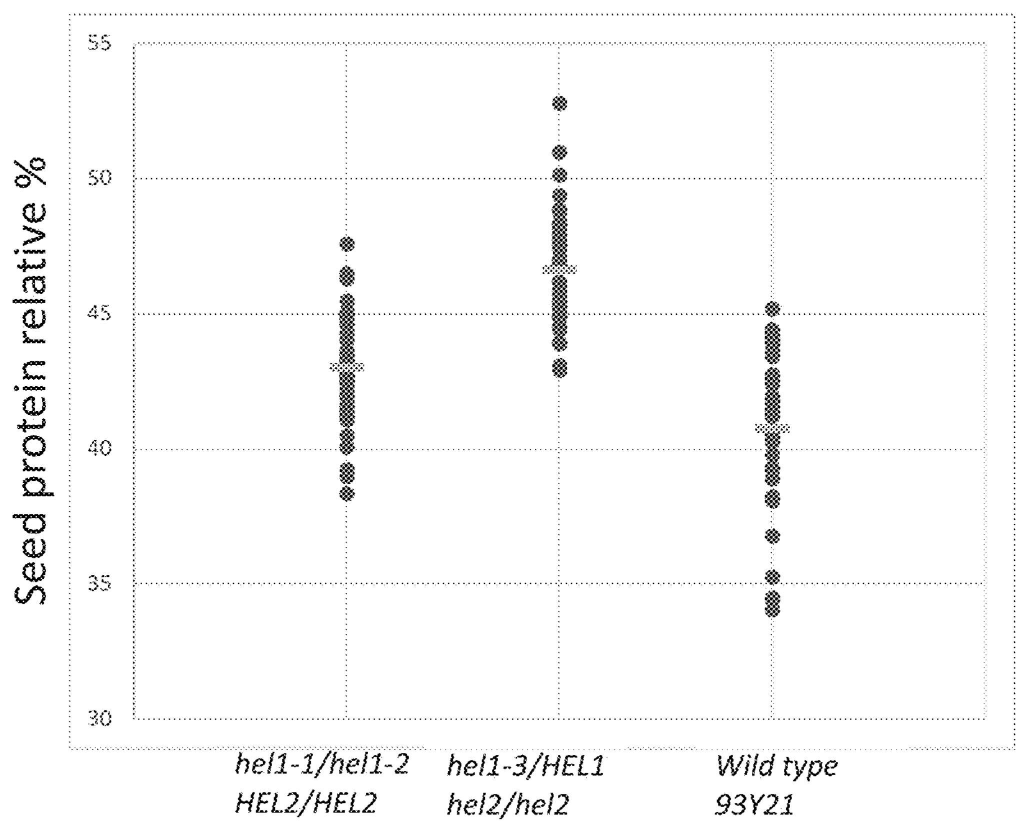
FIG. 1 is a graph showing the T1 seed protein content of hel1 and hel2 knockout variants. hel1-1/hel1-2 is homozygous knockout of HEL1 gene; HEL2/HEL2 is wild type of HEL2 gene; hel1-3/HEL1 is heterozygous knockout of HEL1 gene; hel2/hel2 is homozygous knockout of HEL2 gene. Each dot represents an individual T1 seed. The bar is the average seed protein content; values are given as relative percent protein estimates from NIR analysis.

Listing of sequences used in this application

| Sequence Description | SEQ ID NO: |
|---|---|
| HEL1 HECT E3 ligase polynucleotide coding sequence (chromosome 4) | 1 |
| HEL1 HECT E3 ligase polypeptide | 2 |
| HEL2 HECT E3 ligase polynucleotide coding sequence (chromosome 6) | 3 |
| HEL2 HECT E3 ligase polypeptide | 4 |
| HEL1 genomic polynucleotide (chromosome 4) | 5 |
| hel1-1 genomic polynucleotide (+G) | 6 |
| hel1-2 genomic polynucleotide (−AGGT) | 7 |
| hel1-3 genomic polynucleotide (−G) | 8 |
| HEL2 genomic polynucleotide (chromosome 6) | 9 |
| hel2 genomic | 10 |
| GM-HEL-CR1 | 11 |
| GM-HEL-CR5 | 12 |
| GM-HEL-CR6 | 13 |
| GM-HEL-CR7 | 14 |
| GM-HEL-CR8 | 15 |
| GM-DGAT1b mod | 16 |

DETAILED DESCRIPTION

Compositions and methods related to modified plants producing seeds having one or more altered characteristics, such as increased protein, reduced soluble carbohydrate or altered fatty acids, such as increased oleic acid, are provided. Plants that have been modified using genomic editing techniques, transformation or mutagenesis to produce seeds having the altered characteristic are provided. Suitable plants include oil-seed plants, such as palm, canola, sunflower and soybean as well as, without limitation, rice, cotton, sorghum, wheat, maize, alfalfa and barley. Modifying expression or activity of a HECT E3 ligase polypeptide in a plant such as soybean or modifying the coding sequence of the HECT E3 ligase polypeptide, results in a seed with high-seed protein relative to a comparable seed not comprising the modification. The modification can be introduced using genomic editing technology, transformation or mutagenesis, such as described herein. Plants, such as soybean plants, that show reduced expression or activity of at least one or two HECT E3 ligase polypeptides, and which are robust, high-yielding and produce seeds containing an altered characteristic such as increased protein or oleic acid are provided. In some embodiments, the modified plant with reduced HECT E3 ligase polypeptide expression or activity further comprises a modification to a sequence relating to oil accumulation, resulting in seeds having increased oil content relative to seeds of a control plant not comprising the modification. Such a modified sequence may be polynucleotide encoding a diglyceride acyltransferase (DGAT), such as shown in SEQ ID NO: 16, which has 14 amino acid substitutions compared to the soy wild-type DGAT sequence, or a sequence having a percent identity to such sequence as described herein.

Unless specified otherwise, protein, oil, PROIL, fiber, stachyose, sucrosyl-oligosaccharide, soluble carbohydrate, and other components are measured by weight at or adjusted to a 13% moisture basis in the soybean seed. Fatty acid components such as oleic acid, linoleic acid, linolenic acid, stearic acid, palmitic acid, total saturated fatty acids are expressed as a proportion of the total fatty acids. Alterations in fatty acid components compared with a control are expressed by comparing the proportion of the fatty acid in the total fatty acids of the modified seed compared with the proportion of the fatty acid in total fatty acids of a control seed. For example, a 20% oleic acid content in the control seed and a 40% oleic acid content in the modified seed would represent an increase of 20 percentage points in oleic acid in the modified seed or a 100% increase in oleic acid relative to the control. Seeds, plants (or plant parts thereof) producing seeds, and methods of making or using the seeds and plants (or plant parts thereof) and having the seed compositions described herein are provided.

The plants comprising the modification produce seeds which are of substantially similar size, substantially similar weight or both substantially similar size and weight to control seeds produced by plants not comprising the modification. For example, the seeds comprising the modification may not differ in size and/or weight from control seeds not comprising the modification using a Student's t-test at the 5%, 2% or 1% significance level. The seeds may differ by less than 5%, 4%, 3%, 2%, or 1% in size, weight or both size and weight harvested at maturity and adjusted to a 13% moisture basis.

Provided are soybean seeds (and plants producing the seeds) comprising a modification and having a protein content increase in the seed of at least 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, or 2.0 and less than 3.0, 2.9, 2.8, 2.7, 2.6, 2.5, 2.4, 2.3, 2.2, 2.1, 2.0, 1.9, 1.8, 1.7, 1.6, or 1.5 percentage points by weight compared with an unmodified, control, null or wild-type soybean seed (and plant producing the seed) not comprising the modification. Provided are soybean seeds having a protein content of at least 30.0%, 30.5%, 31.0%, 31.5%, 32.0%, 32.5%, 33.0%, 33.5%, 34.0%, 34.5%, 35.0%, 35.5%, 36.0%, 36.5%, 37.0%, 37.5%, 38.0%, 38.5%, 39.0%, 39.5%, 40.0%, 40.5%, 41.0%, 41.5% or 42.0% (percentage points by weight) and less than 55%, 54%, 53%, 52%, 51%, 50%, 49%, 48%, 47%, 46%, 45% or 44% (percentage points by weight).

Provided are modified soybean seeds and plants producing such seeds, as described herein, containing a substantially similar or increased oil content compared with a comparable unmodified, control, null or wild-type seed. The oil content of the modified seed may be at least or at least about 15%, 16%, 17%, 18%, 19%, 19.5%, 20%, 20.5%, 21%, 21.5%, 22%, 22.5%, 23%, 23.5%, 24%, 24.5%, or 25% oil and less than or less than about 32%, 31%, 30%, 29%, 28%, 27%, 26%, 25%, 24.5%, 24%, 23.5%, 23%, 22.5%, 22%, 21.5%, 21%, 20.5% or 20% oil. The modified soybean seed may contain an oil content that is at least 70%, 75%, 80%, 85%, 90%, 95%, 100%, 105%, 110%, 115% or 120% and less than 150%, 140%, 130%, 120% or 110% or the amount of oil in a comparable unmodified, control, null or wild-type seed.

Provided are modified soybean seeds and plants producing such seeds, as described herein, containing an increased amount of protein plus oil relative to a control, comparable unmodified or null seed or plant producing such seed. For the sum of oil and protein content, also referred to as the PROIL content, the modified soybean seed such as described herein may contain at least or at least about 54%, 55%, 56%, 57%, 58%, 59%, 60%, 61%, 62% or 63% PROIL and less than or less than about 70%, 65%, 60%, 59%, 58%, 57%, 56%, or 55% PROIL by weight compared with the comparable unmodified or null soybean containing at least or at least about 45%, 46%, 47%, 48%, 49%, 50%, 51%, 52% or 53% PROIL and less than or less than about 56%, 55%, 54%, 53%, 52%, 51%, 50%, or 49% PROIL. Useful examples of percent point increases in PROIL in a seed, such as a modified soybean seed described herein, compared with a comparable null unmodified or control soybean include, but are not limited to, percentage point increases by weight of at least or at least about 1, 2, 3, 4, or 5% and less than or less than about 15, 14, 13, 12, 11, 10, 9, 8, 7, or 6%.

Provided are seeds and plants producing seed comprising a modification and having an amount of soluble carbohydrate of about or at least about 0.1%, 0.2%, 0.3%, 0.4%, 0.5%, 0.6%, 0.7%, 0.8%, 0.9%, 1.0%, 1.1%, 1.2%, 1.3%, 1.4%, 1.5%, 1.6%, 1.7%, 1.8%, 1.9%, 2.0%, 2.5, 3.0, 3.5 or 4.0 and less than about 15.0%, 14.0%, 13.0%, 12.0%, 11.0%, 10.0%, 9.0%, 8.0%, 7.5%, 7.0%, 6.5%, 6.0%, 5.5%, 5.0%, 4.5%, 4.4%, 4.3%, 4.2%, 4.1%, 4.0%, 3.9%, 3.8%, 3.7%, 3.6%, 3.5%, 3.4%, 3.3%, 3.2%, 3.1%, 3.0%, 2.9%, 2.8%, 2.7%, 2.6%, 2.5%, 2.4%, 2.3%, 2.2%, 2.1% or 2.0% soluble carbohydrate (percentage points by weight). The soluble carbohydrate may be reduced by at least 50%, 40%, 30%, 20%, 15%, 10%, 9%, 8%, 7%, 6%, 5%, 4%, 3%, 2% or 1% in the modified seed compared with a control seed not comprising the modification.

Provided are seeds and plants producing seed comprising a modification and having an amount of stachyose of about or at least about 0.1%, 0.2%, 0.3%, 0.4%, 0.5%, 0.6%, 0.7%, 0.8%, 0.9%, 1.0%, 1.1%, 1.2%, 1.3%, 1.4%, 1.5%, 1.6%, 1.7%, 1.8%, 1.9% or 2.0% and less than about 4.5%, 4.4%, 4.3%, 4.2%, 4.1%, 4.0%, 3.9%, 3.8%, 3.7%, 3.6%, 3.5%, 3.4%, 3.3%, 3.2%, 3.1%, 3.0%, 2.9%, 2.8%, 2.7%, 2.6%, 2.5%, 2.4%, 2.3%, 2.2%, 2.1% or 2.0% stachyose (percentage points by weight). The stachyose may be reduced by at least 50%, 40%, 30%, 20%, 15%, 10%, 9%, 8%, 7%, 6%, 5%, 4%, 3%, 2% or 1% in the modified seed compared with a control seed not comprising the modification.

Provided are seeds and plants producing seed comprising a modification and having an amount of sucrose of about or at least about 0.1%, 0.2%, 0.3%, 0.4%, 0.5%, 0.6%, 0.7%, 0.8%, 0.9%, 1.0%, 1.1%, 1.2%, 1.3%, 1.4%, 1.5%, 1.6%, 1.7%, 1.8%, 1.9%, 2.0%, 2.5%, 3.0%, 3.5%, 4.0%, 4.5% or 5.0% and less than about 12%, 11%, 10%, 9.5%, 9.0%, 8.0%, 7.0%, 6.0%, 5.0%, 4.5%, 4.4%, 4.3%, 4.2%, 4.1%, 4.0%, 3.9%, 3.8%, 3.7%, 3.6%, 3.5%, 3.4%, 3.3%, 3.2%, 3.1%, 3.0%, 2.9%, 2.8%, 2.7%, 2.6%, 2.5%, 2.4%, 2.3%, 2.2%, 2.1% or 2.0% sucrose (percentage points by weight). The sucrose may be reduced by at least 50%, 40%, 30%, 20%, 15%, 10%, 9%, 8%, 7%, 6%, 5%, 4%, 3%, 2% or 1% in the modified seed compared with a control seed not comprising the modification.

Provided are seeds and plants producing seed comprising a modification and having an amount of sucrosyl-oligosaccharide of about or at least about 0.5%, 1.0%, 1.1%, 1.2%, 1.3%, 1.4%, 1.5%, 1.6%, 1.7%, 1.8%, 1.9%, 2.0%, 2.1%, 2.2%, 2.3%, 2.4%, 2.5%, 2.6%, 2.7%, 2.8%, 2.9% or 3.0% and less than about 5.5%, 5.0%, 4.9%, 4.8%, 4.7%, 4.6%, 4.5%, 4.4%, 4.3%, 4.2%, 4.1%, 4.0%, 3.9%, 3.8%, 3.7%, 3.6%, 3.5%, 3.4%, 3.3%, 3.2%, 3.1%, 3.0%, 2.9%, 2.8%, 2.7%, 2.6%, or 2.5% sucrosyl-oligosaccharide (percentage points by weight). The sucrosyl-oligosaccharide may be reduced by at least 50%, 40%, 30%, 20%, 15%, 105, 9%, 8%, 7%, 6%, 5%, 4%, 3%, 2% or 1% in the modified seed compared with a control seed not comprising the modification.

Provided are soybean seeds comprising a modification having a fiber content decrease in the seed of at least 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, or 4.0 percentage points by weight and less than 8.0, 7.9, 7.8, 7.7, 7.6, 7.5, 7.4, 7.3, 7.2, 7.1, 7.0, 6.9, 1.8, 6.7, 6.6, 6.5, 6.4, 6.3, 6.2, 6.1, 6.0, 5.9, 5.8, 5.7, 5.6, 5.5, 5.4, 5.3, 5.2, 5.1 or 5.0 percentage points by weight compared with a control plant not comprising the modification. Provided are soybean seeds having a fiber content in the seeds of less than 8.0, 7.5, 7.0, 6.5, 6.0, 5.9, 5.8, 5.7, 5.6, 5.5, 5.4, 5.3, 5.2, 5.1, 5.0, 4.9, 4.8, 4.7, 4.6, 4.5, 4.4, 4.3, 4.2, 4.1, 4.0, 3.9, 3.8, 3.7, 3.6, 3.5, 3.4, 3.3, 3.2, 3.1 or 3.0% (percentage points by weight) and at least 1.0, 1.5, 2.0, 2.5 or 3.0% (percentage points by weight).

The soybean seeds can be efficiently processed to produce meal (either high-protein meal produced from dehulled beans or conventional meal produced from whole soybeans) having a high protein content compared with comparable meal produced from comparable seeds that do not contain the modification. In some embodiments, meal is provided which has a protein content that is increased by at least 0.5, 1.0, 1.5, 2.0, 2.5, 3.0, 3.5, 4.0, 4.5 or 5.0% percent by weight and less than 12.0, 11.0, 10.0, 9.0, 8.0, 7.0, 6.0 or 5.0% by weight compared to meal prepared from a control soybean seed not comprising the modification, such as a null, unmodified or wild-type soybean seed. The meal may be prepared from a plant comprising the modification and may comprise a modified polynucleotide described herein.

Provided are seeds, such as soybean seeds, which can be processed to produce oils, and the oils produced therefrom, which contain any combination of oleic acid, linolenic acid, linoleic acid, erucic acid (C:22:1) and saturated fatty acids such as stearic acid and palmitic acid in the amounts disclosed herein. Other saturated fatty acids in the soybean seeds and oils which may be increased or decreased compared with a control plant, seed or oil include myristic acid (C:14:0), and long chain saturated fatty acids arachidic acid (C20:0), behenic acid (C22:0) and lignoceric acid (C24:0).

Provided are seeds, such as soybean seeds, which can be processed to produce oils, and the oils produced therefrom, which have at least or at least about 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85 percent oleic (C 18:1) acid of the total fatty acids by weight and less than or less than about 95, 94, 93, 92, 91, 90, 89, 88, 87, 86, 85, 84, 83, 82, 81, 80, 79, 78, 76, 75, 74, 73, 72, 71, 70, 65, 60, 55, 50, 45, 40, 35 or 30% percent oleic acid of the total fatty acids by weight. The oleic acid content may be increased by at least about 1, 2, 3, 4, 5, 6, 7, 8, 9, 10, 15, 20, 25, 30, 40, 50, 60, 70, 80, 90, 100, 125, 150, 175, 200, 225, 250, 275 or 300 percent relative to a control plant not comprising the modification. A 100% increase is a two-fold increase in the oleic acid content expressed as a percentage of the total fatty acids.

Provided are seeds, such as soybean seeds, which can be processed to produce oils, and the oils produced therefrom, which have at least or at least about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, or 3.0 percent linolenic (C 18:3) acid of the total fatty acids by weight and less than or less than about 8, 7.5, 7.0, 6.5, 6, 5.5, 5, 4.5, 4, 3.9, 3.8, 3.7, 3.6, 3.5, 3.4, 3.3, 3.2, 3.1, 3.0, 2.9, 2.8, 2.7, 2.6, 2.5, 2.4, 2.3, 2.2, 2.1 or 2.0 percent linolenic acid of the total fatty acids by weight. The linolenic acid content may be decreased by at least about 1, 2, 3, 4, 5, 6, 7, 8, 9, 10, 15, 20, 25, 30, 40, 50, 60, 70, 80, 90 or 95 percent relative to a control plant not comprising the modification. A 50% decrease is a halving of the linolenic acid content expressed as a percentage of the total fatty acids.

Provided are soybean seeds which can be processed to produce oils, and the oils produced therefrom, which have at least or at least about 1, 2, 3, 4, 5, 6, 7, 8, 9, 10, 11, 12, 13, 14, or 15 percent linoleic (C 18:2) acid of the total fatty acids by weight and less than or less than about 60, 55, 50, 45, 40, 35, 30, 25, 20, 15, 10, 9, 8, 7, 6, 5, 4, or 3 percent linoleic acid of the total fatty acids by weight. The linoleic acid content may be decreased by at least about 1, 2, 3, 4, 5, 6, 7, 8, 9, 10, 15, 20, 25, 30, 40, 50, 60, 70, 80, 90 or 95 percent relative to a control plant not comprising the modification. A 50% decrease is a halving of the linoleic acid content expressed as a percentage of the total fatty acids.

Provided are seeds, such as soybean seeds, which can be processed to produce oils, and the oils produced therefrom, which have at least or at least about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, or 3.0 percent stearic acid (C 18:0) of the total fatty acids by weight and less than or less than about 8.0, 7.5, 7.0, 6.5, 6.0, 5.5, 5, 4.5, 4, 3.9, 3.8, 3.7, 3.6, 3.5, 3.4, 3.3, 3.2, 3.1, 3.0, 2.9, 2.8, 2.7, 2.6, 2.5, 2.4, 2.3, 2.2, 2.1 or 2.0 percent stearic acid of the total fatty acids by weight. The stearic acid content may be decreased by at least about 1, 2, 3, 4, 5, 6, 7, 8, 9, 10, 15, 20, 25, 30, 40, 50, 60, 70, 80, 90 or 95 percent relative to a control plant not comprising the modification. A 50% decrease is a halving of the stearic acid content expressed as a percentage of the total fatty acids.

Provided are seeds, such as soybean seeds, which can be processed to produce oils, and the oils produced therefrom, which have at least or at least about 0.1, 0.5, 1.0, 1.5, 2.0, 2.5, 3.0, 3.5, 4.0, 4.5, 5.0, 5.5, 6.0, 6.5 or 7.0 percent palmitic acid (C 16:0) of the total fatty acids by weight and less than or less than about 15, 14, 13, 12, 11.5, 11.0, 10.5, 10.0, 9.5, 9.0, 8.5, 8.0, 7.5, 7.0, 6.5, 6.0, 5.5, 5.0, 4.5, 4.0, 3.5, 3.0, 2.5, 2.0, 1.5, or 1.0 percent palmitic acid of the total fatty acids by weight. The palmitic acid content may be decreased by at least about 1, 2, 3, 4, 5, 6, 7, 8, 9, 10, 15, 20, 25, 30, 40, 50, 60, 70, 80, 90 or 95 percent relative to a control plant not comprising the modification. A 50% decrease is a halving of the palmitic acid content expressed as a percentage of the total fatty acids Provided are seeds, such as soybean seeds, which can be processed to produce oils, and the oils produced therefrom, which have at least or at least about 0.1, 0.5, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10.0, 10.5, 11.0, 11.5 or 12 percent total saturated fatty acids of the total fatty acids by weight and less than or less than about 18, 17.5, 17, 16.5, 16, 15.5, 15, 14.5, 14, 13.5, 13.0, 12.5, 12.0, 11.5, 11.0, 10.5, 10.0, 9.5, 9.0, 8.5, 8.0, 7.5, 7.0, 6.5, 6.0, 5.5, 5.0, 4.5, 4.0, 3.5, 3.0, 2.5 or 2.0 percent total saturated fatty acids of the total fatty acids by weight. The total saturated fatty acid content may be decreased by at least about 1, 2, 3, 4, 5, 6, 7, 8, 9, 10, 15, 20, 25, 30, 40, 50, 60, 70, 80, 90 or 95 percent relative to a control plant not comprising the modification. A 50% decrease is a halving of the total saturated fatty acid content expressed as a percentage of the total fatty acids Provided are modified soybean seeds and plants, plant parts and plant cells which have an increased protein or PROIL content and at least a comparable or increased yield, such as described herein, relative to a comparable control unmodified seed and plant, plant part or plant cell not comprising the modification.

The modified polypeptides and polynucleotides described herein include or encode at least one or at least two HECT E3 ligase polypeptides, or a combination thereof. HECT E3 ligase polypeptides are E3 ubiquitin ligases. The ubiquitin proteasome system is involved the regulation of nearly every aspect plant growth and development by controlling protein degradation. Protein ubiquitination may occur by covalent attachment of ubiquitin to the target protein by three ligases, E1, E2, and E3. E3 ubiquitin ligases can be classified into 3 groups, HECT E3 ligase, RING-type E3 ligase, and U-box type E3 ligase. HECT E3 ligase (HEL) contains a HECT domain, which is a 350-amino acid motif at the C-terminus. The soybean genome contains 19 putative HECT E3 ligase genes with unknown functions (Meng et al., Genome-wide identification and evolution of HECT genes in soybean. Int J Mol Sci. 2015 Apr. 16; 16(4):8517-35).

Unless expressly stated to the contrary, "soybean" means a soybean plant or seed of *Glycine max*. Provided are soybean plants, plant cell, plant parts and seeds which have had expression of a polypeptide or polynucleotide sequence that encodes the polypeptide suppressed, knocked out, decreased or inhibited and/or in which the activity of the polypeptide is altered. Examples of polypeptides include the HECT E3 ligase polypeptide shown in SEQ ID NO: 2, encoded by SEQ ID NO: 1 and the HECT E3 ligase polypeptide shown in SEQ ID NO: 4, encoded by the SEQ ID NO: 3. In some embodiments, soybean plants, seeds, plant cells and methods are provided in which expression or activity of both the HECT E3 ligase polypeptides are reduced or suppressed.

In some embodiments, the modification results in the suppression of the native HECT E3 ligase polypeptide shown in SEQ ID NO: 2, which is encoded by SEQ ID NO:1, or the HECT E3 ligase polypeptide shown in SEQ ID NO: 4, which is encoded by SEQ ID NO: 3, or both polypeptides. The genome is modified to knock-out, silence, reduce or suppress expression or activity of the native HEL1 or HEL2 polypeptide, or both, such as by disrupting the reading frame through insertion or deletion of one or more single bases or short or long sequences, introducing a sufficient number of SNPs to disrupt function or by modifying a transcription regulatory sequence in the transcription regulatory region to include for example repressor elements, repressor binding elements or disrupted promotor enhancer elements to reduce or prevent expression of the HEL1 or HEL2 polypeptide, or both. In some embodiments, the expression level of the polynucleotide or polypeptide or activity of a polypeptide in a tissue or organ of interest, such as the seed, seed endosperm, embryo, leaf, root or stalk, is less than 95, 90, 85, 80, 75, 70, 65, 60, 55, 50, 45, 40, 35, 30, 25, 20, 15, 10, 5, 4, 3, 2, or 1% of the expression level of the polynucleotide or polypeptide or activity of the polypeptide in a comparable control, unmodified or null tissue or organ of interest. Plants producing seeds with increased protein as described herein are obtained.

In some embodiments, the soybean plant, plant cell, plant part or seed includes or expresses the sequences shown in SEQ ID NOs: 6, 7, 8 or 10. The soybean plant, plant cell, plant part or seed may include an insertion, deletion, substation or modification in these sequences. Examples of modifications included an insertion, such as a G or other insertion at the position corresponding to 4857 of SEQ ID NO: 6, a deletion, such as the deletion of AGGT at position 4854 to 7857 of SEQ ID NO: 5, shown in SEQ ID NO: 7, a deletion of G at position 4856 of SEQ ID NO: 5, shown in SEQ ID NO: 8, or an inversion of a sequence, such as corresponding to positions 1899 to 2799 of SEQ ID NO: 10, or any combination thereof, or sequences sharing a percent identity with such sequences.

In some embodiments, the soybean plant, plant cell, plant part or seed includes a recombinant DNA construct or molecule or suppression construct described herein which suppresses or reduces expression or activity of the polypeptide. Transformation methods for producing such soybean plants, plant cells, plant parts or seeds are provided.

In some embodiments, the soybean plant further includes a heterologous nucleic acid sequence selected from the group consisting of: a reporter gene, a selection marker, a disease resistance gene, a herbicide resistance gene, an insect resistance gene; a gene involved in carbohydrate metabolism, a gene involved in fatty acid metabolism, a gene involved in amino acid metabolism, a gene involved in plant development, a gene involved in plant growth regulation, a gene involved in yield improvement, a gene involved in drought resistance, a gene involved in increasing nutrient utilization efficiency, a gene involved in cold resistance, a gene involved in heat resistance and a gene involved in salt resistance in plants. The heterologous nucleic acid may be introduced by backcrossing or transformation.

Provided are polynucleotides that have at least about or at least 40%, 45%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater sequence identity compared to a reference nucleotide sequence, such as a nucleotide sequence disclosed in the sequence listing herein, using one of the alignment programs described herein using standard parameters, as well as nucleotide substitutions, deletions, insertions, fragments thereof, and combinations thereof.

An "isolated polynucleotide" generally refers to a polymer of ribonucleotides (RNA) or deoxyribonucleotides (DNA) that is single- or double-stranded, optionally containing synthetic, non-natural or altered nucleotide bases, that is no longer in its natural environment and have been placed in a difference environment by the hand of man, for example in vitro. An isolated polynucleotide in the form of DNA may be comprised of one or more segments of cDNA, genomic DNA or synthetic DNA.

A "recombinant" nucleic acid molecule (or DNA) is used herein to refer to a nucleic acid sequence (or DNA) that is in a recombinant plant host cell. In some embodiments, an "isolated" or "recombinant" nucleic acid is free of sequences (preferably protein encoding sequences) that naturally flank the nucleic acid (i.e., sequences located at the 5' and 3' ends of the nucleic acid) in the genomic DNA of the organism from which the nucleic acid is derived.

The terms "polynucleotide", "polynucleotide sequence", "nucleic acid sequence", "nucleic acid fragment", and "isolated nucleic acid fragment" are used interchangeably herein. These terms encompass nucleotide sequences and the like. A polynucleotide may be a polymer of RNA or DNA that is single- or double-stranded, that optionally contains synthetic, non-natural or altered nucleotide bases. A polynucleotide in the form of a polymer of DNA may be comprised of one or more segments of cDNA, genomic DNA, synthetic DNA, or mixtures thereof. Nucleotides (usually found in their 5'-monophosphate form) are referred to by a single letter designation as follows: "A" for adenylate or deoxyadenylate (for RNA or DNA, respectively), "C" for cytidylate or deoxycytidylate, "G" for guanylate or deoxyguanylate, "U" for uridylate, "T" for deoxythymidylate, "R" for purines (A or G), "Y" for pyrimidines (C or T), "K" for G or T, "H" for A or C or T, "I" for inosine, and "N" for any nucleotide.

A transcription regulatory element or sequence, or a regulatory element or sequence generally refers to a transcriptional regulatory element involved in regulating the transcription of a nucleic acid molecule such as a gene or a target gene. The regulatory element is a nucleic acid and may include a promoter, an enhancer, an intron, a 5'-untranslated region (5'-UTR, also known as a leader sequence), or a 3'-UTR or a combination thereof. A regulatory element may act in "cis" or "trans", and generally it acts in "cis", i.e. it activates expression of genes located on the same nucleic acid molecule, e.g. a chromosome, where the regulatory element is located. The nucleic acid molecule regulated by a regulatory element does not necessarily have to encode a functional peptide or polypeptide, e.g., the regulatory element can modulate the expression of a short interfering RNA or an anti-sense RNA.

In some embodiments, the modified polynucleotide includes a modified transcriptional enhancer sequence. An enhancer element is any nucleic acid molecule that increases transcription of a nucleic acid molecule when functionally linked to a promoter regardless of its relative position. An enhancer may be an innate element of the promoter or a heterologous element inserted to enhance the amount of promotor activity or tissue-specificity of a promoter.

Various enhancers may be used including introns with gene expression enhancing properties in plants (US Patent Application Publication Number 2009/0144863), the ubiquitin intron (i.e., the maize ubiquitin intron 1 (see, for example, NCBI sequence S94464)), the omega enhancer or the omega prime enhancer (Gallie, et al., (1989) Molecular Biology of RNA ed. Cech (Liss, New York) 237-256 and Gallie, et al., (1987) Gene 60:217-25), the CaMV 35S enhancer (see, e.g., Benfey, et al., (1990) EMBO J. 9:1685-96) and the enhancers of U.S. Pat. No. 7,803,992 may also be used, each of which is incorporated by reference. The above list of transcriptional enhancers is not meant to be limiting. Any appropriate transcriptional enhancer can be used in the embodiments.

A repressor (also sometimes called herein silencer, repressor element, or repressor binding element) is defined as any nucleic acid molecule which inhibits the transcription when functionally linked to a promoter regardless of relative position.

"Promoter" generally refers to a nucleic acid fragment capable of controlling transcription of another nucleic acid fragment. A promoter generally includes a core promoter (also known as minimal promoter) sequence that includes a minimal regulatory region to initiate transcription, that is a transcription start site. Generally, a core promoter includes a TATA box and a GC rich region associated with a CAAT box or a CCAAT box. These elements act to bind RNA polymerase II to the promoter and assist the polymerase in locating the RNA initiation site. Some promoters may not have a TATA box or CAAT box or a CCAAT box, but instead may contain an initiator element for the transcription initiation site. A core promoter is a minimal sequence required to direct transcription initiation and generally may not include enhancers or other UTRs. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. Core promoters are often modified to produce artificial, chimeric, or hybrid promoters, and can further be used in combination with other regulatory elements, such as cis-elements, 5'UTRs, enhancers, or introns, that are either heterologous to an active core promoter or combined with its own partial or complete regulatory elements.

The term "cis-element" generally refers to transcriptional regulatory element that affects or modulates expression of an operably linked transcribable polynucleotide, where the transcribable polynucleotide is present in the same DNA sequence. A cis-element may function to bind transcription factors, which are trans-acting polypeptides that regulate transcription.

The termination region may be native with the transcriptional initiation region, may be native with the operably linked DNA sequence of interest, may be native with the plant host or may be derived from another source (i.e., foreign or heterologous to the promoter, the sequence of interest, the plant or any combination thereof).

The sequences include one or more contiguous nucleotides "Contiguous nucleotides" is used herein to refer to nucleotide residues that are immediately adjacent to one another.

As used herein non-genomic nucleic acid sequence, nucleic acid molecule or polynucleotide refers to a nucleic acid molecule that has one or more changes in the nucleic acid sequence compared to a native or genomic nucleic acid sequence. In some embodiments, the change to a native or genomic nucleic acid molecule includes but is not limited to: changes in the nucleic acid sequence due to the degeneracy of the genetic code; optimization of the nucleic acid sequence for expression in plants; changes in the nucleic acid sequence to introduce at least one amino acid substitution, insertion, deletion and/or addition compared to the native or genomic sequence; deletion of one or more upstream or downstream regulatory regions associated with the genomic nucleic acid sequence; insertion of one or more heterologous upstream or downstream regulatory regions; deletion of the 5' and/or 3' untranslated region associated with the genomic nucleic acid sequence; insertion of a heterologous 5' and/or 3' untranslated region; and modification of a polyadenylation site. In some embodiments, the non-genomic nucleic acid molecule is a synthetic nucleic acid sequence.

Provided are polypeptides having at least about or at least 40%, 45%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater sequence identity compared to polypeptides referenced in the sequence listing, as well as amino acid substitutions, deletions, insertions, fragments thereof, and combinations thereof. The term "about" when used herein in context with percent sequence identity means+/−0.5%. These values can be appropriately adjusted to determine corresponding homology of proteins considering amino acid similarity and the like.

In some embodiments, the sequence identity is against the full-length sequence of a polypeptide disclosed in the sequence listing. In some embodiments, the polypeptide retains activity or shows enhanced or reduced activity As used herein, the term "protein," "peptide molecule," or "polypeptide" includes those molecules that undergo modification, including post-translational modifications, such as, but not limited to, disulfide bond formation, glycosylation, phosphorylation or oligomerization.

The terms "amino acid" and "amino acids" refer to all naturally occurring L-amino acids.

Variants may be made by making random mutations or the variants may be designed. In the case of designed mutants, there is a high probability of generating variants with similar activity to the native polypeptide when amino acid identity is maintained in critical regions of the polypeptide which account for biological activity or are involved in the determination of three-dimensional configuration which ultimately is responsible for the biological activity. A high probability of retaining activity will also occur if substitutions are conservative. Amino acids may be placed in the following classes: non-polar, uncharged polar, basic, and acidic. Conservative substitutions whereby an amino acid of one class is replaced with another amino acid of the same type are least likely to materially alter the biological activity of the variant. Table 2 provides a listing of examples of amino acids belonging to each class.

TABLE 2

Classes of amino acids

| Class of Amino Acid | Examples of Amino Acids |
|---|---|
| Nonpolar Side Chains | Ala (A), Val (V), Leu (L), Ile (I), Pro (P), Met (M), Phe (F), Trp (W) |
| Uncharged Polar Side Chains | Gly (G), Ser (S), Thr (T), Cys (C), Tyr (Y), Asn (N), Gln (Q) |
| Acidic Side Chains | Asp (D), Glu (E) |
| Basic Side Chains | Lys (K), Arg (R), His (H) |
| Beta-branched Side Chains | Thr, Val, Ile |
| Aromatic Side Chains | Tyr, Phe, Trp, His |

Alternatively, alterations may be made to the protein sequence of many proteins at the amino or carboxy terminus without substantially affecting activity. This can include insertions, deletions or alterations introduced by modern molecular methods, such as polymerase chain reaction (PCR), including PCR amplifications that alter or extend the protein coding sequence by inclusion of amino acid encoding sequences in the oligonucleotides utilized in the PCR amplification. Alternatively, the protein sequences added can include entire protein-coding sequences, to generate protein fusions. Such fusion proteins are often used to (1) increase expression or activity of a protein of interest (2) introduce a binding domain, enzymatic activity or epitope to facilitate either protein purification, protein detection or other experimental uses (3) target secretion or translation of a protein to a subcellular organelle, such as the periplasmic space of Gram-negative bacteria, mitochondria or chloroplasts of plants or the endoplasmic reticulum of eukaryotic cells, the latter of which often results in glycosylation of the protein.

To determine the percent identity of two amino acid sequences or of two nucleic acids, the sequences are aligned for optimal comparison purposes. The percent identity between the two sequences is a function of the number of identical positions shared by the sequences (i.e., percent identity=number of identical positions/total number of positions (e.g., overlapping positions)×100). In one embodiment, the two sequences are the same length. In another embodiment, the percent identity is calculated across the entirety of the reference sequence. The percent identity between two sequences can be determined using techniques similar to those described below, with or without allowing gaps. In calculating percent identity, typically exact matches are counted. A gap, (a position in an alignment where a residue is present in one sequence but not in the other) is regarded as a position with non-identical residues.

The determination of percent identity between two sequences can be accomplished using a mathematical algorithm. A non-limiting example of a mathematical algorithm utilized for the comparison of two sequences is the algorithm incorporated into the BLASTN and BLASTX programs. Karlin and Altschul (1990) Proc. Nat'l. Acad. Sci. USA 87:2264, Altschul et al. (1990) J. Mol. Biol. 215:403, and Karlin and Altschul (1993) Proc. Nat'l. Acad. Sci. USA 90:5873-5877. BLAST nucleotide searches can be performed with the BLASTN program, score=100, word length=12, to obtain nucleotide sequences homologous to nucleic acid molecules disclosed herein. BLAST protein searches can be performed with the BLASTX program, score=50, word length=3, to obtain amino acid sequences homologous to polypeptides disclosed herein. To obtain gapped alignments for comparison purposes, Gapped BLAST (in BLAST 2.0) can be utilized as described in Altschul et al. (1997) Nucleic Acids Res. 25:3389. Alternatively, PSI-Blast can be used to perform an iterated search that detects distant relationships between molecules. See Altschul et al. (1997) supra. When utilizing BLAST, Gapped BLAST, and PSI-Blast programs, the default parameters of the respective programs (e.g., BLASTX and BLASTN) can be used. Alignment may also be performed manually by inspection.

Another non-limiting example of a mathematical algorithm utilized for the comparison of sequences is the ClustalW algorithm (Higgins et al. (1994) Nucleic Acids Res. 22:4673-4680). ClustalW compares sequences and aligns the entirety of the amino acid or DNA sequence, and thus can provide data about the sequence conservation of the entire amino acid sequence. The ClustalW algorithm is used in several commercially available DNA/amino acid analysis software packages, such as the ALIGNX module of the Vector NTI Program Suite (Invitrogen Corporation, Carlsbad, CA). After alignment of amino acid sequences with ClustalW, the percent amino acid identity can be assessed. A non-limiting example of a software program useful for analysis of ClustalW alignments is GENEDOC™. GENEDOC™ (Karl Nicholas) allows assessment of amino acid (or DNA) similarity and identity between multiple proteins. Another non-limiting example of a mathematical algorithm utilized for the comparison of sequences is the algorithm of Myers and Miller (1988) CAB/OS 4(1):11-17. Such an algorithm is incorporated into the ALIGN program (version 2.0), which is part of the GCG Wisconsin Genetics Software Package, Version 10 (available from Accelrys, Inc., San Diego, CA, USA). When utilizing the ALIGN program for comparing amino acid sequences, a PAM120 weight residue table, a gap length penalty of 12, and a gap penalty of 4 can be used. Unless otherwise stated, GAP Version 10, which uses the algorithm of Needleman and Wunsch (1970) J. Mol. Biol. 48(3):443-453, will be used to determine sequence identity or similarity using the following parameters: % identity and % similarity for a nucleotide sequence using GAP Weight of 50 and Length Weight of 3, and the nwsgapdna.cmp scoring matrix; % identity or % similarity for an amino acid sequence using GAP weight of 8 and length weight of 2, and the BLOSUM62 scoring program. Equivalent programs may also be used. By "equivalent program" is intended any sequence comparison program that, for any two sequences in question, generates an alignment having identical nucleotide residue matches and an identical percent sequence identity when compared to the corresponding alignment generated by GAP Version 10.

Isolated or recombinant nucleic acid molecules comprising nucleic acid sequences encoding HECT E3 ligase polypeptides or biologically active portions thereof, as well as nucleic acid molecules sufficient for use as hybridization probes to identify nucleic acid molecules encoding proteins with regions of sequence homology are provided. As used herein, the term "nucleic acid molecule" refers to DNA molecules (e.g., recombinant DNA, cDNA, genomic DNA, plastid DNA, mitochondrial DNA) and RNA molecules (e.g., mRNA) and analogs of the DNA or RNA generated using nucleotide analogs. The nucleic acid molecule can be single-stranded or double-stranded, but preferably is double-stranded DNA.

Nucleotide sequences that encode HECT E3 ligase polypeptides, variants and truncations, may be synthesized and cloned into standard plasmid vectors by conventional means, or may be obtained by standard molecular biology manipulation of other constructs containing the nucleotide sequences.

In some embodiments, plants, plant parts, plant cells, seeds and methods of making and using thereof include a genome modified to contain a deletion. An example of such a deletion is the CR1/CR3 deletion line #1 which contains a 20,117 base pair (bp) deletion corresponding to the sequence beginning at position 2268 and ending at 22,384 of SEQ ID NO In some embodiments, the nucleic acid molecule is a polynucleotide having the sequence set forth in SEQ ID NO: 1, 3, 5, 6, 7, 9 or 11 and variants, fragments and complements thereof. Nucleic acid sequences that are complementary to a nucleic acid sequence of the embodiments or that hybridize to a sequence of the embodiments are also encompassed. The nucleic acid sequences can be used in DNA constructs or expression cassettes for transformation and expression in organisms, including microorganisms and plants. The nucleotide or amino acid sequences may be synthetic sequences that have been designed for expression in an organism including, but not limited to, a microorganism or a plant.

In some embodiments, the nucleic acid molecule encoding the polypeptide is a non-genomic nucleic acid sequence.

In some embodiments, the nucleic acid molecule encoding a polypeptide is a non-genomic polynucleotide having a nucleotide sequence having at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater identity, to the nucleic acid sequence of SEQ ID NO: 2 or 4, wherein the encoded polypeptide is functional to modify a characteristic, such as increased oleic acid, increased oil, increased protein or a combination thereof, of a soybean seed, wherein the encoded polypeptide is functional to increase protein, oil, oleic acid or a combination thereof, of a soybean seed.

Additional sequences which may be combined with those described herein may include those encoding a DGAT sequence, such as SEQ ID NO: 16, those encoding or suppressing expression of a galactinol synthase (GAS) sequence, or those encoding a transcription factor such as ovule development protein (ODP1) or WRINKLED1. The additional sequences may be combined through backcrossing and breeding techniques or may be modified directly in the same plant with the modified HECT E3 ligase sequences.

In some embodiments, the polynucleotide encodes a polypeptide having, or the polypeptide has, at least about 40%, 45%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater sequence identity compared to SEQ ID NO: 2, 4, or 16 and optionally has at least one amino acid substitution, deletion, insertion or combination therefore, compared to the native sequence.

In some embodiments, the nucleic acid molecule encodes a polypeptide comprising, or the polypeptide comprises, an amino acid sequence having at least about 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater identity across the entire length of the amino acid sequence of SEQ ID NO: 2, 4, or 16.

In some embodiments, the nucleic acid has at least about 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99% or greater sequence identity compared to SEQ ID NO: 1, 3, 5, 6, 7, 8, 9 or 10. In some embodiments, the sequence identity is calculated using ClustalW algorithm in the ALIGNX® module of the Vector NTI® Program Suite (Invitrogen Corporation, Carlsbad, CA) with all default parameters. In some embodiments, the sequence identity is across the entire length of polypeptide calculated using ClustalW algorithm in the ALIGNX module of the Vector NTI Program Suite (Invitrogen Corporation, Carlsbad, CA) with all default parameters.

The embodiments also encompass nucleic acid molecules encoding HECT E3 ligase polypeptides variants. "Variants" of the polypeptide encoding nucleic acid sequences include those sequences that encode the polypeptides disclosed herein but that differ conservatively because of the degeneracy of the genetic code as well as those that are sufficiently identical as discussed above. Naturally occurring allelic variants can be identified with the use of well-known molecular biology techniques, such as polymerase chain reaction (PCR) and hybridization techniques as outlined below. Variant nucleic acid sequences also include synthetically derived nucleic acid sequences that have been generated, for example, by using site-directed mutagenesis but which still encode the polypeptides disclosed as discussed below.

Oligonucleotide probes and methods for detecting the polynucleotides described herein are provided. Oligonucleotide probes are detectable nucleotide sequences, such as by an appropriate radioactive label or may be fluorescence as described in, for example, U.S. Pat. No. 6,268,132. As is well known in the art, if the probe molecule and nucleic acid sample hybridize by forming strong base-pairing bonds between the two molecules, it can be reasonably assumed that the probe and sample have substantial sequence homology. Preferably, hybridization is conducted under stringent conditions by techniques well-known in the art, as described, for example, in Keller and Manak (1993). Detection of the probe provides a means for determining in a known manner whether hybridization has occurred. Such a probe analysis provides a rapid method for identifying modified genes of HECT E3 ligase polypeptides, which modified genes and methods are provided. The nucleotide segments which are used as probes can be synthesized using a DNA synthesizer and standard procedures. These nucleotide sequences can also be used as PCR primers to amplify genes.

As is well known to those skilled in molecular biology, similarity of two nucleic acids can be characterized by their tendency to hybridize. Provided are nucleic acids that hybridize to those sequences disclosed herein under stringent conditions. As used herein the terms "stringent conditions" or "stringent hybridization conditions" are intended to refer to conditions under which a probe or nucleic acid will hybridize (anneal) to a particular sequence to a detectably greater degree than to other sequences (e.g. at least 2-fold over background).

Provided are nucleotide constructs comprising sequences described herein. The use of the term "nucleotide constructs" herein is not intended to limit the embodiments to nucleotide constructs comprising DNA. Nucleotide constructs particularly polynucleotides and oligonucleotides composed of ribonucleotides and combinations of ribonucleotides and deoxyribonucleotides may also be employed in the methods disclosed herein. The nucleotide constructs, nucleic acids, and nucleotide sequences of the embodiments additionally encompass all complementary forms of such constructs, molecules, and sequences. Further, the nucleotide constructs, nucleotide molecules, and nucleotide sequences of the embodiments encompass all nucleotide constructs, molecules, and sequences which can be employed in the methods of the embodiments for transforming plants including, but not limited to, those comprised of deoxyribonucleotides, ribonucleotides, and combinations thereof. Such deoxyribonucleotides and ribonucleotides include both naturally occurring molecules and synthetic analogues. The nucleotide constructs, nucleic acids, and nucleotide sequences of the embodiments also encompass all forms of nucleotide constructs including, but not limited to, single-stranded forms, double-stranded forms, hairpins, stem-and-loop structures and the like.

Provided are plants, plant cells, plant seeds and plant nuclei that are modified by gene editing. In some embodiments, gene editing may be facilitated through the induction of a double-stranded break (DSB) or single-strand break, in a defined position in the genome near the desired alteration. DSBs can be induced using any DSB-inducing agent available, including, but not limited to, TALENs (transcription activator-like effector nucleases), meganucleases, zinc finger nucleases, Cas9-gRNA systems (based on bacterial CRISPR-Cas systems), guided cpf1 endonuclease systems, and the like. In some embodiments, the introduction of a DSB can be combined with the introduction of a polynucleotide modification template. In some embodiments, the methods do not use TALENs enzymes or technology and plants and seeds are produced from methods which do not use TALENs enzymes or technology.

A polynucleotide modification template can be introduced into a cell by any method known in the art, such as, but not limited to, transient introduction methods, transfection, electroporation, microinjection, particle mediated delivery, topical application, whiskers mediated delivery, delivery via cell-penetrating peptides, or mesoporous silica nanoparticle (MSN)-mediated direct delivery.

The polynucleotide modification template can be introduced into a cell as a single stranded polynucleotide molecule, a double stranded polynucleotide molecule, or as part of a circular DNA (vector DNA). The polynucleotide modification template can also be tethered to the guide RNA and/or the Cas endonuclease. Tethered DNAs can allow for co-localizing target and template DNA, useful in genome editing and targeted genome regulation, and can also be useful in targeting post-mitotic cells where function of endogenous HR machinery is expected to be highly diminished (Mali et al. 2013 Nature Methods Vol. 10: 957-963.) The polynucleotide modification template may be present transiently in the cell or it can be introduced via a viral replicon.

A "modified nucleotide" or "edited nucleotide" refers to a nucleotide sequence of interest that comprises at least one alteration when compared to its non-modified nucleotide sequence. Such "alterations" include, for example: (i) replacement of at least one nucleotide, (ii) a deletion of at least one nucleotide, (iii) an insertion of at least one nucleotide, or (iv) any combination of (i)-(iii).

The term "polynucleotide modification template" includes a polynucleotide that comprises at least one nucleotide modification when compared to the nucleotide sequence to be edited. A nucleotide modification can be at least one nucleotide substitution, addition or deletion. Optionally, the polynucleotide modification template can further comprise homologous nucleotide sequences flanking the at least one nucleotide modification, wherein the flanking homologous nucleotide sequences provide sufficient homology to the desired nucleotide sequence to be edited.

The process for editing a genomic sequence combining DSB and modification templates generally comprises: providing to a host cell, a DSB-inducing agent, or a nucleic acid encoding a DSB-inducing agent, that recognizes a target sequence in the chromosomal sequence and is able to induce a DSB in the genomic sequence, and at least one polynucleotide modification template comprising at least one nucleotide alteration when compared to the nucleotide sequence to be edited. The polynucleotide modification template can further comprise nucleotide sequences flanking the at least one nucleotide alteration, in which the flanking sequences are substantially homologous to the chromosomal region flanking the DSB.

The endonuclease can be provided to a cell by any method known in the art, for example, but not limited to transient introduction methods, transfection, microinjection, and/or topical application or indirectly via recombination constructs. The endonuclease can be provided as a protein or as a guided polynucleotide complex directly to a cell or indirectly via recombination constructs. The endonuclease can be introduced into a cell transiently or can be incorporated into the genome of the host cell using any method known in the art. In the case of a CRISPR-Cas system, uptake of the endonuclease and/or the guided polynucleotide into the cell can be facilitated with a Cell Penetrating Peptide (CPP) as described in WO2016073433 published May 12, 2016.

TAL effector nucleases (TALEN) are a class of sequence-specific nucleases that can be used to make double-strand breaks at specific target sequences in the genome of a plant or other organism. (Miller et al. (2011) Nature Biotechnology 29:143-148).

Endonucleases are enzymes that cleave the phosphodiester bond within a polynucleotide chain. Endonucleases include restriction endonucleases, which cleave DNA at specific sites without damaging the bases, and meganucleases, also known as homing endonucleases (HEases), which like restriction endonucleases, bind and cut at a specific recognition site, however the recognition sites for meganucleases are typically longer, about 18 bp or more (patent application PCT/US12/30061, filed on Mar. 22, 2012). Meganucleases have been classified into four families based on conserved sequence motifs, the families are the LAGLIDADG, GIY-YIG, H-N-H, and His-Cys box families. These motifs participate in the coordination of metal ions and hydrolysis of phosphodiester bonds.

Zinc finger nucleases (ZFNs) are engineered double-strand break inducing agents comprised of a zinc finger DNA binding domain and a double-strand-break-inducing agent domain. Recognition site specificity is conferred by the zinc finger domain, which typically comprising two, three, or four zinc fingers, for example having a C2H2 structure, however other zinc finger structures are known and have been engineered.

Genome editing using DSB-inducing agents, such as Cas9-gRNA complexes, has been described, for example in U.S. Patent Application US 2015-0082478 A1, published on Mar. 19, 2015, WO2015/026886 A1, published on Feb. 26, 2015, WO2016007347, published on Jan. 14, 2016, and WO201625131, published on Feb. 18, 2016, all of which are incorporated by reference herein.

The term "Cas gene" herein refers to a gene that is generally coupled, associated or close to, or in the vicinity of flanking CRISPR loci in bacterial systems. The terms "Cas gene", "CRISPR-associated (Cas) gene" are used interchangeably herein. The term "Cas endonuclease" herein refers to a protein encoded by a Cas gene. A Cas endonuclease herein, when in complex with a suitable polynucleotide component, is capable of recognizing, binding to, and optionally nicking or cleaving all or part of a specific DNA target sequence. A Cas endonuclease described herein comprises one or more nuclease domains. Cas endonucleases of the disclosure includes those having a HNH or HNH-like nuclease domain and/or a RuvC or RuvC-like nuclease domain. A Cas endonuclease of the disclosure includes a Cas9 protein, a Cpf1 protein, a C2c1 protein, a C2c2 protein, a C2c3 protein, Cas3, Cas 5, Cas7, Cas8, Cas10, or complexes of these.

As used herein, the terms "guide polynucleotide/Cas endonuclease complex", "guide polynucleotide/Cas endonuclease system", "guide polynucleotide/Cas complex", "guide polynucleotide/Cas system", "guided Cas system" are used interchangeably herein and refer to at least one guide polynucleotide and at least one Cas endonuclease that are capable of forming a complex, wherein said guide polynucleotide/Cas endonuclease complex can direct the Cas endonuclease to a DNA target site, enabling the Cas endonuclease to recognize, bind to, and optionally nick or cleave (introduce a single or double strand break) the DNA target site. A guide polynucleotide/Cas endonuclease complex herein can comprise Cas protein(s) and suitable polynucleotide component(s) of any of the four known CRISPR systems (Horvath and Barrangou, 2010*, Science* 327:167-170) such as a type I, II, or III CRISPR system. A Cas endonuclease unwinds the DNA duplex at the target sequence and optionally cleaves at least one DNA strand, as mediated by recognition of the target sequence by a polynucleotide (such as, but not limited to, a crRNA or guide RNA) that is in complex with the Cas protein. Such recognition and cutting of a target sequence by a Cas endonuclease typically occurs if the correct protospacer-adjacent motif (PAM) is located at or adjacent to the 3' end of the DNA target sequence. Alternatively, a Cas protein herein may lack DNA cleavage or nicking activity, but can still specifically bind to a DNA target sequence when complexed with a suitable RNA component. (See also U.S. Patent Application US 2015-0082478 A1, published on Mar. 19, 2015 and US 2015-0059010 A1, published on Feb. 26, 2015, both are hereby incorporated in its entirety by reference).

A guide polynucleotide/Cas endonuclease complex can cleave one or both strands of a DNA target sequence. A guide polynucleotide/Cas endonuclease complex that can cleave both strands of a DNA target sequence typically comprise a Cas protein that has all of its endonuclease domains in a functional state (e.g., wild type endonuclease domains or variants thereof retaining some or all activity in each endonuclease domain). Non-limiting examples of Cas9 nickases suitable for use herein are disclosed in U.S. Patent Appl. Publ. No. 2014/0189896, which is incorporated herein by reference.

Other Cas endonuclease systems have been described in PCT patent applications PCT/US16/32073, filed May 12, 2016 and PCT/US16/32028 filed May 12, 2016, both applications incorporated herein by reference.

"Cas9" (formerly referred to as Cas5, Csn1, or Csx12) herein refers to a Cas endonuclease of a type II CRISPR system that forms a complex with a crNucleotide and a tracrNucleotide, or with a single guide polynucleotide, for specifically recognizing and cleaving all or part of a DNA target sequence. Cas9 protein comprises a RuvC nuclease domain and an HNH (H—N—H) nuclease domain, each of which can cleave a single DNA strand at a target sequence (the concerted action of both domains leads to DNA double-strand cleavage, whereas activity of one domain leads to a nick). In general, the RuvC domain comprises subdomains I, II and III, where domain I is located near the N-terminus of Cas9 and subdomains II and III are located in the middle of the protein, flanking the HNH domain (Hsu et al, Cell 157:1262-1278). A type II CRISPR system includes a DNA cleavage system utilizing a Cas9 endonuclease in complex with at least one polynucleotide component. For example, a Cas9 can be in complex with a CRISPR RNA (crRNA) and a trans-activating CRISPR RNA (tracrRNA). In another example, a Cas9 can be in complex with a single guide RNA.

Any guided endonuclease can be used in the methods disclosed herein. Such endonucleases include, but are not limited to Cas9 and Cpf1 endonucleases. Many endonucleases have been described to date that can recognize specific PAM sequences (see for example—Jinek et al. (2012) Science 337 p 816-821, PCT patent applications PCT/US16/32073, filed May 12, 2016 and PCT/US16/32028 filed May 12, 2016 and Zetsche B et al. 2015. Cell 163, 1013) and cleave the target DNA at a specific position. It is understood that based on the methods and embodiments described herein utilizing a guided Cas system one can now tailor these methods such that they can utilize any guided endonuclease system.

The guide polynucleotide can also be a single molecule (also referred to as single guide polynucleotide) comprising a crNucleotide sequence linked to a tracrNucleotide sequence. The single guide polynucleotide comprises a first nucleotide sequence domain (referred to as Variable Targeting domain or VT domain) that can hybridize to a nucleotide sequence in a target DNA and a Cas endonuclease recognition domain (CER domain), that interacts with a Cas endonuclease polypeptide. By "domain" it is meant a contiguous stretch of nucleotides that can be RNA, DNA, and/or RNA-DNA-combination sequence. The VT domain and/or the CER domain of a single guide polynucleotide can comprise a RNA sequence, a DNA sequence, or a RNA-DNA-combination sequence. The single guide polynucleotide being comprised of sequences from the crNucleotide and the tracrNucleotide may be referred to as "single guide RNA" (when composed of a contiguous stretch of RNA nucleotides) or "single guide DNA" (when composed of a contiguous stretch of DNA nucleotides) or "single guide RNA-DNA" (when composed of a combination of RNA and DNA nucleotides). The single guide polynucleotide can form a complex with a Cas endonuclease, wherein said guide polynucleotide/Cas endonuclease complex (also referred to as a guide polynucleotide/Cas endonuclease system) can direct the Cas endonuclease to a genomic target site, enabling the Cas endonuclease to recognize, bind to, and optionally nick or cleave (introduce a single or double strand break) the target site.

The term "variable targeting domain" or "VT domain" is used interchangeably herein and includes a nucleotide sequence that can hybridize (is complementary) to one strand (nucleotide sequence) of a double strand DNA target site. In some embodiments, the variable targeting domain comprises a contiguous stretch of 12 to 30 nucleotides. The variable targeting domain can be composed of a DNA sequence, a RNA sequence, a modified DNA sequence, a modified RNA sequence, or any combination thereof.

The terms "single guide RNA" and "sgRNA" are used interchangeably herein and relate to a synthetic fusion of two RNA molecules, a crRNA (CRISPR RNA) comprising a variable targeting domain (linked to a tracr mate sequence that hybridizes to a tracrRNA), fused to a tracrRNA (trans-activating CRISPR RNA). The single guide RNA can comprise a crRNA or crRNA fragment and a tracrRNA or tracrRNA fragment of the type II CRISPR/Cas system that can form a complex with a type II Cas endonuclease, wherein said guide RNA/Cas endonuclease complex can direct the Cas endonuclease to a DNA target site, enabling the Cas endonuclease to recognize, bind to, and optionally nick or cleave (introduce a single or double strand break) the DNA target site.

The terms "guide RNA/Cas endonuclease complex", "guide RNA/Cas endonuclease system", "guide RNA/Cas complex", "guide RNA/Cas system", "gRNA/Cas complex", "gRNA/Cas system", "RNA-guided endonuclease", "RGEN" are used interchangeably herein and refer to at least one RNA component and at least one Cas endonuclease that are capable of forming a complex, wherein said guide RNA/Cas endonuclease complex can direct the Cas endonuclease to a DNA target site, enabling the Cas endonuclease to recognize, bind to, and optionally nick or cleave (introduce a single or double strand break) the DNA target site. A guide RNA/Cas endonuclease complex herein can comprise Cas protein(s) and suitable RNA component(s) of any of the four known CRISPR systems (Horvath and Barrangou, 2010, Science 327:167-170) such as a type I, II, or III CRISPR system. A guide RNA/Cas endonuclease complex can comprise a Type II Cas9 endonuclease and at least one RNA component (e.g., a crRNA and tracrRNA, or a gRNA).

The guide polynucleotide can be introduced into a cell transiently, as single stranded polynucleotide or a double stranded polynucleotide, using any method known in the art such as, but not limited to, particle bombardment, *Agrobacterium* transformation or topical applications. The guide polynucleotide can also be introduced indirectly into a cell by introducing a recombinant DNA molecule (via methods such as, but not limited to, particle bombardment or *Agrobacterium* transformation) comprising a heterologous nucleic acid fragment encoding a guide polynucleotide, operably linked to a specific promoter that is capable of transcribing the guide RNA in said cell. The specific promoter can be, but is not limited to, a RNA polymerase III promoter, which allow for transcription of RNA with precisely defined, unmodified, 5'- and 3'-ends (DiCarlo et al., Nucleic Acids Res. 41: 4336-4343; Ma et al., Mol. Ther. Nucleic Acids 3:e161) as described in WO2016025131, published on Feb. 18, 2016, incorporated herein in its entirety by reference.

Provided are plants, plant cells, plant seeds and plant nuclei that are transformed with sequences described herein. Transformation may be stable or transient. "Stable transformation" as used herein means that the nucleotide construct introduced into a plant integrates into the genome of the plant and is capable of being inherited by the progeny thereof. "Transient transformation" as used herein means that a polynucleotide is introduced into the plant and does not integrate into the genome of the plant or a polypeptide is introduced into a plant. "Plant" as used herein refers to whole plants, plant organs (e.g., leaves, stems, roots, etc.), seeds, plant cells, propagules, embryos and progeny of the same. Plant cells can be differentiated or undifferentiated (e.g. callus, suspension culture cells, protoplasts, leaf cells, root cells, phloem cells and pollen).

Transformation methods include introduction of a recombinant DNA construct comprising an expression cassette. Provided are constructs which include one or more heterologous promoter sequences operably connected to one or more polynucleotides encoding polypeptides disclosed herein and appropriate transcription termination sequences and plants, seeds, cells and nuclei containing the recombinant DNA construct or expression cassette.

Transformation methods include introduction of a suppression DNA construct or a construct that results in increased expression of a target gene, such as encoding the HECT E3 ligase polypeptides. "Suppression DNA construct" is a recombinant DNA construct which when transformed or stably integrated into the genome of the plant, results in "silencing" of a target gene in the plant. The target gene may be endogenous or transgenic to the plant. "Silencing," as used herein with respect to the target gene, refers generally to the suppression of levels of mRNA or protein/enzyme expressed by the target gene, and/or the level of the enzyme activity or protein functionality. The term "suppression" includes lower, reduce, decline, decrease, inhibit, eliminate and prevent. "Silencing" or "gene silencing" does not specify mechanism and is inclusive, and not limited to, anti-sense, cosuppression, viral-suppression, hairpin suppression, stem-loop suppression, RNAi-based approaches and small RNA-based approaches.

The embodiments further relate to plant-propagating material of a transformed plant of the embodiments including, but not limited to, seeds, tubers, corms, bulbs, leaves and cuttings of roots and shoots. Methods of plant breeding by crossing a modified plant described herein with a second different plant are provided. Progeny plants, plant cells, seeds and plant nuclei from such breeding methods are provided, such as F1 progeny plants, plant cells, seeds and plant nuclei.

Transformation of any plant species can be carried out, including, but not limited to, monocots and dicots. Examples of plants of interest include, but are not limited to, corn (*Zea mays*), *Brassica* sp. (e.g., *B. napus, B. rapa, B. juncea*), particularly those *Brassica* species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (Carthamus tinctorius), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassava (*Manihot esculenta*), coffee (*Coffea* spp.), coconut (*Cocos nucifera*), pineapple (*Ananas comosus*), citrus trees (Citrus spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), *papaya* (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oats, barley, vegetables ornamentals, and conifers.

Plants of interest include grain plants that provide seeds of interest, oil-seed plants, and leguminous plants. Seeds of interest include grain seeds, such as corn, wheat, barley, rice, sorghum, rye, millet, etc. Oil-seed plants include cotton, soybean, safflower, sunflower, *Brassica*, maize, alfalfa, palm, coconut, flax, castor, olive, etc. Leguminous plants include beans and peas. Beans include guar, locust bean, fenugreek, soybean, garden beans, cowpea, mung bean, lima bean, fava bean, lentils, chickpea, etc.

The methods comprise providing a plant or plant cell expressing a polynucleotide encoding the polypeptide sequence disclosed herein and growing the plant or a seed thereof in a field. In some embodiments, the expression or altered activity of the modified polypeptide results in a plant producing increased yield or biomass.

As defined herein, the "yield" of the plant refers to the quality and/or quantity of biomass produced by the plant. "Biomass" as used herein refers to any measured plant product. An increase in biomass production is any improvement in the yield of the measured plant product. Increasing plant yield has several commercial applications. An increase in yield can comprise any statistically significant increase including, but not limited to, at least a 1% increase, at least a 3% increase, at least a 5% increase, at least a 10% increase, at least a 20% increase, at least a 30%, at least a 50%, at least a 70%, at least a 100% or a greater increase in yield compared to a plant not expressing the modified sequence.

Methods of detecting the modified polynucleotides are provided. Methods of extracting modified DNA from a sample or detecting the presence of DNA corresponding to the modified genomic sequences comprising deletions, insertions, substitutions or inversions such as described herein be carried out. Such methods of detecting polynucleotides comprise contacting a sample comprising soybean genomic DNA with a DNA primer set, that when used in a nucleic acid amplification reaction, such as the polymerase chain reaction (PCR), with genomic DNA extracted from soybeans produces an amplicon that is diagnostic for either the presence or absence of the deleted sequence, or one or more HECT E3 ligase coding sequences. The methods include the steps of performing a nucleic acid amplification reaction, thereby producing the amplicon and detecting the amplicon.

In some embodiments one of the pair of DNA molecules comprises the wild type sequence where the modification occurs with the second of the pair being upstream or downstream as appropriate and suitably in proximity to the wild type sequence where the modification occurs, such that an amplicon is produced when the wild type sequence is present, but no amplicon is produced when the deletion is present. In the context of the methods, in proximity means sufficiently close such that the distance between the first and second of the pair of DNA molecules facilitates the production of an amplicon when included in a DNA amplification reaction comprising soybean genomic DNA. For example, the second primer may bind at a location beginning at, within or less than 1, 2, 5, 10, 20, 30, 40, 50, 60, 70, 80, 90, 100, 150, 200, 250, 300, 350, 400, 450, 500, 600, 700, 800, 900, 1000, 1500, 16, 1700, 1800, 1900, 2000, 2100, 2200, 2300, 2400, 2500, 2600, 2700, 2800, 2900, 3000, 3500, 4000, 4500, 5000, 5500, 6000, 6500, 7000, 7500, 8000, 8500, 9000, 9500 or 10000 nucleotides upstream or downstream of the end of the binding site of the first DNA primer molecule.

Probes and primers are provided which are of sufficient nucleotide length to bind specifically to the target DNA sequence under the reaction or hybridization conditions. Suitable probes and primers are at least 10, 11, 12, 13, 14, 15, 16, 17, 18, 19, 20, 21, 22, 23, 24, 25, 26, 27, 28, 29 or 30 nucleotides in length, and less than 35, 34, 33, 32, 31, 30, 29, 28, 27, 26, 2,5 2,4 23, 22, 21, 20, 19, 18, 17, 16, 15, 14, 13, or 12 nucleotides in length. Such probes and primers can hybridize specifically to a target sequence under high stringency hybridization conditions. Preferably, probes and primers have complete or 100% DNA sequence similarity of contiguous nucleotides with the target sequence, although probes which differ from the target DNA sequence but retain the ability to hybridize to target DNA sequence may be also be used. Reverse complements of the primers and probes disclosed herein are also provided and can be used in the methods and compositions described herein.

In some embodiments, one of the pair of DNA molecules comprises the modification or traverses the modification junction, with the second DNA molecule of the pair being upstream or downstream of the genomic sequence as appropriate, such that an amplicon is produced when the modified allele is present, but no amplicon is produced when the wild type allele is present, or vice versa. Suitable primers for use in reactions to detect the presence of the modified alleles can be designed based on the junction sequences described herein. In some embodiments, the primers bind to the target sequence to produce an amplicon of a length described herein. The amplicon molecule produced can be at least 5, 10, 15, 20, 25, 30, 35, 40, 41, 42, 43, 44, 45, 46, 47, 48, 49, 50, 60, 70, 80, 90, 100, 125, 150, 175, 200, 225, 250, 275, 300, 350, 400, 450, 500, 550, 600, 650, 700, 750, 800, 850, 900, 950, 1000, 1500 or 2000 nucleotides in length and less than about 10000, 9000, 8000, 7500, 7000, 6500, 6000, 5500, 5000, 4500, 4000, 3500, 3000, 2500, 2000, or 1500 nucleotides in length.

A methods of plant breeding are provided where a soybean plant is advanced in a plant breeding program. The plant comprises a modified polynucleotide disclosed herein which modification may occur in SEQ ID NO: 5 or 9 resulting in decreased expression of SEQ ID NO: 2 or 4. A DNA sample is obtained from the modified soybean plant which DNA sample includes the modified polynucleotide and is contacted with a first and a second primer molecule. The first primer molecule binds to a region upstream of or including the modification in SEQ ID NO: 5 or 9 and the second primer molecule binds to a genomic region downstream of or including the modification in SEQ ID NO: 5 or 9 respectively. A nucleic acid amplification reaction is performed to produce a DNA amplicon molecule which is detected and indicates whether the modified polynucleotide is present whether the plant should be advanced in the plant breeding program. The soybean plant or a plant grown from seeds produced therefrom can be selfed or crossed with another soybean plant to produce progeny seed The plant comprising the modified polynucleotide produces a seed having an altered characteristic relative to that of a control seed produced from a control plant not comprising the modified polynucleotide, selected from at least one of: (a) fatty acids with increased oleic acid content, (b) fatty acids with decreased linoleic acid content; (c) fatty acids with decreased linolenic acid content; (d) fatty acids with decreased stearic acid content; (e) fatty acids with decreased palmitic acid content; (f) a reduced soluble carbohydrate content, and (g) an increased protein content. Progeny seed produced in the breeding program may comprise the modified polynucleotide and have an altered characteristic relative to that of progeny seed from a control plant not comprising the modified polynucleotide selected from at least one of: (a) fatty acids with increased oleic acid content, (b) fatty acids with decreased linoleic acid content; (c) fatty acids with decreased linolenic acid content; (d) fatty acids with decreased stearic acid content; (e) fatty acids with decreased palmitic acid content; (f) a reduced soluble carbohydrate content, and (g) an increased protein content.

The foregoing invention has been described in detail by way of illustration and example for purposes of clarity and understanding. As is readily apparent to one skilled in the art, the foregoing disclosures are only some of the methods and compositions that illustrate the embodiments of the foregoing invention. It will be apparent to those of ordinary skill in the art that variations, changes, modifications, and alterations may be applied to the compositions and/or methods described herein without departing from the true spirit, concept, and scope of the invention.

All publications, patents, and patent applications mentioned in the specification are incorporated by reference herein for the purpose cited to the same extent as if each was specifically and individually indicated to be incorporated by reference herein.

As used herein and in the appended claims, the singular forms "a", "an", and "the" include plural reference unless the context clearly dictates otherwise. Thus, for example, reference to "a plant" includes a plurality of such plants, reference to "a cell" includes one or more cells and equivalents thereof known to those skilled in the art, and so forth. Unless expressly stated to the contrary, "or" is used as an inclusive term. For example, a condition A or B is satisfied by any one of the following: A is true (or present) and B is false (or not present), A is false (or not present) and B is true (or present), and both A and B are true (or present).

The following examples illustrate particular aspects of the disclosure and are not intended in any way to limit the disclosure.

EXAMPLES

Example 1. Genome Editing of HECT Ubiquitin E3 Ligase (HEL) Genes

For genome engineering applications, the type II CRISPR/Cas system minimally requires the Cas9 protein and a duplexed crRNA/tracrRNA molecule or a synthetically fused crRNA and tracrRNA (guide RNA) molecule for DNA target site recognition and cleavage (Gasiunas et al. (2012) *Proc. Natl. Acad. Sci. USA* 109: E2579-86, Jinek et al. (2012) *Science* 337:816-21, Mali et al. (2013) *Science* 339:823-26, and Cong et al. (2013) *Science* 339:819-23). Described herein is a guideRNA/Cas endonuclease system that is based on the type II CRISPR/Cas system and consists of a Cas endonuclease and a guide RNA (or duplexed crRNA and tracrRNA) that together can form a complex that recognizes a genomic target site in a plant and introduces a double-strand-break into said target site.

To use the guide RNA/Cas endonuclease system in soybean, the Cas9 gene from *Streptococcus pyogenes* M1 GAS (SF370) was soybean codon optimized per standard techniques known in the art. To facilitate nuclear localization of the Cas9 protein in soybean cells, Simian virus 40 (SV40) monopartite amino terminal nuclear localization signal (MAPKKKRKV) and *Agrobacterium tumefaciens* bipartite VirD2 T-DNA border endonuclease carboxyl terminal nuclear localization signal (KRPRDRHDGELGGRKRAR) were incorporated at the amino and carboxyl-termini of the Cas9 open reading frame, respectively. The soybean optimized Cas9 gene was operably linked to a soybean constitutive promoter such as the strong soybean constitutive promoter GM-EF1A2 (US patent application 20090133159) or regulated promoter by standard molecular biological techniques.

The second component to form a functional guide RNA/Cas endonuclease system for genome engineering applications is a duplex of the crRNA and tracrRNA molecules or a synthetic fusing of the crRNA and tracrRNA molecules, a guide RNA. To confer efficient guide RNA expression (or expression of the duplexed crRNA and tracrRNA) in soybean, the soybean U6 polymerase III promoter and U6 polymerase III terminator were used.

Plant U6 RNA polymerase III promoters have been cloned and characterized from such as *Arabidopsis* and *Medicago truncatula* (Waibel and Filipowicz, NAR 18:3451-3458 (1990); Li et al., J. Integrat. Plant Biol. 49:222-229 (2007); Kim and Nam, Plant Mol. Biol. Rep. 31:581-593 (2013); Wang et al., RNA 14:903-913 (2008)). Soybean U6 small nuclear RNA (snRNA) genes were identified herein by searching public soybean variety Williams82 genomic sequence using *Arabidopsis* U6 gene coding sequence. Approximately 0.5 kb genomic DNA sequence upstream of the first G nucleotide of a U6 gene was selected to be used as a RNA polymerase III promoter, for example, GM-U6-13.1 promoter or GM-U6-9.1 promoter, to express guide RNA to direct Cas9 nuclease to designated genomic site. The guide RNA coding sequence was 76 bp long and comprised a 20 bp variable targeting domain from a chosen soybean genomic target site on the 5' end and a tract of 4 or more T residues as a transcription terminator on the 3' end. The first nucleotide of the 20 bp variable targeting domain was a G residue to be used by RNA polymerase III for transcription. Other soybean U6 homologous genes promoters were similarly cloned and used for small RNA expression.

Since the Cas9 endonuclease and the guide RNA need to form a protein/RNA complex to mediate site-specific DNA double strand cleavage, the Cas9 endonuclease and guide RNA must be expressed in same cells. To improve their co-expression and presence, the Cas9 endonuclease and guide RNA expression cassettes were linked into a single DNA construct.

The ubiquitin proteasome system is involved the regulation of nearly every aspect of plant growth and development by controlling protein degradation. Further functional analysis of HECT E3 ligases was undertaken to provide insights of the role of each gene in soybean.

Two soybean HECT E3 ligase genes were identified with constitutive expression in all tissues including developing seeds (Table 3). To exam the functions of two HECT E3 Ligase (HEL) genes—HEL1, chromosome 4 and HEL2, chromosome 6—in soybean, several gRNA were designed to knockout two genes individually or together (Table1). A guide RNA (GM-HEL-CR1) was designed in the exon1 of the HEL1 and HEL2) to knockout both genes at the same time. A pair of guides (GM-HEL-CR5 and GM-HEL-CR6) were also designed to dropout only the HEL1 (chromosome 4) gene. A second pair of guides (GM-HEL-CR7 and GM-HEL-CR8) were also designed to dropout only the HEL2 (chromosome 6) gene. Combination of GM-HEL-CR7 and GM-HEL-CR1 will delete or mutate or rearrange the genomic fragment from promoter to the exon1 of the HEL1 gene.

TABLE 3

Expression of HEL1 (chromosome 4) and HEL2 (chromosome 6) genes

| Sample | (HEL1 - Chr, 4) PPM | (HEL2 - Chr 6) PPM |
|---|---|---|
| soy__embryogenic__suspension__culture (cell culture) | 95.3 | 46.6 |
| soy__cotyledons (cotyledon) | 186.4 | 135.8 |
| soy__somatic__embryos__germination (embryo) | 120.0 | 90.2 |
| soy__somatic__embryos__dry__down (embryo) | 272.5 | 48.9 |
| soy__somatic__embryos__maturation__SHAM (embryo) | 77.2 | 72.8 |
| soy__somatic__embryos__maturation (embryo) | 94.2 | 130.7 |
| soy__flower (flower) | 84.6 | 55.2 |
| soy__flower__cluster (flower) | 70.8 | 52.9 |
| soy__leaf__flowering (leaf) | 298.9 | 149.2 |
| soy__leaf__first__trifolate (leaf) | 143.1 | 219.5 |
| soy__shoot__apical__meristem (meristem) | 58.4 | 51.5 |
| soy__leaflet__petiole (petiole) | 49.4 | 43.3 |
| soy__main__petiole (petiole) | 40.8 | 40.7 |
| soy__pods__1 cm (pod) | 96.5 | 70.6 |
| soy__pods__2 cm (pod) | 70.3 | 55.0 |
| soy__root__seedling (root) | 41.9 | 28.8 |
| soy__root__tips__seedling (root) | 32.8 | 26.9 |
| soy__seed__50__DAF (seed) | 71.4 | 175.9 |
| soy__seed__30__DAF (seed) | 44.3 | 70.5 |
| soy__seed__15__DAF (seed) | 73.1 | 41.8 |
| soy__seed__50DAF (seed) | 251.6 | 46.6 |
| soy__stem (stem) | 47.1 | 34.0 |

TABLE 4

| Guide RNA designed to edit region of interest | | | | | |
|---|---|---|---|---|---|
| Edit Designation (guide pair) | Approximate expected deletion size (bp) | Guide 1 name | Guide 1 sequence | Guide 2 name | Guide 2 sequence |
| GM-HEL-CR1 | | GM-HEL-CR1 | GGAAGAAGGTCGTCAGGTTG (SEQ ID NO: 11) | | |
| GM-HEL-CR7/CR1 | 901 bp | GM-HEL-CR7 | GGAGCTGAAAACGACGCGGA (SEQ ID NO: 14) | GM-HEL-CR1 | GGAAGAAGGTCGTCAGGTTG (SEQ ID NO: 11) |
| GM-HEL-CR5/CR6 | 12728 bp | GM-HEL-CR5 | GCATAGAACGGTGCCAATCA (SEQ ID NO: 12) | GM-HEL-CR6 | GAAGATAAATCTGCAAACGT (SEQ ID NO: 13) |
| GM-HEL-CR7/CR8 | 11682 bp | GM-HEL-CR7 | GGAGCTGAAAACGACGCGGA (SEQ ID NO: 14) | GM-HEL-CR8 | GCGGTATTTGCGTTGTTAGG (SEQ ID NO: 15) |

The soybean U6 small nuclear RNA promoter, GM-U6-13.1 promoter or GM-U6-9.1 promoter, was used to express guide RNAs to direct Cas9 nuclease to designated genomic target sites. A soybean codon optimized Cas9 endonuclease expression cassette and guide RNA expression cassettes were linked in the plasmid. The constructs were delivered into soybean plants by either bombardment based embryogenic culture transformation or by *Ochrobactrum*-mediated soybean embryonic axis transformation.

For bombardment-based soy transformation, soybean somatic embryogenic suspension cultures were induced from a DuPont Pioneer proprietary elite cultivar 93Y21 as follows. Cotyledons (~3 mm in length) were dissected from surface sterilized, immature seeds and were cultured for 6-10 weeks in the light at 26° C. on a Murashige and Skoog (MS) media containing 0.7% agar and supplemented with 10 mg/ml 2,4-D (2,4-Dichlorophenoxyacetic acid). Globular stage somatic embryos, which produced secondary embryos, were then excised and placed into flasks containing liquid MS medium supplemented with 2,4-D (10 mg/ml) and cultured in light on a rotary shaker. After repeated selection for clusters of somatic embryos that multiplied as early, globular staged embryos, the soybean embryogenic suspension cultures were maintained in 35 ml liquid media on a rotary shaker, 150 rpm, at 26° C. with fluorescent lights on a 16:8-hour day/night schedule. Cultures were subcultured every two weeks by inoculating approximately 35 mg of tissue into 35 ml of the same fresh liquid MS medium.

Soybean embryogenic suspension cultures were then transformed by the method of particle gun bombardment using a DuPont Biolistic™ PDS1000/HE instrument (Bio-Rad Laboratories, Hercules, CA). To 50 μl of a 60 mg/ml 1.0 mm gold particle suspension were added in order: 30 μl of equal amount (30 ng/μl) plasmid DNA, 20 μl of 0.1 M spermidine, and 25 μl of 5 M $CaCl_2$. The particle preparation was then agitated for 3 minutes, spun in a centrifuge for 10 seconds and the supernatant removed. The DNA-coated particles were then washed once in 400 μl 100% ethanol and resuspended in 45 μl of 100% ethanol. The DNA/particle suspension was sonicated three times for one second each. Then 5 μl of the DNA-coated gold particles was loaded on each macro carrier disk.

Approximately 300-400 mg of a two-week-old suspension culture was placed in an empty 60×15 mm Petri dish and the residual liquid removed from the tissue with a pipette. For each transformation experiment, approximately 5 to 10 plates of tissue were bombarded. Membrane rupture pressure was set at 1100 psi and the chamber was evacuated to a vacuum of 28 inches mercury. The tissue was placed approximately 3.5 inches away from the retaining screen and bombarded once. Following bombardment, the tissue was divided in half and placed back into liquid media and cultured as described above.

Five to seven days post bombardment, the liquid media was exchanged with fresh media containing 30 mg/ml hygromycin as selection agent. This selective media was refreshed weekly. Seven to eight weeks post bombardment, green, transformed tissue was observed growing from untransformed, necrotic embryogenic clusters. Isolated green tissue was removed and inoculated into individual flasks to generate new, clonally propagated, transformed embryogenic suspension cultures. Each clonally propagated culture was treated as an independent transformation event and subcultured in the same liquid MS media supplemented with 2,4-D (10 mg/ml) and 30 ng/ml hygromycin selection agent to increase mass. The embryogenic suspension cultures were then transferred to agar solid MS media plates without 2,4-D supplement to allow somatic embryos to develop. A sample of each event was collected at this stage for quantitative PCR analysis.

Cotyledon stage somatic embryos were dried-down (by transferring them into an empty small Petri dish that was seated on top of a 10 cm Petri dish containing some agar gel to allow slow dry down) to mimic the last stages of soybean seed development. Dried-down embryos were placed on germination solid media and transgenic soybean plantlets were regenerated. The transgenic plants were then transferred to soil and maintained in growth chambers for seed production. Transgenic events were sampled at somatic embryo stage or TO leaf stage for molecular analysis.

For the *Ochrobactrum*-mediated soybean embryonic axis transformation, the construct was transformed into *Ochrobactrum haywardense* H1-8 strain. *Ochrobactrum*-mediated soybean embryonic axis transformation is done essentially as described in US Patent application US 2018/0216123 A1. Mature dry seeds of soybean cultivar 93Y21 are disinfected using chlorine gas and imbibed on semi-solid medium containing 5 g/l sucrose and 6 g/l agar at room temperature in the dark. After an overnight incubation, the seed is soaked in distilled water for an additional 3-4 hrs at room temperature in the dark. Intact embryonic axis is isolated from cotyledon using a scapel blade in distilled sterile water. The embryonic axis explants are transferred to the deep plate with 15 mL of *Ochrobactrum haywardense* H1-8 further containing a helper vector PHP85634 (RV005393) with binary vector RV029968 or RV029969 with suspension at OD600=0.5 in infection medium containing 200 μM acetosyringone. The plates are sealed with parafilm ("Parafilm M" VWR Cat #52858), then sonicated (Sonicator-VWR model 50T) for 30 seconds. After sonication, embryonic axis explants are transferred to a single layer of autoclaved sterile filter paper (VWR #415/Catalog #28320-020). The plates are sealed with Micropore tape (Catalog #1530-0, 3M, St. Paul, MN)) and incubated under dim light (5-10 μE/m$^2$/s, cool white fluorescent lamps) for 16 hrs at 21° C. for 3 days.

After co-cultivation, the embryonic axis explants are cultured on shoot induction medium solidified with 0.7% agar in the absence of selection. The base of the explant (i.e., root radical of embryonic axis) is embedded in the medium. Shoot induction is carried out in a Percival Biological Incubator at 26° C. with a photoperiod of 18 hrs and a light intensity of 40-70 μE/m$^2$/s. 6 to 7 weeks after transformation, elongated shoots (>1-2 cm) are isolated and transferred to rooting medium containing selection agent. Transgenic plantlets are transferred to soil pots and were grown in the greenhouse.

From bombardment-based soybean transformation experiments, in which the GM-HEL-CR1 and GM-HEL-CR7 were introduced into soybean at the same time, two events were generated (SOY8672.7.1 and Soy8605.2.1). Genomic DNA is extracted from soybean samples and analyzed by regular PCR. PCR primers are designed to amplify the genomic region of interests. The PCR bands are cloned into pCR2.1 vector using a TOPO-TA cloning kit (Invitrogen) and multiple clones are sequenced to check for target site sequence changes as the results of non-homologous end joining (NHEJ). The Soy8672.7.1 event was identified as the bi-allelic knockout variants of the HEL1 gene (chromosome 4) with either one base insertion (G) or 4 bp deletion (AGGT). There is no change for the HEL2 gene (chromosome 6) in the Soy8672.7.1 event. The second soy8605.2.1 event was identified as mono-allelic knockout of the HEL1 gene (chromosome 4) with the one base deletion (G), and with the second allele of the HEL1 gene as a WT. In the same SOY8605.2.1 event, the HEL2 gene (chromosome 6) was shown as a bi-allelic knockout as the genomic fragment flanked by the GM-HEL-CR7 and GM-HEL-CR1 was inverted by the double strand break repair process, which resulted in gene knockout of the HEL2 gene (Table 5).

TABLE 5

Soybean edited variants with mutations in HEL1 and HEL2 genes

| Event | HEL1 | HEL2 |
|---|---|---|
| SOY 8672.7.1 | hel1-1, +G at position 4857 in SEQ ID NO: 6 | WT |
| | hel1-2, −AGGT at position corresponding to 4854-4857 in SEQ ID NO: 5, shown in SEQ ID NO: 7 | WT |
| SOY8605.2.1 | hel1-3, −G at position corresponding to 4856 in SEQ ID NO: 5, shown in SEQ ID NO: 8 | hel2, inverted at position 1899-2799 in SEQ ID NO 10 |

Example 2. Increasing Protein Content in Seed by Knockout of HEL1 and/or HEL2

Figure 2:
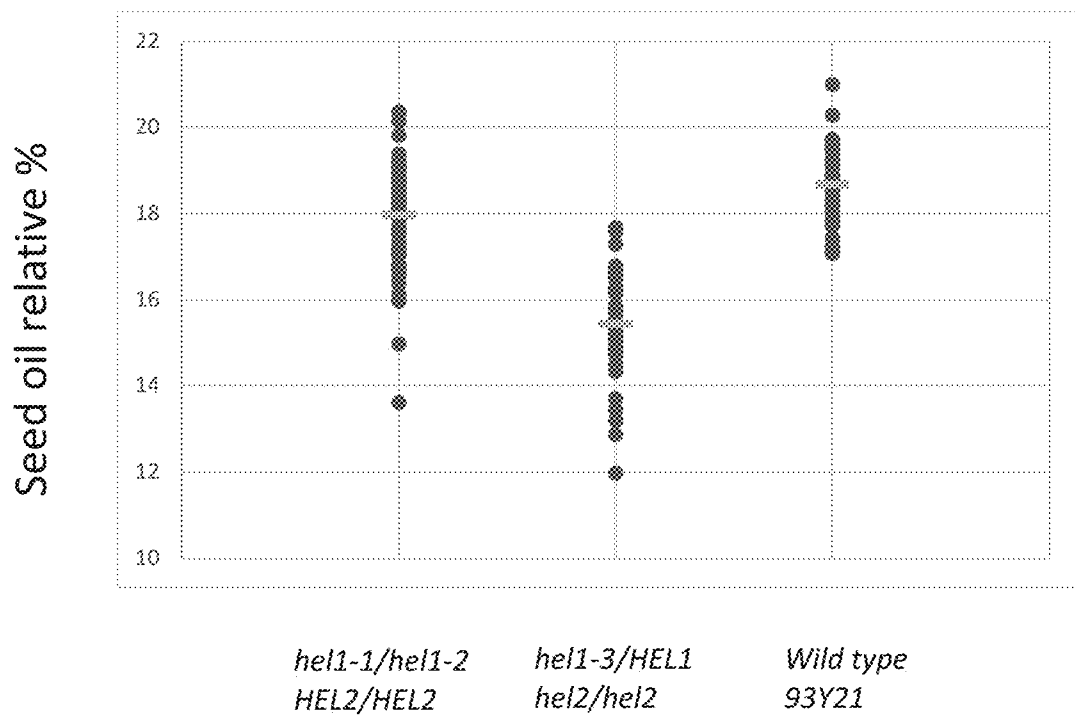
FIG. 2 is graph showing the T1 seed oil content of hel1 and hel2 knockout variants. hel1-1/hel1-2 is homozygous knockout of HEL1 gene; HEL2/HEL2 is wild type of HEL2 gene; hel1-3/HEL1 is heterozygous knockout of HEL1 gene; hel2/hel2 is homozygous knockout of HEL2 gene. Each dot represents an individual T1 seed. The bar is the average seed oil content; values are given as relative percent oil estimates from NIR analysis.

TO plants were selfed to obtain T1 seeds. Single T1 seed oil and protein content were determined by SS-NIR as described previously (Roesler et al Plant Physiol. 2016 878-893). Knockout of HEL1 gene increased seed protein content significantly compared to wild type 93Y21. Knockout of both HEL1 and HEL2 showed a higher protein content than HEL1 knockout or wild type (FIG. 1). In contrast, knockout of HEL1 reduced seed oil content slightly while knockout of both HEL1 and HEL2 reduced seed oil content by 17.6% (FIG. 2).

In addition to protein and oil, knockout of HEL1 increased oleic and stearic contents, and reduced linolenic, palmitic and stachyose contents. (Tables 6 and 7). Knockout of both HEL1 and HEL2 increased oleic content and reduced linoleic, linolenic, palmitic, stearic, stachyose, and total soluble carbohydrate contents. Knockout of either HEL1 or both HEL1 and HEL2 did not affect seed weight.

TABLE 6

Fatty acid profile of HEL1 and HEL2 knockout variants in T1 seeds

| T0 plant genotype | Oleic % (18:1) | Linoleic % (18:2) | Linolenic % (18:3) | Palmitic % (16:0) | Stearic % (18:0) |
|---|---|---|---|---|---|
| hel1/HEL1; HEL2/HEL2 | 14.9* | 54.2 | 8.5* | 13.2* | 4.6* |
| hel1/HEL1; hel2/hel2 | 35.1* | 38.1* | 8.9* | 11.4* | 3.9* |
| Wild type 93Y21 | 12.3 | 54.1 | 10.4 | 14.0 | 4.1 |

note:
hel1-1/hel1-2 is homozygous knockout of HEL1 gene; HEL2/HEL2 is wild type of HEL2 gene; hel1-3/HEL1 is heterozygous

TABLE 7

Carbohydrate profile/seed weight of HEL1 and HEL2 knockout variants in T1 seeds

| T0 plant genotype | Stachyose % | Total Carb % | Sucrose % | Seed weight (g) |
|---|---|---|---|---|
| hel1/HEL1; HEL2/HEL2 | 4.9* | 9.4 | 4.4 | 0.25 |
| hel1/HEL1; hel2/hel2 | 3.9* | 6.8* | 4.0 | 0.26 |
| Wild type 93Y21 | 5.5 | 9.1 | 4.4 | 0.24 |

note:
hel1-1/hel1-2 is homozygous knockout of HEL1 gene; HEL2/HEL2 is wild type of HEL2 gene; hel1-3/HEL1 is heterozygous T1 plants were genotyped by sequencing mutations in HEL1 and HEL2 genes. Bulk T2 seeds composition were determined by FTNIR. Homozygous mutants of both HEL1 and HEL2 show an increased protein content by 3.1 percentage points and a reduction in oil content of 1.1 percentage points compared to wild type 93Y21 (Table 8). Individual homozygous mutants of HEL1 or HEL2 showed a smaller increase in protein than the homozygous double mutant.

TABLE 8

T2 seed protein and oil content of HEL1 and HEL2 mutants

| HEL1 | HEL2 | FTNIR Oil13% | FTNIR Protein13% | FTNIR C181 |
|---|---|---|---|---|
| WT | WT | 21.3 | 31.7 | 13.5 |
| HOM | WT | 21.2 | 32.6 | 15.1 |
| WT | HOM | 20.2 | 32.3 | 20.4 |
| HET | HOM | 20.1 | 33.2 | 19.0 |
| HOM | HOM | 20.2 | 34.8 | 26.7 |

Example 3. Identification of HEL1 and HEL2 Mutants from Mutagenized Populations

Soybean mutagenized populations will be generated by gamma-ray irradiation, fast neutron irradiation, chemical treatment with EMS (ethyl methanesulfonate) or ENU (N-ethyl-N-nitrosourea). Treatment of soybean seeds with 60 mM EMS can induce 5000-10000 mutations in a M2 plant. Each M2 plant will be sequenced by whole genome sequencing. Compared to the wild type reference genome, mutations in a M2 plant will be detected and mapped to the genome. By sequencing about 2000-5000 M2 lines, mutations for most to all genes in the soybean genome will be detected. Once a M2 line containing a mutation in HEL1 gene or HEL2 gene is identified, the plant will be backcrossed to wild type soybean to remove mutations are not related to HEL1 or HEL2 gene. The resultant HEL1 mutant plants can be crossed to HEL2 mutant plants to generate double mutants which are expected to have increased seed protein content.

What is claimed is:

1. A soybean plant comprising an altered seed composition and a modification that results in decreased expression or activity of at least two HECT E3 ligase polypeptides, the plant comprising a modification selected from a deletion, insertion or substitution of nucleotides in at least two genomic sequences comprising at least two polynucleotides encoding at least two HECT E3 ligase polypeptides, the at least two HECT E3 ligase polypeptides comprising (i) an amino acid sequence that is at least 95% identical to SEQ ID NO: 2, and (ii) an amino acid sequence that is at least 95% identical to SEQ ID NO: 4, the modification resulting in suppression of the activity of the at least two HECT E3 ligase polypeptides, wherein the plant produces a seed comprising at least two characteristics relative to that of a control seed not comprising the modification, the characteristics selected from: (a) fatty acids with increased oleic acid content, (b) fatty acids with decreased linoleic acid content; (c) fatty acids with decreased linolenic acid content; (d) fatty acids with decreased stearic acid content; (e) fatty acids with decreased palmitic acid content; (f) a reduced soluble carbohydrate content, and (g) an increased protein content.

2. The plant of claim 1, wherein the oleic acid content in the seed is increased by at least 5% relative to control seeds not comprising the modification.

3. The plant of claim 1, wherein the stachyose content is reduced by at least 5% relative to the control seeds not comprising the modification.

4. The plant of claim 1, wherein the plant further comprises a modified DGAT sequence.

5. The plant of claim 2 wherein the plant produces seeds having an increased protein content of at least 2% relative to the control seeds not comprising the modification.

6. The plant of claim 1, wherein the modification comprises a deletion, insertion or substitution of nucleotides in a first genomic sequence encoding a polypeptide comprising an amino acid sequence that is at least 95% identical to SEQ ID NO: 2 and a deletion, insertion or substitution of nucleotides in a second genomic sequence encoding a polypeptide comprising an amino acid sequence that is at least 95% identical to SEQ ID NO: 4.

7. The plant of claim 1, wherein the modification comprises a deletion, insertion or substitution in a transcription regulatory region of the genomic sequence.

8. The plant of claim 1, further comprising a heterologous nucleic acid sequence selected from the group consisting of: a reporter gene, a selection marker, a disease resistance gene, a herbicide resistance gene, an insect resistance gene; a gene involved in carbohydrate metabolism, a gene involved in fatty acid metabolism, a gene involved in amino acid metabolism, a gene involved in plant development, a gene involved in plant growth regulation, a gene involved in yield improvement, a gene involved in drought resistance, a gene involved in increasing nutrient utilization efficiency, a gene involved in cold resistance, a gene involved in heat resistance and a gene involved in salt resistance in plants.

9. A method for altering the composition of a seed of a soybean plant, the method comprising:

a. introducing a modification into at least two HECT E3 ligase genes in a soybean plant, wherein the modification comprises a deletion, insertion or substitution of nucleotides in (i) a first genomic sequence comprising a sequence encoding a HECT E3 ligase polypeptide comprising an amino acid sequence that is at least 95% identical to SEQ ID NO: 2, and (ii) a second genomic sequence comprising a sequence encoding a HECT E3 ligase polypeptide comprising an amino acid sequence that is at least 95% identical to SEQ ID NO: 4 to produce a modified plant; and b. growing the modified plant to produce a modified seed, wherein the modified seed comprises at least two altered characteristics relative to that of a control seed not comprising the modification, the characteristics selected from: (a) fatty acids with increased oleic acid content, (b) fatty acids with decreased linoleic acid content; (c) fatty acids with decreased linolenic acid content; (d) fatty acids with decreased stearic acid content; (e) fatty acids with decreased palmitic acid content; (f) a reduced soluble carbohydrate content, and (g) an increased protein content.

10. The method of claim 9, wherein the modified seed has an at least 5% increased oleic acid content relative to control seeds not comprising the modification.

11. The method of claim 10, wherein the modified seed has an increased protein content relative to the control seed not comprising the modification.

12. The method of claim 9, wherein the modified seed comprises a sucrose content decreased by at least 5% relative to the control seed not comprising the modification.

13. The method of claim 9, wherein the modified seed comprises a linoleic acid content is decreased by at least 5% relative to the control seed not comprising the modification.

14. The method of claim 9, wherein the modified seed comprises a stearic acid content decreased by at least 5% relative to the control seeds not comprising the modification.

15. The method of claim 9, wherein the introducing of a modification in step (a) comprises introducing a deletion or insertion through targeted DNA breaks.

16. The method of claim 9, the method further comprising crossing a plant grown from the modified seed with a second different plant and harvesting the progeny seed.

17. A method of advancing a soybean plant in a plant breeding program, the method comprising:

a. contacting a DNA sample obtained from the soybean plant of claim 1 with a first and a second primer molecule, wherein (i) the first primer molecule binds to a region upstream of or including a first modification in SEQ ID NO: 5 and the second primer molecule binds to a genomic region downstream of or including the modification in SEQ ID NO: 5, and a third and a fourth primer molecule, wherein (ii) the third primer molecule binds to a region upstream of or including a second modification in SEQ ID NO: 9 and the fourth primer molecule binds to a genomic region downstream of or including the modification in SEQ ID NO: 9;

b. providing a nucleic acid amplification reaction condition;

c. performing the nucleic acid amplification reaction, thereby producing at least two DNA amplicon molecules indicating the presence of polynucleotides comprising the first modification and the second modification; and d. detecting the DNA amplicon molecules, thereby advancing the plant in the plant breeding program.

18. The method of claim 17, wherein the DNA amplicon molecule produced in step (c) is at least 48 and less than 5000 nucleotides in length.

19. The method of claim 17, wherein the plant comprising the modified polynucleotide produces a seed having fatty acids with increased oleic acid content and an increased protein content.

20. The method of claim 17, further comprising selfing the soybean plant or crossing the soybean plant with a second plant to produce progeny seed.

* * * * *

SEQUENCE LISTING

```
<160> NUMBER OF SEQ ID NOS: 16

<210> SEQ ID NO 1
<211> LENGTH: 5676
<212> TYPE: DNA
<213> ORGANISM: Glycine max

<400> SEQUENCE: 1

atggaaactc ggagtcggaa gcgggcggag gcttcctcag ctgccccttc atcctcgtcc     60

accacccctt ctcgttcagc caagcgctct cgtctttctt cttcttcttc ttccatccta    120

cctgttaata cacgttctcg ttccgccagg aataacaaca acaacaacaa ctccggttcc    180

atttctttca tggaccccac caatgaatcc tccgggtccc gacgtgatcg ccgtggcaag    240

aatttcgata gggaaaattc ggacaaaggg aaggagaagg aacaggatgt taggattagg    300

gatgcggagc gggagcgaga gcgagccttg gcgttaaaca tggagagtga agatgttggg    360

gatgacgatg ataatgatag tgacggcggt gtgggaattc tgcaccagaa tttgacgtct    420

gccagtagtg ccccttcaagg gcttcttcgg aaacttggtg ctggtttgga tgatttgctt    480

cctgctactg ctatgggcgg ttctgcgtca tctcctcatc agagtggcag actcaagaag    540

attttgtctg gcttgcgtgc cgatggggaa gaaggtcgtc aggttgaggc attgacgcag    600

ctttgtgaca tgctctccat tggcactgaa gattccctca gcacattttc ggttgactca    660

tttgttcctg tgctagtggg cttgcttaat cacgagagca atcccgatgt catgcttctt    720

gcggccaggg cgctaaccca tttatgtgat gtgcttcctt catcctgtgc tgctgttgtg    780

cattatggtg ctgtctctat cttctgtgcg aggctgctca ccatagagta tatggacttg    840

gctgagcagt ctcttcaagc actaaagaag atttctcagg agcacccaac tgcctgtctt    900

agagctggag ctctgatggc tgttctttct tacttggact tcttctcaac aggagttcag    960

cgggtggcat tgtctactgc tgcaaatatg tgcaagaagc ttcctcctga tgcagctgac   1020

tttgtgatgg aagctgttcc acttttgaca aacctccttc agtaccacga ctccaaggtc   1080

ctggaacatg cctctgtttg tttgacacga atagctgaag catttgcatc atctccagac   1140

aaattagatg aattgtgcaa tcatggactg gtaacacaag ctgcctctct catttctacc   1200

agcagttctg gaggtgggca ggcttctctc agcactccaa catatactgg tttgatccgc   1260
```

```
cttctttcca catgtgcaag tgggtctcct cttggagcta aaacgttgct tctccttgga   1320
actagtggca ttcttaaaga tatactatcc ggttccggtg tttcttctaa cacctctgtt   1380
tcgcctgcat tgagtaggcc agcggatcag atatttgaga ttgtgaacct ggcaaatgaa   1440
cttctgcctc cattgcctca aggaaccatt tcccttcctg tcagctccaa cttgtttgtg   1500
aaagggtctg ttgtgaaaaa atcctcttct ggcaattctg ggatacaaga agacacaaat   1560
ggaaatgttc atgagatatt ggctcgtgag aaattattaa atgatcagcc tgagttactt   1620
cagcaatttg ggatggatct cctcccagtt ttaatgcaga tatatggtgc tagcgtcaat   1680
ggtccagttc ggcacaaatg tctttctgtc attggaaaat tgatgtattt cagcacagct   1740
gagatgatcc agtctttact gagtgtaaca aatatatcaa gtttcttagc tggtgtgtta   1800
gcatggaaag atccacatgt tttggttcct gccttgcaaa tttcggaaat tcttatggaa   1860
aagcttcctg gaaccttctc taagatgttt gtcagagaag gtgtggttca tgcagttgac   1920
caacttattt tggctggaaa ttcaaccaat atatccacac aaacatcatc tgctgagaag   1980
gataatgatt ctgtatctgg aacttcatct cgctctagac gctatcgcct gcgcagtggt   2040
aattcaaatc ccgatgcgaa cccttcagat gatttaaaga gtccagttcc agtaaatgtt   2100
ggtttgccac caagttctgt agaaactcca acaactaatt ctagtatccg tgcatctgtt   2160
agctcagttg ctagagcttt taaagacaag tactttcctt ctgatcctgg gtctgttgaa   2220
gtgggtgtta gtgatgatct tttgcatctg aaaaatctat gcacgaagtt gatcactggt   2280
gttgatgacc aaagaagcaa ggcaaaggga aaagttaaag cttctggatt tggtctggat   2340
gataattcta gtaacacaga agagtatttg attggggtga tatctgacat gctaaaggaa   2400
cttggcaaag gagatagtgt atctactttt gaatttatcg gtagtggtgt tgttgaagcc   2460
ttgctaaatt atttttcttg tgggtatttc tctaaagatc gaatatcaga aaccaatctc   2520
cccaagcttc gccaacaggc actttcaagg ttcaagtcat ttgtagctgt tgcactacct   2580
ttgagcattg acaatggggc tgttgctcct atgactgtct tagttcagaa gcttcaaaat   2640
gcgttggcct ccttggagcg tttccctgtt atgctgagta attcatctcg gtcatctagt   2700
ggaagtgcac gtctctcctc tgggctaagt gcattatctc agcccataaa attacgtctc   2760
tgccgagccc agggtgaaaa gtcacttagg gattattcat ccaatgtggt actgattgat   2820
ccattagcaa gtctagcagc catcgaggaa tttctatggg ctcgtgtcca gcgtggtgaa   2880
tctggtcaga agtctactgt aggcactgaa aattctgaat ctggaacaac tcctgctggg   2940
gcaggtgttt catctccttc ctcttatact ccctccactg cccatcgtca ttctactaga   3000
accagatcat ctgttaatat aggagataca cctagaaaag aaacatctca agacaaagga   3060
acgagctcat caaagagcaa gggtaaagct gtattaaaac ctgcgcagga ggaagcgcaa   3120
ggaccccaaa caaggaatac agtgcgcaga agagcagctc ttgataaagt cgctcaaatg   3180
aaacctgcaa atggcgactc aacttctgag gatgaagaat tggatatatc tcctgttgaa   3240
attgctgagg ctttggtgat tgaagatgat gatatttctg atgatgagga tgaagaccat   3300
gaagatgtgc tgagggatga ttctcttcct gtctgcttgc ctgacaaagt gcatgatgtg   3360
aaattgggtg actcagctga ggagagtact gttgctccag caacaagtga tagccagact   3420
aatgcagcct caggttcaag cagcaaagct ggtacagcca ggggttctga ctccgctgat   3480
tttaggagtg ggttttcatc tagctcaagg ggtgcaatgt catttgctgc tgctgctatg   3540
gctggacttg gatatgctaa tagcagaggt ttcaggggcg gcagagatag gcatgggtgc   3600
```

-continued

```
ctgttgtttg gtagttctaa tgatcctccg aagttgattt ttactactgg tgggaagcag   3660
cttaatagga atctgagtat atatcaggca attcaaagac agcttgtgct agatgaagat   3720
gatgatgaga gatttgctgg cagtgactat gtatctggtg atggaagcag tctgtggggt   3780
gatatttaca ccatcactta tcaaagggca gaaaaccagc cagataaggc gtctactgga   3840
ggatcaagtt caaatacttc aaaatctgcc aaatctgggt ctgccttaaa ttcaagctca   3900
gaagctaaat tgcatcagac atctgttcta gacagtatat tgcagggaga attgccatgt   3960
gatctagaga aatctaatcc cacctacaat attttggcac tcctgcgtgt gctggagggt   4020
ttcaaccaac ttgcgcctcg tttgagggtc ctaatggttt ctgatagctt tgccaaggga   4080
aaaatcttgg atttagatga gctatgtgtt acaactggtg ctagggtgct tctagaggaa   4140
tttgtaagtg gtaagcttac tccaaaattg gctaggcaaa tacaagatgc ccttgcacta   4200
tgcagtggta atcttccctt atggtgttac cagttgacta aagcgtgccc tttcttgttt   4260
ccttttgaga cccgacgaca gtacttttat tctaccgcat ttgggttatc tcgtgcactg   4320
tatcgacttc aacagcagca aggtgctgat ggccatggtt caacaactga gagggaggtg   4380
agagttggga gattgcagcg ccaaaaggtt cgtgtctctc gaaatcgtgt cctggattct   4440
gctgcaaaag ttatggagat gtattctagc caaaaagctg tacttgaagt agaatatttt   4500
ggtgaagttg gcactggtct gggtcccacc cttgagtttt atacaattct aagtcatgat   4560
ttgcaaaaag ttggactgca aatgtggaga tcttattctt cagacaaaca tcaaatggaa   4620
atagatggag atgaaaagaa aaagaaaagt gaaggctctg ggcctaattt ggctggagat   4680
ggagaacttg ttcaagctcc tctggggttg tttcctcggc catggcctac aaattctgat   4740
gcttcagaga gtagccagtt ttcaaaagtc attgagtatt tccggctact aggtcgtgtt   4800
atggctaaag ctcttcaaga cggacgacta ctggacctgc cattgtcagt ggcattttat   4860
aagcttgttc tctgccaaga tcttgatttg catgacattc tgttcattga tgctgagctt   4920
gggaagactt tacaagagtt caatgccctt gtttgtcgga aacattatat agaatctatt   4980
ggtggtagct atacagatac aattgttaac ttgtattttc atggtgcacc aatcgaagat   5040
ctttgcttag attttactct ccctggttat cctgaataca ccttgaagcc aggagatgaa   5100
attgttgata tcaacaattt ggaggagtat atatccttgg tgatcgatgc aactgtcaag   5160
actggaatca tgcggcaaat agaagcattt agagcagggt ttaaccaggt ttttgatatc   5220
tcatctttac aaatttttac tcctcaagaa ctagataatt tgctttgcgg ccgcagggag   5280
ttgtgggagg ctgagacact tgctgatcat ataaaattcg accatgggta caatgcaaag   5340
agccctgcca ttgttaattt acttgaaatt atgggagagt tcacaccaga gcagcaacgt   5400
gccttctgtc aatttgttac tggtgcacct aggctgccac ctggagggct ggcagttcta   5460
aatccaaaac taacgattgt gaggaagctt tcgtcaactg cagttaataa ttcatctaat   5520
gggaatggac cttcagaatc agcagatgat gacttgccta gtgtgatgac atgtgctaat   5580
tacctgaaac ttcctcctta ctctaccaag gaaattatgt acaagaagtt gctctatgca   5640
atcagtgagg gccagggatc ctttgattta tcatga                             5676
```

<210> SEQ ID NO 2
<211> LENGTH: 1891
<212> TYPE: PRT
<213> ORGANISM: Glycine max

<400> SEQUENCE: 2

Met Glu Thr Arg Ser Arg Lys Arg Ala Glu Ala Ser Ser Ala Ala Pro

-continued

```
1               5                   10                  15

Ser Ser Ser Ser Thr Thr Pro Ser Arg Ser Ala Lys Arg Ser Arg Leu
            20                  25                  30

Ser Ser Ser Ser Ser Ser Ile Leu Pro Val Asn Thr Arg Ser Arg Ser
        35                  40                  45

Ala Arg Asn Asn Asn Asn Asn Asn Asn Ser Gly Ser Ile Ser Phe Met
    50                  55                  60

Asp Pro Thr Asn Glu Ser Ser Gly Ser Arg Arg Asp Arg Arg Gly Lys
65                  70                  75                  80

Asn Phe Asp Arg Glu Asn Ser Asp Lys Gly Lys Glu Lys Glu Gln Asp
                85                  90                  95

Val Arg Ile Arg Asp Ala Glu Arg Glu Arg Glu Arg Ala Leu Ala Leu
            100                 105                 110

Asn Met Glu Ser Glu Asp Val Gly Asp Asp Asp Asp Asn Asp Ser Asp
        115                 120                 125

Gly Gly Val Gly Ile Leu His Gln Asn Leu Thr Ser Ala Ser Ser Ala
    130                 135                 140

Leu Gln Gly Leu Leu Arg Lys Leu Gly Ala Gly Leu Asp Asp Leu Leu
145                 150                 155                 160

Pro Ala Thr Ala Met Gly Gly Ser Ala Ser Ser Pro His Gln Ser Gly
                165                 170                 175

Arg Leu Lys Lys Ile Leu Ser Gly Leu Arg Ala Asp Gly Glu Glu Gly
            180                 185                 190

Arg Gln Val Glu Ala Leu Thr Gln Leu Cys Asp Met Leu Ser Ile Gly
        195                 200                 205

Thr Glu Asp Ser Leu Ser Thr Phe Ser Val Asp Ser Phe Val Pro Val
    210                 215                 220

Leu Val Gly Leu Leu Asn His Glu Ser Asn Pro Asp Val Met Leu Leu
225                 230                 235                 240

Ala Ala Arg Ala Leu Thr His Leu Cys Asp Val Leu Pro Ser Ser Cys
                245                 250                 255

Ala Ala Val Val His Tyr Gly Ala Val Ser Ile Phe Cys Ala Arg Leu
            260                 265                 270

Leu Thr Ile Glu Tyr Met Asp Leu Ala Glu Gln Ser Leu Gln Ala Leu
        275                 280                 285

Lys Lys Ile Ser Gln Glu His Pro Thr Ala Cys Leu Arg Ala Gly Ala
    290                 295                 300

Leu Met Ala Val Leu Ser Tyr Leu Asp Phe Phe Ser Thr Gly Val Gln
305                 310                 315                 320

Arg Val Ala Leu Ser Thr Ala Ala Asn Met Cys Lys Lys Leu Pro Pro
                325                 330                 335

Asp Ala Ala Asp Phe Val Met Glu Ala Val Pro Leu Leu Thr Asn Leu
            340                 345                 350

Leu Gln Tyr His Asp Ser Lys Val Leu Glu His Ala Ser Val Cys Leu
        355                 360                 365

Thr Arg Ile Ala Glu Ala Phe Ala Ser Ser Pro Asp Lys Leu Asp Glu
    370                 375                 380

Leu Cys Asn His Gly Leu Val Thr Gln Ala Ala Ser Leu Ile Ser Thr
385                 390                 395                 400

Ser Ser Ser Gly Gly Gly Gln Ala Ser Leu Ser Thr Pro Thr Tyr Thr
                405                 410                 415

Gly Leu Ile Arg Leu Leu Ser Thr Cys Ala Ser Gly Ser Pro Leu Gly
            420                 425                 430
```

-continued

```
Ala Lys Thr Leu Leu Leu Leu Gly Thr Ser Gly Ile Leu Lys Asp Ile
        435                 440                 445

Leu Ser Gly Ser Gly Val Ser Ser Asn Thr Ser Val Ser Pro Ala Leu
    450                 455                 460

Ser Arg Pro Ala Asp Gln Ile Phe Glu Ile Val Asn Leu Ala Asn Glu
465                 470                 475                 480

Leu Leu Pro Pro Leu Pro Gln Gly Thr Ile Ser Leu Pro Val Ser Ser
                485                 490                 495

Asn Leu Phe Val Lys Gly Ser Val Val Lys Lys Ser Ser Ser Gly Asn
            500                 505                 510

Ser Gly Ile Gln Glu Asp Thr Asn Gly Asn Val His Glu Ile Leu Ala
        515                 520                 525

Arg Glu Lys Leu Leu Asn Asp Gln Pro Glu Leu Leu Gln Gln Phe Gly
    530                 535                 540

Met Asp Leu Leu Pro Val Leu Met Gln Ile Tyr Gly Ala Ser Val Asn
545                 550                 555                 560

Gly Pro Val Arg His Lys Cys Leu Ser Val Ile Gly Lys Leu Met Tyr
                565                 570                 575

Phe Ser Thr Ala Glu Met Ile Gln Ser Leu Leu Ser Val Thr Asn Ile
            580                 585                 590

Ser Ser Phe Leu Ala Gly Val Leu Ala Trp Lys Asp Pro His Val Leu
        595                 600                 605

Val Pro Ala Leu Gln Ile Ser Glu Ile Leu Met Glu Lys Leu Pro Gly
    610                 615                 620

Thr Phe Ser Lys Met Phe Val Arg Glu Gly Val Val His Ala Val Asp
625                 630                 635                 640

Gln Leu Ile Leu Ala Gly Asn Ser Thr Asn Ile Ser Thr Gln Thr Ser
                645                 650                 655

Ser Ala Glu Lys Asp Asn Asp Ser Val Ser Gly Thr Ser Ser Arg Ser
            660                 665                 670

Arg Arg Tyr Arg Leu Arg Ser Gly Asn Ser Asn Pro Asp Ala Asn Pro
        675                 680                 685

Ser Asp Asp Leu Lys Ser Pro Val Pro Val Asn Val Gly Leu Pro Pro
    690                 695                 700

Ser Ser Val Glu Thr Pro Thr Thr Asn Ser Ser Ile Arg Ala Ser Val
705                 710                 715                 720

Ser Ser Val Ala Arg Ala Phe Lys Asp Lys Tyr Phe Pro Ser Asp Pro
                725                 730                 735

Gly Ser Val Glu Val Gly Val Ser Asp Asp Leu Leu His Leu Lys Asn
            740                 745                 750

Leu Cys Thr Lys Leu Ile Thr Gly Val Asp Asp Gln Arg Ser Lys Ala
        755                 760                 765

Lys Gly Lys Val Lys Ala Ser Gly Phe Gly Leu Asp Asp Asn Ser Ser
    770                 775                 780

Asn Thr Glu Glu Tyr Leu Ile Gly Val Ile Ser Asp Met Leu Lys Glu
785                 790                 795                 800

Leu Gly Lys Gly Asp Ser Val Ser Thr Phe Glu Phe Ile Gly Ser Gly
                805                 810                 815

Val Val Glu Ala Leu Leu Asn Tyr Phe Ser Cys Gly Tyr Phe Ser Lys
            820                 825                 830

Asp Arg Ile Ser Glu Thr Asn Leu Pro Lys Leu Arg Gln Gln Ala Leu
        835                 840                 845
```

```
Ser Arg Phe Lys Ser Phe Val Ala Val Ala Leu Pro Leu Ser Ile Asp
    850                 855                 860

Asn Gly Ala Val Ala Pro Met Thr Val Leu Val Gln Lys Leu Gln Asn
865                 870                 875                 880

Ala Leu Ala Ser Leu Glu Arg Phe Pro Val Met Leu Ser Asn Ser Ser
                885                 890                 895

Arg Ser Ser Ser Gly Ser Ala Arg Leu Ser Ser Gly Leu Ser Ala Leu
            900                 905                 910

Ser Gln Pro Ile Lys Leu Arg Leu Cys Arg Ala Gln Gly Glu Lys Ser
        915                 920                 925

Leu Arg Asp Tyr Ser Ser Asn Val Val Leu Ile Asp Pro Leu Ala Ser
    930                 935                 940

Leu Ala Ala Ile Glu Glu Phe Leu Trp Ala Arg Val Gln Arg Gly Glu
945                 950                 955                 960

Ser Gly Gln Lys Ser Thr Val Gly Thr Glu Asn Ser Glu Ser Gly Thr
                965                 970                 975

Thr Pro Ala Gly Ala Gly Val Ser Ser Pro Ser Ser Tyr Thr Pro Ser
            980                 985                 990

Thr Ala His Arg His Ser Thr Arg  Thr Arg Ser Ser Val  Asn Ile Gly
        995                 1000                1005

Asp Thr  Pro Arg Lys Glu Thr  Ser Gln Asp Lys Gly  Thr Ser Ser
    1010                1015                1020

Ser Lys  Ser Lys Gly Lys Ala  Val Leu Lys Pro Ala  Gln Glu Glu
    1025                1030                1035

Ala Gln  Gly Pro Gln Thr Arg  Asn Thr Val Arg Arg  Arg Ala Ala
    1040                1045                1050

Leu Asp  Lys Val Ala Gln Met  Lys Pro Ala Asn Gly  Asp Ser Thr
    1055                1060                1065

Ser Glu  Asp Glu Glu Leu Asp  Ile Ser Pro Val Glu  Ile Ala Glu
    1070                1075                1080

Ala Leu  Val Ile Glu Asp Asp  Asp Ile Ser Asp Asp  Glu Asp Glu
    1085                1090                1095

Asp His  Glu Asp Val Leu Arg  Asp Asp Ser Leu Pro  Val Cys Leu
    1100                1105                1110

Pro Asp  Lys Val His Asp Val  Lys Leu Gly Asp Ser  Ala Glu Glu
    1115                1120                1125

Ser Thr  Val Ala Pro Ala Thr  Ser Asp Ser Gln Thr  Asn Ala Ala
    1130                1135                1140

Ser Gly  Ser Ser Ser Lys Ala  Gly Thr Ala Arg Gly  Ser Asp Ser
    1145                1150                1155

Ala Asp  Phe Arg Ser Gly Phe  Ser Ser Ser Ser Arg  Gly Ala Met
    1160                1165                1170

Ser Phe  Ala Ala Ala Ala Met  Ala Gly Leu Gly Tyr  Ala Asn Ser
    1175                1180                1185

Arg Gly  Phe Arg Gly Gly Arg  Asp Arg His Gly Cys  Leu Leu Phe
    1190                1195                1200

Gly Ser  Ser Asn Asp Pro Pro  Lys Leu Ile Phe Thr  Thr Gly Gly
    1205                1210                1215

Lys Gln  Leu Asn Arg Asn Leu  Ser Ile Tyr Gln Ala  Ile Gln Arg
    1220                1225                1230

Gln Leu  Val Leu Asp Glu Asp  Asp Asp Glu Arg Phe  Ala Gly Ser
    1235                1240                1245

Asp Tyr  Val Ser Gly Asp Gly  Ser Ser Leu Trp Gly  Asp Ile Tyr
```

```
    1250                1255                1260

Thr Ile  Thr Tyr Gln Arg Ala  Glu Asn Gln Pro Asp  Lys Ala Ser
    1265                1270                1275

Thr Gly  Gly Ser Ser Ser Asn  Thr Ser Lys Ser Ala  Lys Ser Gly
    1280                1285                1290

Ser Ala  Leu Asn Ser Ser Ser  Glu Ala Lys Leu His  Gln Thr Ser
    1295                1300                1305

Val Leu  Asp Ser Ile Leu Gln  Gly Glu Leu Pro Cys  Asp Leu Glu
    1310                1315                1320

Lys Ser  Asn Pro Thr Tyr Asn  Ile Leu Ala Leu Leu  Arg Val Leu
    1325                1330                1335

Glu Gly  Phe Asn Gln Leu Ala  Pro Arg Leu Arg Val  Leu Met Val
    1340                1345                1350

Ser Asp  Ser Phe Ala Lys Gly  Lys Ile Leu Asp Leu  Asp Glu Leu
    1355                1360                1365

Cys Val  Thr Thr Gly Ala Arg  Val Leu Leu Glu Glu  Phe Val Ser
    1370                1375                1380

Gly Lys  Leu Thr Pro Lys Leu  Ala Arg Gln Ile Gln  Asp Ala Leu
    1385                1390                1395

Ala Leu  Cys Ser Gly Asn Leu  Pro Leu Trp Cys Tyr  Gln Leu Thr
    1400                1405                1410

Lys Ala  Cys Pro Phe Leu Phe  Pro Phe Glu Thr Arg  Arg Gln Tyr
    1415                1420                1425

Phe Tyr  Ser Thr Ala Phe Gly  Leu Ser Arg Ala Leu  Tyr Arg Leu
    1430                1435                1440

Gln Gln  Gln Gln Gly Ala Asp  Gly His Gly Ser Thr  Thr Glu Arg
    1445                1450                1455

Glu Val  Arg Val Gly Arg Leu  Gln Arg Gln Lys Val  Arg Val Ser
    1460                1465                1470

Arg Asn  Arg Val Leu Asp Ser  Ala Ala Lys Val Met  Glu Met Tyr
    1475                1480                1485

Ser Ser  Gln Lys Ala Val Leu  Glu Val Glu Tyr Phe  Gly Glu Val
    1490                1495                1500

Gly Thr  Gly Leu Gly Pro Thr  Leu Glu Phe Tyr Thr  Ile Leu Ser
    1505                1510                1515

His Asp  Leu Gln Lys Val Gly  Leu Gln Met Trp Arg  Ser Tyr Ser
    1520                1525                1530

Ser Asp  Lys His Gln Met Glu  Ile Asp Gly Asp Glu  Lys Lys Lys
    1535                1540                1545

Lys Ser  Glu Gly Ser Gly Pro  Asn Leu Ala Gly Asp  Gly Glu Leu
    1550                1555                1560

Val Gln  Ala Pro Leu Gly Leu  Phe Pro Arg Pro Trp  Pro Thr Asn
    1565                1570                1575

Ser Asp  Ala Ser Glu Ser Ser  Gln Phe Ser Lys Val  Ile Glu Tyr
    1580                1585                1590

Phe Arg  Leu Leu Gly Arg Val  Met Ala Lys Ala Leu  Gln Asp Gly
    1595                1600                1605

Arg Leu  Leu Asp Leu Pro Leu  Ser Val Ala Phe Tyr  Lys Leu Val
    1610                1615                1620

Leu Cys  Gln Asp Leu Asp Leu  His Asp Ile Leu Phe  Ile Asp Ala
    1625                1630                1635

Glu Leu  Gly Lys Thr Leu Gln  Glu Phe Asn Ala Leu  Val Cys Arg
    1640                1645                1650
```

```
Lys His  Tyr Ile Glu Ser Ile  Gly Gly Ser Tyr Thr  Asp Thr Ile
    1655                 1660                 1665

Val Asn  Leu Tyr Phe His Gly  Ala Pro Ile Glu Asp  Leu Cys Leu
    1670                 1675                 1680

Asp Phe  Thr Leu Pro Gly Tyr  Pro Glu Tyr Thr Leu  Lys Pro Gly
    1685                 1690                 1695

Asp Glu  Ile Val Asp Ile Asn  Asn Leu Glu Glu Tyr  Ile Ser Leu
    1700                 1705                 1710

Val Ile  Asp Ala Thr Val Lys  Thr Gly Ile Met Arg  Gln Ile Glu
    1715                 1720                 1725

Ala Phe  Arg Ala Gly Phe Asn  Gln Val Phe Asp Ile  Ser Ser Leu
    1730                 1735                 1740

Gln Ile  Phe Thr Pro Gln Glu  Leu Asp Asn Leu Leu  Cys Gly Arg
    1745                 1750                 1755

Arg Glu  Leu Trp Glu Ala Glu  Thr Leu Ala Asp His  Ile Lys Phe
    1760                 1765                 1770

Asp His  Gly Tyr Asn Ala Lys  Ser Pro Ala Ile Val  Asn Leu Leu
    1775                 1780                 1785

Glu Ile  Met Gly Glu Phe Thr  Pro Glu Gln Gln Arg  Ala Phe Cys
    1790                 1795                 1800

Gln Phe  Val Thr Gly Ala Pro  Arg Leu Pro Pro Gly  Gly Leu Ala
    1805                 1810                 1815

Val Leu  Asn Pro Lys Leu Thr  Ile Val Arg Lys Leu  Ser Ser Thr
    1820                 1825                 1830

Ala Val  Asn Asn Ser Ser Asn  Gly Asn Gly Pro Ser  Glu Ser Ala
    1835                 1840                 1845

Asp Asp  Asp Leu Pro Ser Val  Met Thr Cys Ala Asn  Tyr Leu Lys
    1850                 1855                 1860

Leu Pro  Pro Tyr Ser Thr Lys  Glu Ile Met Tyr Lys  Lys Leu Leu
    1865                 1870                 1875

Tyr Ala  Ile Ser Glu Gly Gln  Gly Ser Phe Asp Leu  Ser
    1880                 1885                 1890
```

<210> SEQ ID NO 3
<211> LENGTH: 5688
<212> TYPE: DNA
<213> ORGANISM: Glycine max

<400> SEQUENCE: 3

```
atggaaactc gtagtcgtaa gcgggcggag gcttcctcag ctgccccttc atcatcctcg     60

tccaccacca ccaccaccgc ctctcgttcc gccaagtgct ctcgtctttc ttcttcttct    120

tcttccatcc caaacacaac tactgctaat acacgttctc gttccgccag gaacaacaac    180

aacaactccg tttctcccat ggaccccacc aatgaatcct ccggttccag acgtgatcgc    240

cgcggcaaga atttcgatag ggacaattcg gacaaaggga aggagaaaga acatgatgtt    300

aggattaggg atgcggagcg ggagcgagcc ttggcgttga acttggaggc tgaagatgtt    360

ggggatgacg acgatgataa tgatagtgag ggcggtgtcg gaattctgca ccagaatttg    420

atttctgcca gtacctttcg agggcttctt cggaaacttg gtgctggttt ggatgatttg    480

cttcctgcta cggctatggg cggttctgtg ccctcttctc accagactgg cggactcaag    540

cagatattgt ctggtttgcg tgccgatggg gaagaaggtc gtcaggttga ggcattgacg    600

catctttgtg acatgctctc cattggcact gaagattcat taagtacatt ttcggttgat    660
```

```
tcatttgttc ctgtgctagt gggcttgctt aatcatgaga gcaatcccga tgtcatgctt    720
cttgcggcca gggcgctaac ccatttatgt gatgtgcttc cttcatcctg tgctgctgtt    780
gtgcattatg gtgcagtctc tatcttctgt gcgaggctgc ttaccataga gtatatggac    840
ttggctgagc agtctcttca agcactaaag aagatttctc aggagcaccc aactgcctgt    900
cttcgagctg gagctctgat ggctgttctt tcttacttgg acttcttctc gacaggagtt    960
cagcgggtgg cattgtctac tgctgcaaat atgtgcaaga agcttcctcc tgatgcagct   1020
gactttgtga tggaagctgt tccacttttg acaaacctcc ttcagtacca cgactccaag   1080
gtcctggaac atgcctctgt ttgtttgaca cgaatagcta aagcgtttgc atcatctcca   1140
gacaaattag atgaattgtg caatcatgga ctggtaacac aagctgcctc tctcatttct   1200
accagcggtt ctggaggtgg gcaggcttct ctcagcaccc caacatatac tggtttgatc   1260
cgccttcttt ccacatgtgc aagtgggtct cctcttggag ctaaaacgtt gcttctccat   1320
ggagctagtg gcatacttaa agatatacta tccggttccg gtgtttcttc taacacctct   1380
gtttcgcctg cattgagtag gccagcggat cagatatttg agattgtgaa cctggcaaat   1440
gaacttctgc ctccattgcc tcaaggaacc atttctcttc ctgtcagctc caacttgttt   1500
gtgaaagagt ctgttgtgaa aaaatctcct ccttctggga atcccgggat acaagaagac   1560
acaaatggaa atgttcatga aatatcagct cgtgcaaaat tattaaatga taagcctgag   1620
ttacttaagc aatttgggat ggatctcctc ccagttttaa tgcagatata tggtgctagc   1680
gtcaatggtc cagttcggca caaatgtctt tctgtcattg gaaaattgat gtatttcagc   1740
acagctgaga tgatccagtc tttgttgagt gtaacaaata tatcaagttt cttagctggt   1800
gtgttagcat ggaaagatcc acatgttttg gttcctgcct tgcaaatttc agaaattctt   1860
atggaaaagc ttcctggaat tttctctaaa atgtttgtca gagaaggtgt ggttcatgca   1920
gttgaccaac ttattttggc tggaaatgca actaatatat ctacacaaac atcatctgct   1980
gagaaggata ctgattctgt atctggaact tcatctcgct ctagacgcta tcgcctgcgc   2040
agtggtaatt caaatcccga tgcgaaccgt tcggatgatt tgaagagtcc agttccagta   2100
aatgttggtt tgccaccaag ttctgtggaa actccaacaa ctaattctag tatccgtgca   2160
tccattagct cagttgctaa tgcttttaaa gacaagtact ttccttctga tcctgggtct   2220
gttgaagtgg gtgttagtga tgatcttttg catctgaaaa atctatgctc gaagttgaac   2280
actggtgttg atgaccaaag aagtaaggcc aagggaaaag ttgaagcttc tggatttgat   2340
ctggatgatg attctactaa cacagaagag tatttgattg gggtgatatc tgacatgcta   2400
aaggaacttg gcaaaggaga tagtgtatct acttttgaat ttatcggtag tggtgttgtt   2460
gaagccttgc taaattattt ttcttgtggg tatttctcta aagatcgaat atcagaaacc   2520
aatctcccca agcttcgcca acaggcactt acaaggttca agtcatttgt tgctgttgca   2580
ttacctttga gcattgacaa tggggctgtt gctcctatga ctgtcttggt tcagaagctt   2640
caaaatgtgt tgtcctcctt ggagcgtttc cctgtaatgc tgagtaattc atctcggtca   2700
tctagtggaa gtggacgtct ctcctctggg ctaagtgcat tatctcagcc cataaaatta   2760
cgtttctgtc gagcccaggg tgaaaagtca cttaaggatt attcatccag tgtggtactg   2820
attgatccgt tagcaagtct agcagccatc gaggaatttc tatgggctcg tgtccagcgt   2880
ggtgaatctg gtctaaagtc tactgtaggc actgaaaatt ctgaatctgg aacaactcct   2940
gcaggggctg gtgtttcatc tccttcctct tatattccct ccactgcctt tcgttattca   3000
accggatcca gatccagatc atctgttaat ataggagata cacctagaaa agaaatattt   3060
```

```
caagacaatg gcacgagctc atctaagagc aagggtaaag ctgtattaaa acctgcgcag   3120
gaggaagcac ggggacccca aacaaggaat gcagtgcgca gaagagcagc tctagataaa   3180
gacgctcaaa tgaaacctgc aaatggcgac tcaacttctg aggatgaaga attggatata   3240
tctcctgttg aaattgatga ggctttggtg attgaagatg atgatatttc tgatgatgag   3300
gatgaagacc gtgaagatgt acggagggat tattatcttc ctgtctactt gcctgacgaa   3360
gtgcatgatg tgaaattggg tgactcagct gaggagagta ctgttgctcc tgcaacaagt   3420
gatagccaga ctaatgcagc ttcaggttct agcagcaaag cgggtacagc caggggttgt   3480
gactctgctg attttaggag tgggtattca tctagctcaa ggggtgcaat gtcatttgct   3540
gctgctgcta tggctggact tggatatgct aatagcagag gtttcagggg tggcagagat   3600
aggcatgggc gcctgttgtt tggtagttct aatgatcctc caaagttgat ttttactgct   3660
ggtgggaagc atcttaatag gaatttgact atatatcagg caattcaaag acagctcatg   3720
ctagatgaag atgatgatga gagacttgct ggcagtgacc gtgtatctag tgatggaagc   3780
agcctgtggg gtgatattta caccatcact tatcaaaggg cagaaaacca gccagataag   3840
gcatccaatg gtggatcaag ttcaaatact tcaaaatctg ccaaatctgg gtctgcatta   3900
aattccagct cagaagctaa attgcatcag acatctgttc tagacagtat attgcaggga   3960
gacttgccat gtgatctaga gaaatctaat cctacctaca atattttggc actcctgcgt   4020
gtgctggagg gtttgaacca gcttgcgcct catttgagga cccaaatggt ttctgatagc   4080
ttcgccaagg gaaaaatctt ggatttagat gagctaggtg ttacaactgg tgctagggtg   4140
cttccagagg aatttgtgag tggtaagctt actccaaaat tggctaggca aatacaagat   4200
gcccttgcac tatgcagtgg tagtcttccc ttatggtgtt gccagttgac taaagcatgc   4260
cctttcttgt ttccttttga cacccgacga cagtactttt attctaccgc atttgggtta   4320
tctcgtgcat tgtatcgact tcagcagcag caaggcgctg atggtcatgg atcaacaact   4380
gagagggagg tgagagttgg gagattgcag cgccaaaagg ttcgtgtctc tcgaaatcgt   4440
gtcttggatt ctgctgcaaa agttatgggg atgtattcta gccaaaaagc tgtacttgaa   4500
gtagaatatt ttggtgaagt tgggactggc ctgggtccca cccttgagtt ttatacaatt   4560
ctaagtcatg atttgcaaca agttggattg caaatgtgga gatcttattc ttcagaaaaa   4620
catcaaatgg aaattgatag agatgaaaag aaaaagaaaa gtgatggctc tgggcctaat   4680
ttggctggag atggagaact tgttgaagct cctctggggt tgtttcctcg gccttggcct   4740
acaaattctg atgcatcaga gggtagccgg ttttcaaaag tcgttgagta tttccggctg   4800
ctaggtcgtg ttatggctaa agctcttcaa gacggacgac ttttggacct gccattgtca   4860
gtggcatttt ataagcttgt tctcggccaa gatcttgatt tgcatgacat tctgtccatt   4920
gatgctgagc ttgggaagac tttgcaagag ttcaatgccc ttgtttgtcg gaaacattat   4980
atagaatcta ttggtggtag ctatacagat acaattgtta acttgcattt tcatggggtg   5040
ccaatcgaag atctttgctt agattttaca ctccctggtt atcctgaata caccttgaag   5100
ccaggagatg aaattgttga tatcaacaat ttggaggagt atatatcctt ggtggcagat   5160
gcaactgtca agactggaat catgcggcaa atagaagcat ttagagcagg gtttaaccag   5220
gtttttgaca tctcgtcttt acaaattttt actcctcaag aactagataa tttgctttgc   5280
ggctgcaggg agttgtggga gtctgagaca cttgctgatc atataaaatt cgaccatggg   5340
tacaatgcaa agagccctgc cattattaat ttacttgaaa ttatgggagg gttcacacca   5400
```

```
gagcagcaac gtgccttctg tcaatttgtt actggtgcac ctaggctgcc acctggaggg   5460

ctggcagttc taaatccaaa actaacgatt gtgaggaagc tttcgtcaac cgcagttaat   5520

acttcatcta atgggaatgg accttcagaa tcagcagatg atgacttgcc tagtgtgatg   5580

acatgtgcta attacctgaa acttcctcct tactctacca aggaaattat gtacaagaag   5640

ctactctatg caatcaacga gggccgggga tcctttgatt tatcatga                5688


<210> SEQ ID NO 4
<211> LENGTH: 1895
<212> TYPE: PRT
<213> ORGANISM: Glycine max

<400> SEQUENCE: 4

Met Glu Thr Arg Ser Arg Lys Arg Ala Glu Ala Ser Ser Ala Ala Pro
1               5                   10                  15

Ser Ser Ser Ser Ser Thr Thr Thr Thr Thr Ala Ser Arg Ser Ala Lys
            20                  25                  30

Cys Ser Arg Leu Ser Ser Ser Ser Ser Ser Ile Pro Asn Thr Thr Thr
        35                  40                  45

Ala Asn Thr Arg Ser Arg Ser Ala Arg Asn Asn Asn Asn Asn Ser Val
    50                  55                  60

Ser Pro Met Asp Pro Thr Asn Glu Ser Ser Gly Ser Arg Arg Asp Arg
65                  70                  75                  80

Arg Gly Lys Asn Phe Asp Arg Asp Asn Ser Asp Lys Gly Lys Glu Lys
                85                  90                  95

Glu His Asp Val Arg Ile Arg Asp Ala Glu Arg Glu Arg Ala Leu Ala
            100                 105                 110

Leu Asn Leu Glu Ala Glu Asp Val Gly Asp Asp Asp Asp Asp Asn Asp
        115                 120                 125

Ser Glu Gly Gly Val Gly Ile Leu His Gln Asn Leu Ile Ser Ala Ser
    130                 135                 140

Thr Phe Arg Gly Leu Leu Arg Lys Leu Gly Ala Gly Leu Asp Asp Leu
145                 150                 155                 160

Leu Pro Ala Thr Ala Met Gly Gly Ser Val Pro Ser Ser His Gln Thr
                165                 170                 175

Gly Gly Leu Lys Gln Ile Leu Ser Gly Leu Arg Ala Asp Gly Glu Glu
            180                 185                 190

Gly Arg Gln Val Glu Ala Leu Thr His Leu Cys Asp Met Leu Ser Ile
        195                 200                 205

Gly Thr Glu Asp Ser Leu Ser Thr Phe Ser Val Asp Ser Phe Val Pro
    210                 215                 220

Val Leu Val Gly Leu Leu Asn His Glu Ser Asn Pro Asp Val Met Leu
225                 230                 235                 240

Leu Ala Ala Arg Ala Leu Thr His Leu Cys Asp Val Leu Pro Ser Ser
                245                 250                 255

Cys Ala Ala Val Val His Tyr Gly Ala Val Ser Ile Phe Cys Ala Arg
            260                 265                 270

Leu Leu Thr Ile Glu Tyr Met Asp Leu Ala Glu Gln Ser Leu Gln Ala
        275                 280                 285

Leu Lys Lys Ile Ser Gln Glu His Pro Thr Ala Cys Leu Arg Ala Gly
    290                 295                 300

Ala Leu Met Ala Val Leu Ser Tyr Leu Asp Phe Phe Ser Thr Gly Val
305                 310                 315                 320

Gln Arg Val Ala Leu Ser Thr Ala Ala Asn Met Cys Lys Lys Leu Pro
```

```
            325                 330                 335

Pro Asp Ala Ala Asp Phe Val Met Glu Ala Val Pro Leu Leu Thr Asn
            340                 345                 350

Leu Leu Gln Tyr His Asp Ser Lys Val Leu Glu His Ala Ser Val Cys
        355                 360                 365

Leu Thr Arg Ile Ala Lys Ala Phe Ala Ser Ser Pro Asp Lys Leu Asp
    370                 375                 380

Glu Leu Cys Asn His Gly Leu Val Thr Gln Ala Ala Ser Leu Ile Ser
385                 390                 395                 400

Thr Ser Gly Ser Gly Gly Gly Gln Ala Ser Leu Ser Thr Pro Thr Tyr
                405                 410                 415

Thr Gly Leu Ile Arg Leu Leu Ser Thr Cys Ala Ser Gly Ser Pro Leu
            420                 425                 430

Gly Ala Lys Thr Leu Leu Leu His Gly Ala Ser Gly Ile Leu Lys Asp
        435                 440                 445

Ile Leu Ser Gly Ser Gly Val Ser Ser Asn Thr Ser Val Ser Pro Ala
    450                 455                 460

Leu Ser Arg Pro Ala Asp Gln Ile Phe Glu Ile Val Asn Leu Ala Asn
465                 470                 475                 480

Glu Leu Leu Pro Pro Leu Pro Gln Gly Thr Ile Ser Leu Pro Val Ser
                485                 490                 495

Ser Asn Leu Phe Val Lys Glu Ser Val Val Lys Lys Ser Pro Pro Ser
            500                 505                 510

Gly Asn Pro Gly Ile Gln Glu Asp Thr Asn Gly Asn Val His Glu Ile
        515                 520                 525

Ser Ala Arg Ala Lys Leu Leu Asn Asp Lys Pro Glu Leu Leu Lys Gln
    530                 535                 540

Phe Gly Met Asp Leu Leu Pro Val Leu Met Gln Ile Tyr Gly Ala Ser
545                 550                 555                 560

Val Asn Gly Pro Val Arg His Lys Cys Leu Ser Val Ile Gly Lys Leu
                565                 570                 575

Met Tyr Phe Ser Thr Ala Glu Met Ile Gln Ser Leu Leu Ser Val Thr
            580                 585                 590

Asn Ile Ser Ser Phe Leu Ala Gly Val Leu Ala Trp Lys Asp Pro His
        595                 600                 605

Val Leu Val Pro Ala Leu Gln Ile Ser Glu Ile Leu Met Glu Lys Leu
    610                 615                 620

Pro Gly Ile Phe Ser Lys Met Phe Val Arg Glu Gly Val Val His Ala
625                 630                 635                 640

Val Asp Gln Leu Ile Leu Ala Gly Asn Ala Thr Asn Ile Ser Thr Gln
                645                 650                 655

Thr Ser Ser Ala Glu Lys Asp Thr Asp Ser Val Ser Gly Thr Ser Ser
            660                 665                 670

Arg Ser Arg Arg Tyr Arg Leu Arg Ser Gly Asn Ser Asn Pro Asp Ala
        675                 680                 685

Asn Arg Ser Asp Asp Leu Lys Ser Pro Val Pro Val Asn Val Gly Leu
    690                 695                 700

Pro Pro Ser Ser Val Glu Thr Pro Thr Thr Asn Ser Ser Ile Arg Ala
705                 710                 715                 720

Ser Ile Ser Ser Val Ala Asn Ala Phe Lys Asp Lys Tyr Phe Pro Ser
                725                 730                 735

Asp Pro Gly Ser Val Glu Val Gly Val Ser Asp Asp Leu Leu His Leu
            740                 745                 750
```

```
Lys Asn Leu Cys Ser Lys Leu Asn Thr Gly Val Asp Asp Gln Arg Ser
        755                 760                 765

Lys Ala Lys Gly Lys Val Glu Ala Ser Gly Phe Asp Leu Asp Asp Asp
    770                 775                 780

Ser Thr Asn Thr Glu Glu Tyr Leu Ile Gly Val Ile Ser Asp Met Leu
785                 790                 795                 800

Lys Glu Leu Gly Lys Gly Asp Ser Val Ser Thr Phe Glu Phe Ile Gly
                805                 810                 815

Ser Gly Val Val Glu Ala Leu Leu Asn Tyr Phe Ser Cys Gly Tyr Phe
            820                 825                 830

Ser Lys Asp Arg Ile Ser Glu Thr Asn Leu Pro Lys Leu Arg Gln Gln
        835                 840                 845

Ala Leu Thr Arg Phe Lys Ser Phe Val Ala Val Ala Leu Pro Leu Ser
    850                 855                 860

Ile Asp Asn Gly Ala Val Ala Pro Met Thr Val Leu Val Gln Lys Leu
865                 870                 875                 880

Gln Asn Val Leu Ser Ser Leu Glu Arg Phe Pro Val Met Leu Ser Asn
                885                 890                 895

Ser Ser Arg Ser Ser Ser Gly Ser Gly Arg Leu Ser Ser Gly Leu Ser
            900                 905                 910

Ala Leu Ser Gln Pro Ile Lys Leu Arg Phe Cys Arg Ala Gln Gly Glu
        915                 920                 925

Lys Ser Leu Lys Asp Tyr Ser Ser Ser Val Val Leu Ile Asp Pro Leu
    930                 935                 940

Ala Ser Leu Ala Ala Ile Glu Glu Phe Leu Trp Ala Arg Val Gln Arg
945                 950                 955                 960

Gly Glu Ser Gly Leu Lys Ser Thr Val Gly Thr Glu Asn Ser Glu Ser
                965                 970                 975

Gly Thr Thr Pro Ala Gly Ala Gly Val Ser Ser Pro Ser Ser Tyr Ile
            980                 985                 990

Pro Ser Thr Ala Phe Arg Tyr Ser  Thr Gly Ser Arg Ser  Arg Ser Ser
        995                 1000                1005

Val Asn  Ile Gly Asp Thr Pro  Arg Lys Glu Ile Phe  Gln Asp Asn
    1010                1015                1020

Gly Thr  Ser Ser Ser Lys Ser  Lys Gly Lys Ala Val  Leu Lys Pro
    1025                1030                1035

Ala Gln  Glu Glu Ala Arg Gly  Pro Gln Thr Arg Asn  Ala Val Arg
    1040                1045                1050

Arg Arg  Ala Ala Leu Asp Lys  Asp Ala Gln Met Lys  Pro Ala Asn
    1055                1060                1065

Gly Asp  Ser Thr Ser Glu Asp  Glu Glu Leu Asp Ile  Ser Pro Val
    1070                1075                1080

Glu Ile  Asp Glu Ala Leu Val  Ile Glu Asp Asp Asp  Ile Ser Asp
    1085                1090                1095

Asp Glu  Asp Glu Asp Arg Glu  Asp Val Arg Arg Asp  Tyr Tyr Leu
    1100                1105                1110

Pro Val  Tyr Leu Pro Asp Glu  Val His Asp Val Lys  Leu Gly Asp
    1115                1120                1125

Ser Ala  Glu Glu Ser Thr Val  Ala Pro Ala Thr Ser  Asp Ser Gln
    1130                1135                1140

Thr Asn  Ala Ala Ser Gly Ser  Ser Ser Lys Ala Gly  Thr Ala Arg
    1145                1150                1155
```

```
Gly Cys  Asp Ser Ala Asp Phe  Arg Ser Gly Tyr Ser  Ser Ser Ser
    1160                 1165                 1170

Arg Gly  Ala Met Ser Phe Ala  Ala Ala Ala Met Ala  Gly Leu Gly
    1175                 1180                 1185

Tyr Ala  Asn Ser Arg Gly Phe  Arg Gly Gly Arg Asp  Arg His Gly
    1190                 1195                 1200

Arg Leu  Leu Phe Gly Ser Ser  Asn Asp Pro Pro Lys  Leu Ile Phe
    1205                 1210                 1215

Thr Ala  Gly Gly Lys His Leu  Asn Arg Asn Leu Thr  Ile Tyr Gln
    1220                 1225                 1230

Ala Ile  Gln Arg Gln Leu Met  Leu Asp Glu Asp Asp  Asp Glu Arg
    1235                 1240                 1245

Leu Ala  Gly Ser Asp Arg Val  Ser Ser Asp Gly Ser  Ser Leu Trp
    1250                 1255                 1260

Gly Asp  Ile Tyr Thr Ile Thr  Tyr Gln Arg Ala Glu  Asn Gln Pro
    1265                 1270                 1275

Asp Lys  Ala Ser Asn Gly Gly  Ser Ser Ser Asn Thr  Ser Lys Ser
    1280                 1285                 1290

Ala Lys  Ser Gly Ser Ala Leu  Asn Ser Ser Ser Glu  Ala Lys Leu
    1295                 1300                 1305

His Gln  Thr Ser Val Leu Asp  Ser Ile Leu Gln Gly  Asp Leu Pro
    1310                 1315                 1320

Cys Asp  Leu Glu Lys Ser Asn  Pro Thr Tyr Asn Ile  Leu Ala Leu
    1325                 1330                 1335

Leu Arg  Val Leu Glu Gly Leu  Asn Gln Leu Ala Pro  His Leu Arg
    1340                 1345                 1350

Thr Gln  Met Val Ser Asp Ser  Phe Ala Lys Gly Lys  Ile Leu Asp
    1355                 1360                 1365

Leu Asp  Glu Leu Gly Val Thr  Thr Gly Ala Arg Val  Leu Pro Glu
    1370                 1375                 1380

Glu Phe  Val Ser Gly Lys Leu  Thr Pro Lys Leu Ala  Arg Gln Ile
    1385                 1390                 1395

Gln Asp  Ala Leu Ala Leu Cys  Ser Gly Ser Leu Pro  Leu Trp Cys
    1400                 1405                 1410

Cys Gln  Leu Thr Lys Ala Cys  Pro Phe Leu Phe Pro  Phe Asp Thr
    1415                 1420                 1425

Arg Arg  Gln Tyr Phe Tyr Ser  Thr Ala Phe Gly Leu  Ser Arg Ala
    1430                 1435                 1440

Leu Tyr  Arg Leu Gln Gln Gln  Gln Gly Ala Asp Gly  His Gly Ser
    1445                 1450                 1455

Thr Thr  Glu Arg Glu Val Arg  Val Gly Arg Leu Gln  Arg Gln Lys
    1460                 1465                 1470

Val Arg  Val Ser Arg Asn Arg  Val Leu Asp Ser Ala  Ala Lys Val
    1475                 1480                 1485

Met Gly  Met Tyr Ser Ser Gln  Lys Ala Val Leu Glu  Val Glu Tyr
    1490                 1495                 1500

Phe Gly  Glu Val Gly Thr Gly  Leu Gly Pro Thr Leu  Glu Phe Tyr
    1505                 1510                 1515

Thr Ile  Leu Ser His Asp Leu  Gln Gln Val Gly Leu  Gln Met Trp
    1520                 1525                 1530

Arg Ser  Tyr Ser Ser Glu Lys  His Gln Met Glu Ile  Asp Arg Asp
    1535                 1540                 1545

Glu Lys  Lys Lys Lys Ser Asp  Gly Ser Gly Pro Asn  Leu Ala Gly
```

```
    1550                1555                1560

Asp Gly  Glu Leu Val Glu Ala  Pro Leu Gly Leu Phe  Pro Arg Pro
    1565                1570                1575

Trp Pro  Thr Asn Ser Asp Ala  Ser Glu Gly Ser Arg  Phe Ser Lys
    1580                1585                1590

Val Val  Glu Tyr Phe Arg Leu  Leu Gly Arg Val Met  Ala Lys Ala
    1595                1600                1605

Leu Gln  Asp Gly Arg Leu Leu  Asp Leu Pro Leu Ser  Val Ala Phe
    1610                1615                1620

Tyr Lys  Leu Val Leu Gly Gln  Asp Leu Asp Leu His  Asp Ile Leu
    1625                1630                1635

Ser Ile  Asp Ala Glu Leu Gly  Lys Thr Leu Gln Glu  Phe Asn Ala
    1640                1645                1650

Leu Val  Cys Arg Lys His Tyr  Ile Glu Ser Ile Gly  Gly Ser Tyr
    1655                1660                1665

Thr Asp  Thr Ile Val Asn Leu  His Phe His Gly Val  Pro Ile Glu
    1670                1675                1680

Asp Leu  Cys Leu Asp Phe Thr  Leu Pro Gly Tyr Pro  Glu Tyr Thr
    1685                1690                1695

Leu Lys  Pro Gly Asp Glu Ile  Val Asp Ile Asn Asn  Leu Glu Glu
    1700                1705                1710

Tyr Ile  Ser Leu Val Ala Asp  Ala Thr Val Lys Thr  Gly Ile Met
    1715                1720                1725

Arg Gln  Ile Glu Ala Phe Arg  Ala Gly Phe Asn Gln  Val Phe Asp
    1730                1735                1740

Ile Ser  Ser Leu Gln Ile Phe  Thr Pro Gln Glu Leu  Asp Asn Leu
    1745                1750                1755

Leu Cys  Gly Cys Arg Glu Leu  Trp Glu Ser Glu Thr  Leu Ala Asp
    1760                1765                1770

His Ile  Lys Phe Asp His Gly  Tyr Asn Ala Lys Ser  Pro Ala Ile
    1775                1780                1785

Ile Asn  Leu Leu Glu Ile Met  Gly Gly Phe Thr Pro  Glu Gln Gln
    1790                1795                1800

Arg Ala  Phe Cys Gln Phe Val  Thr Gly Ala Pro Arg  Leu Pro Pro
    1805                1810                1815

Gly Gly  Leu Ala Val Leu Asn  Pro Lys Leu Thr Ile  Val Arg Lys
    1820                1825                1830

Leu Ser  Ser Thr Ala Val Asn  Thr Ser Ser Asn Gly  Asn Gly Pro
    1835                1840                1845

Ser Glu  Ser Ala Asp Asp Asp  Leu Pro Ser Val Met  Thr Cys Ala
    1850                1855                1860

Asn Tyr  Leu Lys Leu Pro Pro  Tyr Ser Thr Lys Glu  Ile Met Tyr
    1865                1870                1875

Lys Lys  Leu Leu Tyr Ala Ile  Asn Glu Gly Arg Gly  Ser Phe Asp
    1880                1885                1890

Leu Ser
    1895
```

<210> SEQ ID NO 5
<211> LENGTH: 16430
<212> TYPE: DNA
<213> ORGANISM: Glycine max

<400> SEQUENCE: 5

-continued

```
atggaaaact cgaaatcaag ggtttcaaag taataggagg tacaagaaaa gcttgcaaat     60
ccatcacccg agagaatata aaactcttag aaccaagaaa catctaactt cccctaacct    120
tacaccgtat tttactttca caataaaaaa taattacctg gatagttgct ttcaacccaa    180
atttcttaag agcaacaatg gcattaggat ttccagccca ttttacagaa gactccataa    240
ttaactcttt ttcgtcagtc tcataaactt tcattcttat tgagaataaa ttatgcattc    300
aataagaaaa atggaaaaat tcacatagaa tcacaaataa gttagtaaaa aatagaataa    360
ttgcatttat aaaacaaaca cataagtatt ttgtaggggt cataaagttg acttagtggt    420
gatataaaaa aagagaatag agagattgta tacattaatt cttccactaa caaaaaatga    480
acaactaata tttatcaata aaaaaagtat acgtgatatt tttttttttt taaagagata    540
aaccatttta acaaaaaaaa tattttataa gggttccttt taatgagtga agcccaaaac    600
aagatcttat ggtaaaatgc atcatttgat agatcaaagt ttctttaaac tctaaataaa    660
attcatacca gtatgggttt caaaccttaa taattatcaa ataccagtaa tgtaattgat    720
tttagagatg cagtaaaaac aaatgaaaat tgaactgtct taatatttga tgtattattt    780
tcgaaatgaa tatttgatat attattaaag atgtatttta tgagtattta agatgtttta    840
ttgttctttc aaattaaaac catcttgtta attgttagtt tattacattt ctcccaaaaa    900
aacatgattt atcattagaa ccaaaaataa tttctaaatt gtgatttgta tcctttacag    960
atgataaaaa cgagtgaaat ttaggtatta tcatagttta cacattggta atatttatat   1020
tatttgtgca aaccagtaaa aagtttttat ctaataataa accacatcta aataaactaa   1080
ccttgaaaag ttggcggcaa agaccctagt gagctcttca aactcaacag aatcaatttt   1140
atatttcggt atttgctcat caattattgg ttttgcaata ttctttgcag tcttgcatat   1200
tgcctaaatg aaaaaaccca atcaaacaat cacacaaaaa agaagaaaaa atacatgcta   1260
cttgataatt gtccgaaaat ataataaaac ataccttttc aaggtatggc cacatatatt   1320
caataagctt gttaagccaa tcaaccttca taaaaacacc aataaataat agtgtggttg   1380
ttaaaatact tgtggagtgt gtttggatga gaaattttaa attctaaaaa ttttaaatac   1440
ttcaattcaa attcttttat tttcaaaatt ttgtgtttgg ataaaaaaaa attaaaattg   1500
tgagggtgaa agaaaatgaa tgcaaagaga aaaaaaaata tggttagtgt gcttctaaag   1560
agaagaatat tgatgtgcca tggggagtcg cacggaaacc gggatacaat gacgtacacc   1620
atcatatccg accacaacat taagtcaacg gcgcaaggca tggcccagac ctttcgcacc   1680
gacgagcacc tctatcgcgt gatagacaac gataattgtt cccctgattg gcaccgttct   1740
atgtgtctcc ctatatccgc acccgatcga tgctccgcgt gagctcagac agtgtttcat   1800
gaagtagaga attatcgacg taaggaaaga ttcacgagtt cgagaacgag atttcaaact   1860
caggtgaacg agaggatgaa gatgataaag gaaatataca aacattttgg aatattctct   1920
tatcaagaag agaattttaa tttctcactt ttgaaaaaaa attaaaattt cacattttta   1980
gttgtttaaa attctgtttt aaaattttaa attctccata aaaaaaacat ccaaataatg   2040
aattttaaat taaaaaaatt taaattttct gataaattac ttttcttagt taaaattcgt   2100
agtgcatttt acatattaac aaagagtaac ccattgcttt cccgatcaaa gtctggattt   2160
ttttatccaa aggggtatct caggaatcat tccctgtaaa gttttcgagt cttcctccgc   2220
caatggctgg atatcaggat cctatccaag ccaacaatgt attggtgcaa tacttaaaaa   2280
atgcattaaa aatgtcaaaa tttcaaagat tcacaatcaa ttttcttttt tgattgcttt   2340
ttgacgtata taatagtgtg gcgttaccta ttttaaactt tttttcttat ggttagtgaa   2400
```

```
gttactaaag acaaaaatat ttagattcca agataatgtg taagataagg attattataa   2460
tttatgatca taatttacaa aaacttgtta gagaacattg attagcttgt aaaagaaaat   2520
aaaacaaaca aaattagacc cagacattat ctaaaggaaa gagaaaggtt tacaacgggg   2580
tggaatacaa aacaagataa tttgttaaga accatgtttt gtttgtacca tgtaccttaa   2640
cttcagtgga ttgaacgtaa ataaagagaa aataaccaat aacgagaccc atagaaatcc   2700
caaatccaaa tccaaaatga ccaaatatag tgctaaagaa atccatctca gttcttaatt   2760
ttgttttcag accaaacttg ctctgatgac aatcacaatc tctttctctc tccgtgtgct   2820
aaaagtaaaa ttattatgca aatccgttac ttccgatgtc tttgagttct cctcggatca   2880
ccattcctat attcaaacca aaacatgtaa tgcaaatcat tttgacccaa aaaaagacta   2940
tttatacaaa aaaaaaagtt atggttatta ctaaggattt aacacaaatg attacgttat   3000
tcttattaat taaagttact accactattt ttttggagtg acactaccac ataatttgtt   3060
tattcatgtt attatatatt tgaggaaaag tcataaataa attatataat gaataaaaat   3120
aaaataaaat atttaaaaat taaacatgtt actacattat ctttaacata ttttctctat   3180
atttttatgt tacaaaaaat tgtataatat ttaagaaaac aaaaacacta ttaaacacat   3240
agatcaattg atttaaaact attaaagttt aagtaatatt ttcgaattcg aattctatat   3300
atgttacggc atgaaatact tgtaggaaga attagatgct tgtggtctct aaaaaaaact   3360
tccctccctc aaaattttcc ctatggaatg tgaatttttt tgttgggtga tacaaaaatg   3420
attatgtttt ttctttacct ctttatttaa taaatagtaa aattttgatg ttctttcctt   3480
ttatttatca tttttccctt tttattaaac caaacaataa ctgagaggag gaatggggaa   3540
gtagcaattt ggattattct tttcttgttt ttttttaaa ataaaaaaca taacataaaa   3600
taaaaaatta attttgatgc attgttagtt gaaagatgat tattattata tattaaaagt   3660
taaataataa taataaataa tttatgttaa tttttaatct accaaattat tttaatttaa   3720
atattatttt ctgttttact ttatttatgt tgaatctacc aatatttatt tctcccccac   3780
cacccccatt ttttacatca acatagatta aaacggatag aatttgtagt ggaagattaa   3840
ataaaattga ttaataaaat atatgtatgt ttctgggggga caagtattta aatttaaatt   3900
tgataagata tgggtgatat gaaatgtagt aattttcaat gagccgaaaa cgacgcggag   3960
gcagcaagcg agttctcact tagagtgttg ttgttgtgca aacaaagtta agttacgtat   4020
aaaaggggta tttgatatct ctgtcttttt attctctccc tctcgctcct caccttaggg   4080
ttttcatgca acaatttcct cctcctcctc ctctctctct ctctctctac actagattgg   4140
ggattttcct tggatttagg gtttccgccg attttgattt taatttaata catttgtctg   4200
agatgcaacg gattaatcca atcgatcgat cggggatagg tgagacaaat tgaagggtga   4260
gtgtgggttt tgtatggaaa ctcggagtcg gaagcgggcg gaggcttcct cagctgcccc   4320
ttcatcctcg tccaccaccc cttctcgttc agccaagcgc tctcgtcttt cttcttcttc   4380
ttcttccatc ctacctgtta atacacgttc tcgttccgcc aggaataaca acaacaacaa   4440
caactccggt tccatttctt tcatggaccc caccaatgaa tcctccgggt cccgacgtga   4500
tcgccgtggc aagaatttcg atagggaaaa ttcggacaaa gggaaggaga aggaacagga   4560
tgttaggatt agggatgcgg agcgggagcg agagcgagcc ttggcgttaa acatggagag   4620
tgaagatgtt ggggatgacg atgataatga tagtgacggc ggtgtgggaa ttctgcacca   4680
gaatttgacg tctgccagta gtgcccttca agggcttctt cggaaacttg gtgctggttt   4740
```

-continued

```
ggatgatttg cttcctgcta ctgctatggg cggttctgcg tcatctcctc atcagagtgg   4800
cagactcaag aagattttgt ctggcttgcg tgccgatggg gaagaaggtc gtcaggttga   4860
ggcattgacg cagctttgtg acatgctctc cattggcact gaagattccc tcagcacatt   4920
ttcggttgac tcatttgttc ctgtgctagt gggcttgctt aatcacgaga gcaatcccga   4980
tgtcatgctt cttgcggcca gggcgctaac ccatttatgt gatgtgcttc cttcatcctg   5040
tgctgctgtt gtgcattatg gtgctgtctc tatcttctgt gcgaggctgc tcaccataga   5100
gtatatggac ttggctgagc aggttatttt ctcagtcaat ctcttttgtg cctttactta   5160
ttatgtatct gtgtcttacg atgtatgagc ttcctaagtc cttaaccctt agttgttgaa   5220
aatgggcttc cgtcttaaac gaggttctta tcatttgaca caccttacgg ttttctactt   5280
tgaattctga tagttgtgat tgttgatgtg aacagtctct tcaagcacta aagaagattt   5340
ctcaggagca cccaactgcc tgtcttagag ctggagctct gatggctgtt ctttcttact   5400
tggacttctt ctcaacagga gttcaggtaa ctaatcaatg aaatcctaac atcaaagggt   5460
gacaattcat tttgcgttta ccacccttga ttagcaagcc tatattgaca taatcatgtg   5520
tttcagcggg tggcattgtc tactgctgca aatatgtgca agaagcttcc tcctgatgca   5580
gctgactttg tgatggaagc tgttccactt ttgacaaacc tccttcagta ccacgactcc   5640
aaggtaaggc atgtttgctt gtcatatttg tcataaaatg aaaactgcac tttccttgtc   5700
attccttcct tttaaggaaa ttttgtttgt gtaaatattg atccctacaa ctgatgttgt   5760
caattatcta tttgcgtttt cataataaaa aacttcgtac cccattgtcc agaggctctt   5820
cactatgcga aggtatgggg gagggatgtt gtacgcagcc ttacccttgc attttcataa   5880
tattcaatgt taatttttgt aggtcctgga acatgcctct gtttgtttga cacgaatagc   5940
tgaagcattt gcatcatctc cagacaaatt agatgaattg tgcaatcatg gactggtaac   6000
acaagctgcc tctctcattt ctaccagcag ttctggaggt gggcaggctt ctctcagcac   6060
tccaacatat actgtaagtg caatctttgc cactaaatct gatactttta tcctttggtg   6120
ggttgttcct ttgacttcat tggtgcatgc agggtttgat ccgccttctt tccacatgtg   6180
caagtgggtc tcctcttgga gctaaaacgt tgcttctcct tggaactagt ggcattctta   6240
aagatatact atccggttcc ggtgtttctt ctaacacctc tgtttcgcct gcattgagta   6300
ggccagcgga tcaggtatgt gtacttttga gttctttatg tctgttatat gtagttggta   6360
tctctatagt tcatttgata gattgtgaca tcgatctcat tatttaaatc cttgaaaact   6420
tttcagttcc ctttttgtga aagatgagtt tttcctaatt ctctttccta atatttagat   6480
atttgagatt gtgaacctgg caaatgaact tctgcctcca ttgcctcaag gaaccatttc   6540
ccttcctgtc agctccaact tgtttgtgaa agggtctgtt gtgaaaaaat cctcttctgg   6600
caattctggg atacaagaag acacaaatgg aaatgttcat gagatattgg ctcgtgagaa   6660
attattaaat gatcagcctg agttacttca gcaatttggg atggatctcc tcccagtttt   6720
aatgcaggtt caatgcttaa atttacttaa ttgttaaaat gctcaaatta tattttgtga   6780
tttgtttatt aatttttaac ttcttaaata aataactggc tctatttttt atatcctcga   6840
cttcttcatt ccttcactcc cgtcacttat tactagtttt gtcttgcttt tgaaacagat   6900
atatggtgct agcgtcaatg gtccagttcg gcacaaatgt ctttctgtca ttggaaaatt   6960
gatgtatttc agcacagctg agatgatcca gtctttactg agtgtaacaa atatatcaag   7020
gtatctagaa cttcaattgg gttgctgttg ctctatgttc tctgtagaat acttatgcat   7080
tgtcactttg atgatatagt ttcttagctg gtgtgttagc atggaaagat ccacatgttt   7140
```

```
tggttcctgc cttgcaaatt tcggaaattc ttatggaaaa gcttcctgga accttctcta   7200
agatgtttgt cagagaaggt gtggttcatg cagttgacca acttattttg gctggaaatt   7260
caaccaatat atccacacaa acatcatctg ctgagaagga taatgattct gtatctggaa   7320
cttcatctcg ctctagacgc tatcgcctgc gcagtggtaa ttcaaatccc gatgcgaacc   7380
cttcagatga tttaaagagt ccagttccag taaatgttgg tttgccacca agttctgtag   7440
aaactccaac aactaattct agtatccgtg catctgttag ctcagttgct agagctttta   7500
aagacaagta ctttccttct gatcctgggt ctgttgaagt gggtgttagt gatgatcttt   7560
tgcatctgaa aaatctatgc acgaagttga tcactggtgt tgatgaccaa agaagcaagg   7620
caaagggaaa agttaaagct tctggatttg gtctggatga taattctagt aacacagaag   7680
agtatttgat tggggtgata tctgacatgc taaaggaact tggcaaagga gatagtgtat   7740
ctacttttga atttatcggt agtggtgttg ttgaagcctt gctaaattat ttttcttgtg   7800
ggtatttctc taaagatcga atatcagaaa ccaatctccc caagcttcgc caacaggcac   7860
tttcaaggtt caagtcattt gtagctgttg cactaccttt gagcattgac aatggggctg   7920
ttgctcctat gactgtctta gttcagaagc ttcaaaatgc gttggcctcc ttggagcgtt   7980
tccctgttat gctgagtaat tcatctcggt catctagtgg aagtgcacgt ctctcctctg   8040
ggctaagtgc attatctcag cccataaaat tacgtctctg ccgagcccag ggtgaaaagt   8100
cacttaggga ttattcatcc aatgtggtac tgattgatcc attagcaagt ctagcagcca   8160
tcgaggaatt tctatgggct cgtgtccagc gtggtgaatc tggtcagaag tctactgtag   8220
gcactgaaaa ttctgaatct ggaacaactc ctgctggggc aggtgtttca tctccttcct   8280
cttatactcc ctccactgcc catcgtcatt ctactagaac cagatcatct gttaatatag   8340
gagatacacc tagaaaagaa acatctcaag acaaaggaac gagctcatca aagagcaagg   8400
gtaaagctgt attaaaacct gcgcaggagg aagcgcaagg accccaaaca aggaatacag   8460
tgcgcagaag agcagctctt gataaagtcg ctcaaatgaa acctgcaaat ggcgactcaa   8520
cttctgaggt atgctgctaa attctgggaa cgagtcataa taattaaata atattaatct   8580
aaattggttt ataacattga ataatttaat ctttgttgga ttttgtttat acttatgctt   8640
attctccttc cctcttttg ttagataaaa aaccattggt gagatttctt catctaatag   8700
ttagttgatg ttggctttta ttttactgct ttggattaaa atgatgcttt cagttgacgt   8760
gtctcctgta gcatcttaaa cttgagtggt ggcttttatt atttaagtca tttttattgt   8820
ttgacattat tttcccctgc ttttatggga taggatgaag aattggatat atctcctgtt   8880
gaaattgctg aggctttggt gattgaagat gatgatattt ctgatgatga ggatgaagac   8940
catgaagatg tatgtttctt cttctgctaa gatttcatct tattgttgtg attactttta   9000
ttcatatctc attttgtgat ctaaattgta agatctcaca atcttgctgc cactttcctt   9060
tctgaatcac ttgtaaaatc ttaaatgagt tcgttgtgag atttcaagat tgctgaactg   9120
gtgagattgt gtaatcatgt gcagtccaaa aatctgtcaa tttcgagtta tgtttcaagt   9180
attttctttt gtgacttctg gttgtgttat gtatgtgact aattatgact tgttttggat   9240
gttatggtta tgaaatttca aggctaagtt tgctataatg ttatctatat ttttctttca   9300
tattttctat gcatacataa acctatataa ttttttggta ggattttatg atctacattt   9360
tacaattttg catccccctt ccaatcttag gtagaatctc aatcttgaca acattggttg   9420
ttaccaatat tgaaaactat catttaggcg catccattct tgcaattgag ttttaccaaa   9480
```

-continued

```
tagaaatgtt attgttgttt ccaagaatgg atactaccat taattgttgt ttagattgga   9540
tattatgatt tggtttagct gttctgttct agctattgaa ttttatcaaa tagaaatggt   9600
actattgttt cttatatttt taataatcat taattgatga ttccaagatt ggatgctatc   9660
atttgattca gttgcatcca tgctagtaat tgaatttatg atattattcc actaaccatc   9720
atctaatgca tcatcagctt gttttattta ttttatttta ttttatttta tttttgagca   9780
ggtgctgagg gatgattctc ttcctgtctg cttgcctgac aaagtgcatg atgtgaaatt   9840
gggtgactca gctgaggaga gtactgttgc tccagcaaca agtgatagcc agactaatgc   9900
agcctcaggt tcaagcagca aagctggtac agccaggggt tctgactccg ctgattttag   9960
gagtgggttt tcatctagct caaggggtgc aatgtcattt gctgctgctg ctatggctgg  10020
acttggatat gctaatagca gaggtttcag gggcggcaga gataggcatg ggtgcctgtt  10080
gtttggtagt tctaatgatc ctccgaagtt gatttttact actggtggga agcagcttaa  10140
taggaatctg agtatatatc aggcaattca aagacagctt gtgctagatg aagatgatga  10200
tgagagattt gctggcagtg actatgtatc tggtgatgga agcagtctgt ggggtgatat  10260
ttacaccatc acttatcaaa gggcagaaaa ccagccagat aaggcgtcta ctggaggatc  10320
aagttcaaat acttcaaaat ctgccaaatc tgggtctgcc ttaaattcaa gctcagaagc  10380
taaattgcat cagacatctg ttctagacag tatattgcag ggagaattgc catgtgatct  10440
agagaaatct aatcccacct acaatatttt ggcactcctg cgtgtgctgg agggtttcaa  10500
ccaacttgcg cctcgtttga gggtcctaat ggtttctgat agctttgcca agggaaaaat  10560
cttggattta gatgagctat gtgttacaac tggtgctagg gtgcttctag aggaatttgt  10620
aagtggtaag cttactccaa aattggctag gcaaatacaa gatgcccttg cactatgcag  10680
tggtaatctt cccttatggt gttaccagtt gactaaagcg tgccctttct tgtttccttt  10740
tgagacccga cgacagtact tttattctac cgcatttggg ttatctcgtg cactgtatcg  10800
acttcaacag cagcaaggtg ctgatggcca tggttcaaca actgagaggg aggtgagagt  10860
tgggagattg cagcgccaaa aggttcgtgt ctctcgaaat cgtgtcctgg attctgctgc  10920
aaaagttatg gagatgtatt ctagccaaaa agctgtactt gaagtagaat attttggtga  10980
agttggcact ggtctgggtc ccacccttga gttttataca attctaagtc atgatttgca  11040
aaaagttgga ctgcaaatgt ggagatctta ttcttcagac aaacatcaaa tggaaataga  11100
tggagatgaa aagaaaaaga aaagtgaagg ctctgggcct aatttggctg gagatggaga  11160
acttgttcaa gctcctctgg ggttgtttcc tcggccatgg cctacaaatt ctgatgcttc  11220
agagagtagc cagttttcaa aagtcattga gtatttccgg ctactaggtc gtgttatggc  11280
taaagctctt caagacggac gactactgga cctgccattg tcagtggcat tttataagct  11340
tgttctctgc caagtatgtt gtgcaatatt gatgttttaa ccattttcat tttttattgt  11400
taatctgatg gtcaatttat tctagtcaat gaacctaacc ttcactttgt ggcaggatct  11460
tgatttgcat gacattctgt tcattgatgc tgagcttggg aagactttac aagagttcaa  11520
tgcccttgtt tgtcggaaac attatataga atctattggt ggtagctata cagatacaat  11580
tgttaacttg tattttcatg gtgcaccaat cgaagatctt tgcttagatt ttactctccc  11640
tggttatcct gaatacacct tgaagccagg agatgaaatt gtatggagtt aaaccctgag  11700
ctagtctata gatcttggtt cttctgttat gaaaatttcc tttaacttac tctcaaattc  11760
tcaggttgat atcaacaatt tggaggagta tatatccttg gtgatcgatg caactgtcaa  11820
gactggaatc atgcggcaaa tagaagcatt tagagcaggg tttaaccagg ttttatgctg  11880
```

```
ttcttaataa ttagtaattt aactttaaat gtacacattg ttggtgtgga gcatgttatt  11940
tttctaaaac aaggtgtttc cctctcccct ttctagtgga aagtatcttt tattgacatt  12000
atcctccttg tctatatatg ctcccatact tatctcccac tgcatccctg agaatttgtt  12060
ttttaaccgt gcttaatggt gttgttagat ccacgtagct gacatctcct tgtgggataa  12120
gattattgta gttgtagatt ggaattagtt tacctgatgc atgacattaa tttgttaaca  12180
tgccattgaa attcttaagt gacattctgt ctcactaaaa gttatttggt gttttaccga  12240
gatcttaaat atctttcctt tatctctcat gcttgaatat tccacttggg atcttataaa  12300
atatatgatc ctgttctttt acttacattg gctcccaatc accaactata ctttccctgt  12360
acaaaatgga aattgcaaga ttcagttatt ggatgttaaa ctttttacat tctgaatata  12420
ttgtttgtga aatgggtggg gtagttatgg ctctgctaga ctctcttgtg gaggatgaga  12480
agaggatatt gatggggaaa ttagttactt ttggctcatt ttatttagtt caaaactaaa  12540
catcacttgt atgcttgtgc tgtttaatgc aggtttttga tatctcatct ttacaaattt  12600
ttactcctca agaactagat aatttgcttt gcggccgcag ggagttgtgg gaggtgattt  12660
ttgcccaatt atattattgc ttttaatatt agttaaaata ttagatttag aacaaggcat  12720
tgaaattaaa agttttttgt ttttaatctt actgcaggct gagacacttg ctgatcatat  12780
aaaattcgac catgggtaca atgcaaagag ccctgccatt gttaatgtat gttttttttcc  12840
tcctaattat aagtaatatt gtgtattata gaaaattaga gctagttata atttatgatg  12900
cttgtcctgt tggatgctat tttagttact tgaaattatg ggagagttca caccagagca  12960
gcaacgtgcc ttctgtcaat ttgttactgg tgcacctagg ctgccacctg gagggctggc  13020
agttctaaat ccaaaactaa cgattgtgag gaaggtattc agaaatgaat ttttgataac  13080
gtgatattta ggcttattca tctatatttt ttttcatatt aatttcatgg ttatatatgc  13140
atgtcaatat ttgttattac cgttgtattc atgccttatt ttttggcctt ggtgcagctt  13200
tcgtcaactg cagttaataa ttcatctaat gggaatggac cttcagaatc agcagatgat  13260
gacttgccta gtgtgatgac atgtgctaat tacctgaaac ttcctcctta ctctaccaag  13320
gtactgtgat atggcatatg agaaatgatt tttacgtcac aatgtcttcc aacccatcct  13380
tacaccttgt ttggggaaaa tgtgtttttt tctaagtttc tattgttttt attttccaga  13440
agggaaaatg gtgcaatgaa aatggtctcc aaataactgt ggcatcataa aattcttgat  13500
tatattatct ctcatgtcca tgtttggctg ggattaattc tcgggaaaaa attgcttatt  13560
tttataataa aagctcattt tgaaacttgg caaaactaag gaattatttc tcaaaaatac  13620
atacgtatgt tcattactct gatattgcat cttttggtat taatctatga tgttcaattt  13680
tcaacaggaa attatgtaca agaagttgct ctatgcaatc agtgagggcc agggatcctt  13740
tgatttatca tgagtttctg aaactaacca accttaccct gcatgttaat agatggatca  13800
gggtttattg actttattct cgagggtcag ttgttttttt tggttggatg tgctttgctc  13860
ctcgcttctc gaataatagt gtctcatttt ccgtgctcaa tgcaaattgc aaggttgtgg  13920
aattattcag gtgagttgac cttttctgcc agtaaggttg tattgatggg attaatcata  13980
tctttctgct gcagcacgtg aataatttgt tactttttttc cctcaaactg gctgggagct  14040
tcttctcatg ttgttctctt ttatttctga catacttata aggatttctc ccataaattg  14100
cagttgaatc gggtcgccac attttcaaag tgtaggggaa tttacggagc tcttatttga  14160
ttttacctgt tagaacttgt aaatagaata gcaatgatga aattttgatt ttcttttttc  14220
```

```
tttttaaaaa agttcattat tctgtttgta attccaatta ttggcaatta gcatgtacga  14280

agaaaaatgg taaagggaaa ggaaataatt taaaatatta tgctttataa tctcattcta  14340

ttacttagtc actagtcatt tgttattgta aaattttgtc aatatcgtca catggggaaa  14400

tatcgctaat gttaaagcga atgacatgaa gcattatatt attgattttc ctacgtttgc  14460

agatttatct ttatgcatta aactaaagta tgttgttaga aacatgactt agatccgttt  14520

gtttcaatct tattttggag gaaaaatgtt ttaattagtt ttttaaaatg agatgttaag  14580

gccttgtttg gggtggtttt tagttttgaa tttttaaaaa taacaattag ttttagtttg  14640

aaaaaattag tttttaaaat atgattagtt tcaaataatt tttttatttt aaagcgtaat  14700

attatactaa aattagttta aaagtgattt tgtgtggtga tgattatagt gcttacgagt  14760

ttaatttatt ttttctttaa agataaaata tttttatttt ttaattttag taaagttgga  14820

tttgtattta taaaagatga tcccgtgatt ataaaaggaa ggagggagga aaaagtgatt  14880

gggagtttga attcttccaa tgacattcaa aatgtgtaat gtatgatatc cttgctaaat  14940

gattaaaaag tgattgttag gactagatat tttaaattgt gaagctagtt ttaaaagtag  15000

aaagcatatc aaataaaaag tttaaaaagc tgtttttttt tttttgcaat ttagtttgat  15060

aatttattct tattttgaaa attgaattga acatatgctt tttttaatat caattcaaca  15120

ttatatatgt tgatttttct tttatatata aattacttta ttttaatcta actcacgact  15180

cagttttgac aatgttaata tgtgattcta tatgcgttag acatttttag ttatggaaaa  15240

ttattagtat ataatattga tttcttgttt ttaaatataa atattaatta ttaatttgtc  15300

agtgaaaatg atttaaatat ataaactctt tttttcctcc ttcttaatca ttaatcatta  15360

agttaatctt ataatttctt aatatttaac attcggtaac atataaacta actgattgtg  15420

attggtttgt tatattttat aaaaagagtt tataatgtag ttataatcag tgttttcttt  15480

aactagttta tatgaactaa ttgatttttt ttttattctt ctatgactgg gattgtgatt  15540

taattagtta ttagatttta tactctgcaa aattatttca ttagttatca aattaaatta  15600

ttttaaaagt tataattttt tttttaaaag ttaataacta ttgaactgat caatcaaata  15660

aaagaagtta aaaaatgttg aactgatcaa tcaaatagta aaatattttt ttgatatata  15720

tttttgttag aaagtattct tcttgactaa gtatggttat caaactcttg agttaacttg  15780

ttaattctta cgagttttcg agtatgtgag ttgattcgtg tgtaaactat ttttttagta  15840

gattattggt agattagata aactctaaat aaactcttgc gtttatcatg gagtcaacga  15900

gtcagcaagt taaaaaaatt aaaccaaaat ataagtcatt ttacctccat ttagtgtgtt  15960

gctcctgaat taaaaaatta tcacctctaa taacatcaaa cccttgttct caaataacat  16020

caaactcttg ataagaatgc tctaccacta ttataacatc cacaagttat tatttagtag  16080

tgatgcatta ctagacttgg ttagctaagt attgtgaaat tcatgattta ctactttact  16140

ttattatatt tttgaaatgt ttaattgaca tgttatttat agatattttg ttattatttt  16200

tatatgaagt ggactcttac gagtctatga ttaagtatac gagtcaaatc tatgaaactc  16260

ttacaaattt acgtaaactt tcgagtttga taacctttaa ctcaattatt atctatagca  16320

ttagctcttt tcaaatattt aaatttgttg tatattcatg attcaagatc tttgattaag  16380

atagagtatt cttactcaca agttgattcc cctatgtaat caaagcttag             16430
```

<210> SEQ ID NO 6
<211> LENGTH: 16431
<212> TYPE: DNA
<213> ORGANISM: Glycine max

<400> SEQUENCE: 6

```
atggaaaact cgaaatcaag ggtttcaaag taataggagg tacaagaaaa gcttgcaaat      60
ccatcacccg agagaatata aaactcttag aaccaagaaa catctaactt cccctaacct     120
tacaccgtat tttactttca caataaaaaa taattacctg gatagttgct ttcaacccaa     180
atttcttaag agcaacaatg gcattaggat ttccagccca ttttacagaa gactccataa     240
ttaactcttt ttcgtcagtc tcataaactt tcattcttat tgagaataaa ttatgcattc     300
aataagaaaa atggaaaaat tcacatagaa tcacaaataa gttagtaaaa aatagaataa     360
ttgcatttat aaaacaaaca cataagtatt ttgtaggggt cataaagttg acttagtggt     420
gatataaaaa aagagaatag agagattgta tacattaatt cttccactaa caaaaaatga     480
acaactaata tttatcaata aaaaaagtat acgtgatatt tttttttttt taaagagata     540
aaccatttta acaaaaaaaa tattttataa gggttccttt taatgagtga agcccaaaac     600
aagatcttat ggtaaaatgc atcatttgat agatcaaagt ttctttaaac tctaaataaa     660
attcatacca gtatgggttt caaaccttaa taattatcaa ataccagtaa tgtaattgat     720
tttagagatg cagtaaaaac aaatgaaaat tgaactgtct taatatttga tgtattattt     780
tcgaaatgaa tatttgatat attattaaag atgtatttta tgagtattta agatgtttta     840
ttgttctttc aaattaaaac catcttgtta attgttagtt tattacattt ctcccaaaaa     900
aacatgattt atcattagaa ccaaaaataa tttctaaatt gtgatttgta tcctttacag     960
atgataaaaa cgagtgaaat ttaggtatta tcatagttta cacattggta atatttatat    1020
tatttgtgca aaccagtaaa aagtttttat ctaataataa accacatcta aataaactaa    1080
ccttgaaaag ttggcggcaa agaccctagt gagctcttca aactcaacag aatcaatttt    1140
atatttcggt atttgctcat caattattgg ttttgcaata ttctttgcag tcttgcatat    1200
tgcctaaatg aaaaaaccca atcaaacaat cacacaaaaa agaagaaaaa atacatgcta    1260
cttgataatt gtccgaaaat ataataaaac ataccttttc aaggtatggc cacatatatt    1320
caataagctt gttaagccaa tcaaccttca taaaaacacc aataaataat agtgtggttg    1380
ttaaaatact tgtggagtgt gtttggatga gaaattttaa attctaaaaa ttttaaatac    1440
ttcaattcaa attcttttat tttcaaaatt ttgtgtttgg ataaaaaaaa attaaaattg    1500
tgagggtgaa agaaaatgaa tgcaaagaga aaaaaaaata tggttagtgt gcttctaaag    1560
agaagaatat tgatgtgcca tggggagtcg cacggaaacc gggatacaat gacgtacacc    1620
atcatatccg accacaacat taagtcaacg gcgcaaggca tggcccagac ctttcgcacc    1680
gacgagcacc tctatcgcgt gatagacaac gataattgtt cccctgattg gcaccgttct    1740
atgtgtctcc ctatatccgc acccgatcga tgctccgcgt gagctcagac agtgtttcat    1800
gaagtagaga attatcgacg taaggaaaga ttcacgagtt cgagaacgag atttcaaact    1860
caggtgaacg agaggatgaa gatgataaag gaaatataca aacattttgg aatattctct    1920
tatcaagaag agaattttaa tttctcactt ttgaaaaaaa attaaaattt cacattttta    1980
gttgtttaaa attctgtttt aaaattttaa attctccata aaaaaaacat ccaaataatg    2040
aattttaaat taaaaaaatt taaattttct gataaattac ttttcttagt taaaattcgt    2100
agtgcatttt acatattaac aaagagtaac ccattgcttt cccgatcaaa gtctggattt    2160
ttttatccaa aggggtatct caggaatcat tccctgtaaa gttttcgagt cttcctccgc    2220
caatggctgg atatcaggat cctatccaag ccaacaatgt attggtgcaa tacttaaaaa    2280
```

```
atgcattaaa aatgtcaaaa tttcaaagat tcacaatcaa ttttcttttt tgattgcttt   2340
ttgacgtata taatagtgtg gcgttaccta ttttaaactt tttttcttat ggttagtgaa   2400
gttactaaag acaaaaatat ttagattcca agataatgtg taagataagg attattataa   2460
tttatgatca taatttacaa aaacttgtta gagaacattg attagcttgt aaaagaaaat   2520
aaaacaaaca aaattagacc cagacattat ctaaaggaaa gagaaaggtt tacaacgggg   2580
tggaatacaa aacaagataa tttgttaaga accatgtttt gtttgtacca tgtaccttaa   2640
cttcagtgga ttgaacgtaa ataaagagaa aataaccaat aacgagaccc atagaaatcc   2700
caaatccaaa tccaaaatga ccaaatatag tgctaaagaa atccatctca gttcttaatt   2760
ttgttttcag accaaacttg ctctgatgac aatcacaatc tctttctctc tccgtgtgct   2820
aaaagtaaaa ttattatgca aatccgttac ttccgatgtc tttgagttct cctcggatca   2880
ccattcctat attcaaacca aaacatgtaa tgcaaatcat tttgacccaa aaaaagacta   2940
tttatacaaa aaaaaaagtt atggttatta ctaaggattt aacacaaatg attacgttat   3000
tcttattaat taaagttact accactattt ttttggagtg acactaccac ataatttgtt   3060
tattcatgtt attatatatt tgaggaaaag tcataaataa attatataat gaataaaaat   3120
aaaataaaat atttaaaaat taaacatgtt actacattat ctttaacata ttttctctat   3180
atttttatgt tacaaaaaat tgtataatat ttaagaaaac aaaaacacta ttaaacacat   3240
agatcaattg atttaaaact attaaagttt aagtaatatt ttcgaattcg aattctatat   3300
atgttacggc atgaaatact tgtaggaaga attagatgct tgtggtctct aaaaaaaact   3360
tccctccctc aaaattttcc ctatggaatg tgaatttttt tgttgggtga tacaaaaatg   3420
attatgtttt ttctttacct ctttatttaa taaatagtaa aattttgatg ttctttcctt   3480
ttatttatca tttttttcctt tttattaaac caaacaataa ctgagaggag gaatggggaa   3540
gtagcaattt ggattattct tttcttgttt ttttttttaaa ataaaaaaca taacataaaa   3600
taaaaaatta attttgatgc attgttagtt gaaagatgat tattattata tattaaaagt   3660
taaataataa taataaataa tttatgttaa tttttaatct accaaattat tttaatttaa   3720
atattatttt ctgttttact ttatttatgt tgaatctacc aatatttatt tctcccccac   3780
cacccccatt ttttacatca acatagatta aaacggatag aatttgtagt ggaagattaa   3840
ataaaattga ttaataaaat atatgtatgt ttctgggggga caagtattta aatttaaatt   3900
tgataagata tgggtgatat gaaatgtagt aattttcaat gagccgaaaa cgacgcggag   3960
gcagcaagcg agttctcact tagagtgttg ttgttgtgca aacaaagtta agttacgtat   4020
aaaaggggta tttgatatct ctgtcttttt attctctccc tctcgctcct caccttaggg   4080
ttttcatgca acaatttcct cctcctcctc ctctctctct ctctctctac actagattgg   4140
ggattttcct tggatttagg gtttccgccg attttgattt taatttaata catttgtctg   4200
agatgcaacg gattaatcca atcgatcgat cggggatagg tgagacaaat tgaagggtga   4260
gtgtgggttt tgtatggaaa ctcggagtcg gaagcgggcg gaggcttcct cagctgcccc   4320
ttcatcctcg tccaccaccc cttctcgttc agccaagcgc tctcgtcttt cttcttcttc   4380
ttcttccatc ctacctgtta atacacgttc tcgttccgcc aggaataaca acaacaacaa   4440
caactccggt tccatttctt tcatggaccc caccaatgaa tcctccgggt cccgacgtga   4500
tcgccgtggc aagaatttcg atagggaaaa ttcggacaaa gggaaggaga aggaacagga   4560
tgttaggatt agggatgcgg agcgggagcg agagcgagcc ttggcgttaa acatggagag   4620
tgaagatgtt ggggatgacg atgataatga tagtgacggc ggtgtgggaa ttctgcacca   4680
```

-continued

```
gaatttgacg tctgccagta gtgcccttca agggcttctt cggaaacttg gtgctggttt   4740
ggatgatttg cttcctgcta ctgctatggg cggttctgcg tcatctcctc atcagagtgg   4800
cagactcaag aagattttgt ctggcttgcg tgccgatggg gaagaaggtc gtcagggttg   4860
aggcattgac gcagctttgt gacatgctct ccattggcac tgaagattcc ctcagcacat   4920
tttcggttga ctcatttgtt cctgtgctag tgggcttgct taatcacgag agcaatcccg   4980
atgtcatgct tcttgcggcc agggcgctaa cccatttatg tgatgtgctt ccttcatcct   5040
gtgctgctgt tgtgcattat ggtgctgtct ctatcttctg tgcgaggctg ctcaccatag   5100
agtatatgga cttggctgag caggttattt tctcagtcaa tctcttttgt gcctttactt   5160
attatgtatc tgtgtcttac gatgtatgag cttcctaagt ccttaaccct tagttgttga   5220
aaatgggctt ccgtcttaaa cgaggttctt atcatttgac acaccttacg gttttctact   5280
ttgaattctg atagttgtga ttgttgatgt gaacagtctc ttcaagcact aaagaagatt   5340
tctcaggagc acccaactgc ctgtcttaga gctggagctc tgatggctgt tctttcttac   5400
ttggacttct tctcaacagg agttcaggta actaatcaat gaaatcctaa catcaaaggg   5460
tgacaattca ttttgcgttt accacccttg attagcaagc ctatattgac ataatcatgt   5520
gtttcagcgg gtggcattgt ctactgctgc aaatatgtgc aagaagcttc ctcctgatgc   5580
agctgacttt gtgatggaag ctgttccact tttgacaaac ctccttcagt accacgactc   5640
caaggtaagg catgtttgct tgtcatattt gtcataaaat gaaaactgca ctttccttgt   5700
cattccttcc ttttaaggaa attttgtttg tgtaaatatt gatccctaca actgatgttg   5760
tcaattatct atttgcgttt tcataataaa aaacttcgta ccccattgtc cagaggctct   5820
tcactatgcg aaggtatggg ggagggatgt tgtacgcagc cttacccttg cattttcata   5880
atattcaatg ttaatttttg taggtcctgg aacatgcctc tgtttgtttg acacgaatag   5940
ctgaagcatt tgcatcatct ccagacaaat tagatgaatt gtgcaatcat ggactggtaa   6000
cacaagctgc ctctctcatt tctaccagca gttctggagg tgggcaggct tctctcagca   6060
ctccaacata tactgtaagt gcaatctttg ccactaaatc tgatactttt atcctttggt   6120
gggttgttcc tttgacttca ttggtgcatg cagggtttga tccgccttct ttccacatgt   6180
gcaagtgggt ctcctcttgg agctaaaacg ttgcttctcc ttggaactag tggcattctt   6240
aaagatatac tatccggttc cggtgtttct tctaacacct ctgtttcgcc tgcattgagt   6300
aggccagcgg atcaggtatg tgtacttttg agttctttat gtctgttata tgtagttggt   6360
atctctatag ttcatttgat agattgtgac atcgatctca ttatttaaat ccttgaaaac   6420
ttttcagttc cctttttgtg aaagatgagt ttttcctaat tctctttcct aatatttaga   6480
tatttgagat tgtgaacctg gcaaatgaac ttctgcctcc attgcctcaa ggaaccattt   6540
cccttcctgt cagctccaac ttgtttgtga aagggtctgt tgtgaaaaaa tcctcttctg   6600
gcaattctgg gatacaagaa gacacaaatg gaaatgttca tgagatattg gctcgtgaga   6660
aattattaaa tgatcagcct gagttacttc agcaatttgg gatggatctc ctcccagttt   6720
taatgcaggt tcaatgctta aatttactta attgttaaaa tgctcaaatt atattttgtg   6780
atttgtttat taatttttaa cttcttaaat aaataactgg ctctattttt tatatcctcg   6840
acttcttcat tccttcactc ccgtcactta ttactagttt tgtcttgctt ttgaaacaga   6900
tatatggtgc tagcgtcaat ggtccagttc ggcacaaatg tctttctgtc attggaaaat   6960
tgatgtattt cagcacagct gagatgatcc agtctttact gagtgtaaca aatatatcaa   7020
```

-continued

```
ggtatctaga acttcaattg ggttgctgtt gctctatgtt ctctgtagaa tacttatgca   7080
ttgtcacttt gatgatatag tttcttagct ggtgtgttag catggaaaga tccacatgtt   7140
ttggttcctg ccttgcaaat ttcggaaatt cttatggaaa agcttcctgg aaccttctct   7200
aagatgtttg tcagagaagg tgtggttcat gcagttgacc aacttatttt ggctggaaat   7260
tcaaccaata tatccacaca aacatcatct gctgagaagg ataatgattc tgtatctgga   7320
acttcatctc gctctagacg ctatcgcctg cgcagtggta attcaaatcc cgatgcgaac   7380
ccttcagatg atttaaagag tccagttcca gtaaatgttg gtttgccacc aagttctgta   7440
gaaactccaa caactaattc tagtatccgt gcatctgtta gctcagttgc tagagctttt   7500
aaagacaagt actttccttc tgatcctggg tctgttgaag tgggtgttag tgatgatctt   7560
ttgcatctga aaaatctatg cacgaagttg atcactggtg ttgatgacca aagaagcaag   7620
gcaaagggaa aagttaaagc ttctggattt ggtctggatg ataattctag taacacagaa   7680
gagtatttga ttggggtgat atctgacatg ctaaaggaac ttggcaaagg agatagtgta   7740
tctacttttg aatttatcgg tagtggtgtt gttgaagcct tgctaaatta tttttcttgt   7800
gggtatttct ctaaagatcg aatatcagaa accaatctcc ccaagcttcg ccaacaggca   7860
ctttcaaggt tcaagtcatt tgtagctgtt gcactacctt tgagcattga caatggggct   7920
gttgctccta tgactgtctt agttcagaag cttcaaaatg cgttggcctc cttggagcgt   7980
ttccctgtta tgctgagtaa ttcatctcgg tcatctagtg gaagtgcacg tctctcctct   8040
gggctaagtg cattatctca gcccataaaa ttacgtctct gccgagccca gggtgaaaag   8100
tcacttaggg attattcatc caatgtggta ctgattgatc cattagcaag tctagcagcc   8160
atcgaggaat ttctatgggc tcgtgtccag cgtggtgaat ctggtcagaa gtctactgta   8220
ggcactgaaa attctgaatc tggaacaact cctgctgggg caggtgtttc atctccttcc   8280
tcttatactc cctccactgc ccatcgtcat tctactagaa ccagatcatc tgttaatata   8340
ggagatacac ctagaaaaga aacatctcaa gacaaaggaa cgagctcatc aaagagcaag   8400
ggtaaagctg tattaaaacc tgcgcaggag gaagcgcaag gaccccaaac aaggaataca   8460
gtgcgcagaa gagcagctct tgataaagtc gctcaaatga aacctgcaaa tggcgactca   8520
acttctgagg tatgctgcta aattctggga acgagtcata ataattaaat aatattaatc   8580
taaattggtt tataacattg aataatttaa tctttgttgg attttgttta tacttatgct   8640
tattctcctt ccctcttttt gttagataaa aaaccattgg tgagatttct tcatctaata   8700
gttagttgat gttggctttt attttactgc tttggattaa aatgatgctt tcagttgacg   8760
tgtctcctgt agcatcttaa acttgagtgg tggcttttat tatttaagtc atttttattg   8820
tttgacatta ttttcccctg cttttatggg ataggatgaa gaattggata tatctcctgt   8880
tgaaattgct gaggctttgg tgattgaaga tgatgatatt tctgatgatg aggatgaaga   8940
ccatgaagat gtatgtttct tcttctgcta agatttcatc ttattgttgt gattactttt   9000
attcatatct catttgtga tctaaattgt aagatctcac aatcttgctg ccactttcct   9060
ttctgaatca cttgtaaaat cttaaatgag ttcgttgtga gatttcaaga ttgctgaact   9120
ggtgagattg tgtaatcatg tgcagtccaa aaatctgtca atttcgagtt atgtttcaag   9180
tattttcttt tgtgacttct ggttgtgtta tgtatgtgac taattatgac ttgttttgga   9240
tgttatggtt atgaaatttc aaggctaagt ttgctataat gttatctata tttttctttc   9300
atattttcta tgcatacata aacctatata attttttggt aggattttat gatctacatt   9360
ttacaatttt gcatccccct tccaatctta ggtagaatct caatcttgac aacattggtt   9420
```

```
gttaccaata ttgaaaacta tcatttaggc gcatccattc ttgcaattga gttttaccaa   9480
atagaaatgt tattgttgtt tccaagaatg gatactacca ttaattgttg tttagattgg   9540
atattatgat ttggtttagc tgttctgttc tagctattga attttatcaa atagaaatgg   9600
tactattgtt tcttatattt ttaataatca ttaattgatg attccaagat tggatgctat   9660
catttgattc agttgcatcc atgctagtaa ttgaatttat gatattattc cactaaccat   9720
catctaatgc atcatcagct tgttttattt attttatttt attttatttt atttttgagc   9780
aggtgctgag ggatgattct cttcctgtct gcttgcctga caaagtgcat gatgtgaaat   9840
tgggtgactc agctgaggag agtactgttg ctccagcaac aagtgatagc cagactaatg   9900
cagcctcagg ttcaagcagc aaagctggta cagccagggg ttctgactcc gctgatttta   9960
ggagtgggtt ttcatctagc tcaaggggtg caatgtcatt tgctgctgct gctatggctg  10020
gacttggata tgctaatagc agaggtttca ggggcggcag agataggcat gggtgcctgt  10080
tgtttggtag ttctaatgat cctccgaagt tgatttttac tactggtggg aagcagctta  10140
ataggaatct gagtatatat caggcaattc aaagacagct tgtgctagat gaagatgatg  10200
atgagagatt tgctggcagt gactatgtat ctggtgatgg aagcagtctg tggggtgata  10260
tttacaccat cacttatcaa agggcagaaa accagccaga taaggcgtct actggaggat  10320
caagttcaaa tacttcaaaa tctgccaaat ctgggtctgc cttaaattca agctcagaag  10380
ctaaattgca tcagacatct gttctagaca gtatattgca gggagaattg ccatgtgatc  10440
tagagaaatc taatcccacc tacaatattt tggcactcct gcgtgtgctg gagggtttca  10500
accaacttgc gcctcgtttg agggtcctaa tggtttctga tagctttgcc aagggaaaaa  10560
tcttggattt agatgagcta tgtgttacaa ctggtgctag ggtgcttcta gaggaatttg  10620
taagtggtaa gcttactcca aaattggcta ggcaaataca agatgccctt gcactatgca  10680
gtggtaatct tcccttatgg tgttaccagt tgactaaagc gtgccctttc ttgtttcctt  10740
ttgagacccg acgacagtac ttttattcta ccgcatttgg gttatctcgt gcactgtatc  10800
gacttcaaca gcagcaaggt gctgatggcc atggttcaac aactgagagg gaggtgagag  10860
ttgggagatt gcagcgccaa aaggttcgtg tctctcgaaa tcgtgtcctg gattctgctg  10920
caaaagttat ggagatgtat tctagccaaa aagctgtact tgaagtagaa tattttggtg  10980
aagttggcac tggtctgggt cccacccttg agttttatac aattctaagt catgatttgc  11040
aaaaagttgg actgcaaatg tggagatctt attcttcaga caaacatcaa atggaaatag  11100
atggagatga aaagaaaaag aaaagtgaag gctctgggcc taatttggct ggagatggag  11160
aacttgttca agctcctctg ggttgtttc ctcggccatg gcctacaaat tctgatgctt  11220
cagagagtag ccagttttca aaagtcattg agtatttccg gctactaggt cgtgttatgg  11280
ctaaagctct tcaagacgga cgactactgg acctgccatt gtcagtggca ttttataagc  11340
ttgttctctg ccaagtatgt tgtgcaatat tgatgtttta accattttca tttttattg  11400
ttaatctgat ggtcaattta ttctagtcaa tgaacctaac cttcactttg tggcaggatc  11460
ttgatttgca tgacattctg ttcattgatg ctgagcttgg gaagacttta caagagttca  11520
atgcccttgt ttgtcggaaa cattatatag aatctattgg tggtagctat acagatacaa  11580
ttgttaactt gtattttcat ggtgcaccaa tcgaagatct ttgcttagat tttactctcc  11640
ctggttatcc tgaatacacc ttgaagccag gagatgaaat tgtatggagt taaaccctga  11700
gctagtctat agatcttggt tcttctgtta tgaaaatttc ctttaactta ctctcaaatt  11760
```

-continued

```
ctcaggttga tatcaacaat ttggaggagt atatatcctt ggtgatcgat gcaactgtca  11820
agactggaat catgcggcaa atagaagcat ttagagcagg gtttaaccag gttttatgct  11880
gttcttaata attagtaatt taactttaaa tgtacacatt gttggtgtgg agcatgttat  11940
ttttctaaaa caaggtgttt ccctctcccc tttctagtgg aaagtatctt ttattgacat  12000
tatcctcctt gtctatatat gctcccatac ttatctccca ctgcatccct gagaatttgt  12060
tttttaaccg tgcttaatgg tgttgttaga tccacgtagc tgacatctcc ttgtgggata  12120
agattattgt agttgtagat tggaattagt ttacctgatg catgacatta atttgttaac  12180
atgccattga aattcttaag tgacattctg tctcactaaa agttatttgg tgttttaccg  12240
agatcttaaa tatctttcct ttatctctca tgcttgaata ttccacttgg gatcttataa  12300
aatatatgat cctgttcttt tacttacatt ggctcccaat caccaactat actttccctg  12360
tacaaaatgg aaattgcaag attcagttat tggatgttaa actttttaca ttctgaatat  12420
attgtttgtg aaatgggtgg ggtagttatg gctctgctag actctcttgt ggaggatgag  12480
aagaggatat tgatggggaa attagttact tttggctcat tttatttagt tcaaaactaa  12540
acatcacttg tatgcttgtg ctgtttaatg caggtttttg atatctcatc tttacaaatt  12600
tttactcctc aagaactaga taatttgctt tgcggccgca gggagttgtg ggaggtgatt  12660
tttgcccaat tatattattg cttttaatat tagttaaaat attagattta gaacaaggca  12720
ttgaaattaa aagtttttttg tttttaatct tactgcaggc tgagacactt gctgatcata  12780
taaaattcga ccatgggtac aatgcaaaga gccctgccat tgttaatgta tgttttttttc  12840
ctcctaatta taagtaatat tgtgtattat agaaaattag agctagttat aatttatgat  12900
gcttgtcctg ttggatgcta ttttagttac ttgaaattat gggagagttc acaccagagc  12960
agcaacgtgc cttctgtcaa tttgttactg gtgcacctag gctgccacct ggagggctgg  13020
cagttctaaa tccaaaacta acgattgtga ggaaggtatt cagaaatgaa tttttgataa  13080
cgtgatattt aggcttattc atctatattt tttttcatat taatttcatg gttatatatg  13140
catgtcaata tttgttatta ccgttgtatt catgccttat tttttggcct tggtgcagct  13200
ttcgtcaact gcagttaata attcatctaa tgggaatgga ccttcagaat cagcagatga  13260
tgacttgcct agtgtgatga catgtgctaa ttacctgaaa cttcctcctt actctaccaa  13320
ggtactgtga tatggcatat gagaaatgat ttttacgtca caatgtcttc caacccatcc  13380
ttacaccttg tttggggaaa atgtgttttt ttctaagttt ctattgtttt tattttccag  13440
aagggaaaat ggtgcaatga aaatggtctc caaataactg tggcatcata aaattcttga  13500
ttatattatc tctcatgtcc atgtttggct gggattaatt ctcgggaaaa aattgcttat  13560
ttttataata aaagctcatt ttgaaacttg gcaaaactaa ggaattattt ctcaaaaata  13620
catacgtatg ttcattactc tgatattgca tcttttggta ttaatctatg atgttcaatt  13680
ttcaacagga aattatgtac aagaagttgc tctatgcaat cagtgagggc cagggatcct  13740
ttgatttatc atgagtttct gaaactaacc aaccttaccc tgcatgttaa tagatggatc  13800
agggtttatt gactttattc tcgagggtca gttgtttttt ttggttggat gtgctttgct  13860
cctcgcttct cgaataatag tgtctcattt tccgtgctca atgcaaattg caaggttgtg  13920
gaattattca ggtgagttga ccttttctgc cagtaaggtt gtattgatgg gattaatcat  13980
atctttctgc tgcagcacgt gaataatttg ttactttttt ccctcaaact ggctgggagc  14040
ttcttctcat gttgttctct tttatttctg acatacttat aaggatttct cccataaatt  14100
gcagttgaat cgggtcgcca cattttcaaa gtgtagggga atttacggag ctcttatttg  14160
```

```
attttacctg ttagaacttg taaatagaat agcaatgatg aaattttgat tttctttttt  14220
ctttttaaaa aagttcatta ttctgtttgt aattccaatt attggcaatt agcatgtacg  14280
aagaaaaatg gtaaagggaa aggaaataat ttaaaatatt atgctttata atctcattct  14340
attacttagt cactagtcat ttgttattgt aaaattttgt caatatcgtc acatggggaa  14400
atatcgctaa tgttaaagcg aatgacatga agcattatat tattgatttt cctacgtttg  14460
cagatttatc tttatgcatt aaactaaagt atgttgttag aaacatgact tagatccgtt  14520
tgtttcaatc ttattttgga ggaaaaatgt tttaattagt tttttaaaat gagatgttaa  14580
ggccttgttt ggggtggttt ttagttttga atttttaaaa ataacaatta gttttagttt  14640
gaaaaaatta gtttttaaaa tatgattagt ttcaaataat ttttttattt taaagcgtaa  14700
tattatacta aaattagttt aaaagtgatt ttgtgtggtg atgattatag tgcttacgag  14760
tttaatttat tttttcttta aagataaaat atttttattt tttaatttta gtaaagttgg  14820
atttgtattt ataaaagatg atcccgtgat tataaaagga aggagggagg aaaaagtgat  14880
tgggagtttg aattcttcca atgacattca aaatgtgtaa tgtatgatat ccttgctaaa  14940
tgattaaaaa gtgattgtta ggactagata ttttaaattg tgaagctagt tttaaaagta  15000
gaaagcatat caaataaaaa gtttaaaaag ctgttttttt ttttttgcaa tttagtttga  15060
taatttattc ttattttgaa aattgaattg aacatatgct ttttttaata tcaattcaac  15120
attatatatg ttgattttc ttttatatat aaattacttt attttaatct aactcacgac  15180
tcagttttga caatgttaat atgtgattct atatgcgtta gacattttta gttatggaaa  15240
attattagta tataatattg atttcttgtt tttaaatata aatattaatt attaatttgt  15300
cagtgaaaat gatttaaata tataaactct ttttttcctc cttcttaatc attaatcatt  15360
aagttaatct tataatttct taatatttaa cattcggtaa catataaact aactgattgt  15420
gattggtttg ttatatttta taaaaagagt ttataatgta gttataatca gtgttttctt  15480
taactagttt atatgaacta attgattttt tttttattct tctatgactg ggattgtgat  15540
ttaattagtt attagatttt atactctgca aaattatttc attagttatc aaattaaatt  15600
attttaaaag ttataatttt ttttttaaaa gttaataact attgaactga tcaatcaaat  15660
aaaagaagtt aaaaaatgtt gaactgatca atcaaatagt aaaatatttt tttgatatat  15720
atttttgtta gaaagtattc ttcttgacta agtatggtta tcaaactctt gagttaactt  15780
gttaattctt acgagttttc gagtatgtga gttgattcgt gtgtaaacta tttttttagt  15840
agattattgg tagattagat aaactctaaa taaactcttg cgtttatcat ggagtcaacg  15900
agtcagcaag ttaaaaaaat taaaccaaaa tataagtcat tttacctcca tttagtgtgt  15960
tgctcctgaa ttaaaaaatt atcacctcta ataacatcaa acccttgttc tcaaataaca  16020
tcaaactctt gataagaatg ctctaccact attataacat ccacaagtta ttatttagta  16080
gtgatgcatt actagacttg gttagctaag tattgtgaaa ttcatgattt actactttac  16140
tttattatat ttttgaaatg tttaattgac atgttattta tagatatttt gttattattt  16200
ttatatgaag tggactctta cgagtctatg attaagtata cgagtcaaat ctatgaaact  16260
cttacaaatt tacgtaaact ttcgagtttg ataaccttta actcaattat tatctatagc  16320
attagctctt ttcaaatatt taaatttgtt gtatattcat gattcaagat ctttgattaa  16380
gatagagtat tcttactcac aagttgattc ccctatgtaa tcaaagctta g           16431
```

<210> SEQ ID NO 7

<211> LENGTH: 16426
<212> TYPE: DNA
<213> ORGANISM: Glycine max

<400> SEQUENCE: 7

```
atggaaaact cgaaatcaag ggtttcaaag taataggagg tacaagaaaa gcttgcaaat      60
ccatcacccg agagaatata aaactcttag aaccaagaaa catctaactt cccctaacct     120
tacaccgtat tttactttca caataaaaaa taattacctg gatagttgct ttcaacccaa     180
atttcttaag agcaacaatg gcattaggat ttccagccca ttttacagaa gactccataa     240
ttaactcttt ttcgtcagtc tcataaactt tcattcttat tgagaataaa ttatgcattc     300
aataagaaaa atggaaaaat tcacatagaa tcacaaataa gttagtaaaa aatagaataa     360
ttgcatttat aaaacaaaca cataagtatt ttgtaggggt cataaagttg acttagtggt     420
gatataaaaa aagagaatag agagattgta tacattaatt cttccactaa caaaaaatga     480
acaactaata tttatcaata aaaaaagtat acgtgatatt ttttttttt taaagagata      540
aaccatttta acaaaaaaaa tattttataa gggttccttt taatgagtga agcccaaaac     600
aagatcttat ggtaaaatgc atcatttgat agatcaaagt ttctttaaac tctaaataaa     660
attcatacca gtatgggttt caaaccttaa taattatcaa ataccagtaa tgtaattgat     720
tttagagatg cagtaaaaac aaatgaaaat tgaactgtct taatatttga tgtattattt     780
tcgaaatgaa tatttgatat attattaaag atgtatttta tgagtattta agatgtttta     840
ttgttctttc aaattaaaac catcttgtta attgttagtt tattacattt ctcccaaaaa     900
aacatgattt atcattagaa ccaaaaataa tttctaaatt gtgatttgta tcctttacag     960
atgataaaaa cgagtgaaat ttaggtatta tcatagttta cacattggta atatttatat    1020
tatttgtgca aaccagtaaa aagtttttat ctaataataa accacatcta aataaactaa    1080
ccttgaaaag ttggcggcaa agaccctagt gagctcttca aactcaacag aatcaatttt    1140
atatttcggt atttgctcat caattattgg ttttgcaata ttctttgcag tcttgcatat    1200
tgcctaaatg aaaaaaccca atcaaacaat cacacaaaaa agaagaaaaa atacatgcta    1260
cttgataatt gtccgaaaat ataataaaac ataccttttc aaggtatggc cacatatatt    1320
caataagctt gttaagccaa tcaaccttca taaaaacacc aataaataat agtgtggttg    1380
ttaaaatact tgtggagtgt gtttggatga gaaattttaa attctaaaaa ttttaaatac    1440
ttcaattcaa attcttttat tttcaaaatt ttgtgtttgg ataaaaaaaa attaaaattg    1500
tgagggtgaa agaaaatgaa tgcaaagaga aaaaaaaata tggttagtgt gcttctaaag    1560
agaagaatat tgatgtgcca tggggagtcg cacggaaacc gggatacaat gacgtacacc    1620
atcatatccg accacaacat taagtcaacg gcgcaaggca tggcccagac ctttcgcacc    1680
gacgagcacc tctatcgcgt gatagacaac gataattgtt cccctgattg gcaccgttct    1740
atgtgtctcc ctatatccgc acccgatcga tgctccgcgt gagctcagac agtgtttcat    1800
gaagtagaga attatcgacg taaggaaaga ttcacgagtt cgagaacgag atttcaaact    1860
caggtgaacg agaggatgaa gatgataaag gaaatataca aacattttgg aatattctct    1920
tatcaagaag agaattttaa tttctcactt ttgaaaaaaa attaaaattt cacattttta    1980
gttgtttaaa attctgtttt aaaattttaa attctccata aaaaaaacat ccaaataatg    2040
aattttaaat taaaaaaatt taaattttct gataaattac ttttcttagt taaaattcgt    2100
agtgcatttt acatattaac aaagagtaac ccattgcttt cccgatcaaa gtctggattt    2160
ttttatccaa aggggtatct caggaatcat tccctgtaaa gttttcgagt cttcctccgc    2220
```

```
caatggctgg atatcaggat cctatccaag ccaacaatgt attggtgcaa tacttaaaaa   2280
atgcattaaa aatgtcaaaa tttcaaagat tcacaatcaa ttttcttttt tgattgcttt   2340
ttgacgtata taatagtgtg gcgttaccta ttttaaactt tttttcttat ggttagtgaa   2400
gttactaaag acaaaaatat ttagattcca agataatgtg taagataagg attattataa   2460
tttatgatca taatttacaa aaacttgtta gagaacattg attagcttgt aaaagaaaat   2520
aaaacaaaca aaattagacc cagacattat ctaaaggaaa gagaaaggtt tacaacgggg   2580
tggaatacaa aacaagataa tttgttaaga accatgtttt gtttgtacca tgtaccttaa   2640
cttcagtgga ttgaacgtaa ataaagagaa aataaccaat aacgagaccc atagaaatcc   2700
caaatccaaa tccaaaatga ccaaatatag tgctaaagaa atccatctca gttcttaatt   2760
ttgttttcag accaaacttg ctctgatgac aatcacaatc tctttctctc tccgtgtgct   2820
aaaagtaaaa ttattatgca aatccgttac ttccgatgtc tttgagttct cctcggatca   2880
ccattcctat attcaaacca aaacatgtaa tgcaaatcat tttgacccaa aaaaagacta   2940
tttatacaaa aaaaaaagtt atggttatta ctaaggattt aacacaaatg attacgttat   3000
tcttattaat taaagttact accactattt ttttggagtg acactaccac ataatttgtt   3060
tattcatgtt attatatatt tgaggaaaag tcataaataa attatataat gaataaaaat   3120
aaaataaaat atttaaaaat taaacatgtt actacattat ctttaacata ttttctctat   3180
atttttatgt tacaaaaaat tgtataatat ttaagaaaac aaaaacacta ttaaacacat   3240
agatcaattg atttaaaact attaaagttt aagtaatatt ttcgaattcg aattctatat   3300
atgttacggc atgaaatact tgtaggaaga attagatgct tgtggtctct aaaaaaaact   3360
tccctccctc aaaattttcc ctatggaatg tgaatttttt tgttgggtga tacaaaaatg   3420
attatgtttt ttctttacct ctttatttaa taaatagtaa aattttgatg ttctttcctt   3480
ttatttatca ttttttcctt tttattaaac caaacaataa ctgagaggag gaatggggaa   3540
gtagcaattt ggattattct tttcttgttt tttttttaaa ataaaaaaca taacataaaa   3600
taaaaaatta attttgatgc attgttagtt gaaagatgat tattattata tattaaaagt   3660
taaataataa taataaataa tttatgttaa tttttaatct accaaattat tttaatttaa   3720
atattatttt ctgttttact ttatttatgt tgaatctacc aatatttatt tctcccccac   3780
cacccccatt ttttacatca acatagatta aaacggatag aatttgtagt ggaagattaa   3840
ataaaattga ttaataaaat atatgtatgt ttctggggga caagtattta aatttaaatt   3900
tgataagata tgggtgatat gaaatgtagt aattttcaat gagccgaaaa cgacgcggag   3960
gcagcaagcg agttctcact tagagtgttg ttgttgtgca aacaaagtta agttacgtat   4020
aaaaggggta tttgatatct ctgtcttttt attctctccc tctcgctcct caccttaggg   4080
ttttcatgca acaatttcct cctcctcctc ctctctctct ctctctctac actagattgg   4140
ggattttcct tggatttagg gtttccgccg attttgattt taatttaata catttgtctg   4200
agatgcaacg gattaatcca atcgatcgat cggggatagg tgagacaaat tgaagggtga   4260
gtgtgggttt tgtatggaaa ctcggagtcg gaagcgggcg gaggcttcct cagctgcccc   4320
ttcatcctcg tccaccaccc cttctcgttc agccaagcgc tctcgtcttt cttcttcttc   4380
ttcttccatc ctacctgtta atacacgttc tcgttccgcc aggaataaca acaacaacaa   4440
caactccggt tccatttctt tcatggaccc caccaatgaa tcctccgggt cccgacgtga   4500
tcgccgtggc aagaatttcg atagggaaaa ttcggacaaa gggaaggaga aggaacagga   4560
```

-continued

```
tgttaggatt agggatgcgg agcgggagcg agagcgagcc ttggcgttaa acatggagag   4620
tgaagatgtt ggggatgacg atgataatga tagtgacggc ggtgtgggaa ttctgcacca   4680
gaatttgacg tctgccagta gtgcccttca agggcttctt cggaaacttg gtgctggttt   4740
ggatgatttg cttcctgcta ctgctatggg cggttctgcg tcatctcctc atcagagtgg   4800
cagactcaag aagattttgt ctggcttgcg tgccgatggg gaagaaggtc gtctgaggca   4860
ttgacgcagc tttgtgacat gctctccatt ggcactgaag attccctcag cacattttcg   4920
gttgactcat ttgttcctgt gctagtgggc ttgcttaatc acgagagcaa tcccgatgtc   4980
atgcttcttg cggccagggc gctaacccat ttatgtgatg tgcttccttc atcctgtgct   5040
gctgttgtgc attatggtgc tgtctctatc ttctgtgcga ggctgctcac catagagtat   5100
atggacttgg ctgagcaggt tattttctca gtcaatctct tttgtgcctt tacttattat   5160
gtatctgtgt cttacgatgt atgagcttcc taagtcctta acccttagtt gttgaaaatg   5220
ggcttccgtc ttaaacgagg ttcttatcat ttgacacacc ttacggtttt ctactttgaa   5280
ttctgatagt tgtgattgtt gatgtgaaca gtctcttcaa gcactaaaga agatttctca   5340
ggagcaccca actgcctgtc ttagagctgg agctctgatg gctgttcttt cttacttgga   5400
cttcttctca acaggagttc aggtaactaa tcaatgaaat cctaacatca aagggtgaca   5460
attcattttg cgtttaccac ccttgattag caagcctata ttgacataat catgtgtttc   5520
agcgggtggc attgtctact gctgcaaata tgtgcaagaa gcttcctcct gatgcagctg   5580
actttgtgat ggaagctgtt ccacttttga caaacctcct tcagtaccac gactccaagg   5640
taaggcatgt ttgcttgtca tatttgtcat aaaatgaaaa ctgcactttc cttgtcattc   5700
cttcctttta aggaaatttt gtttgtgtaa atattgatcc ctacaactga tgttgtcaat   5760
tatctatttg cgttttcata ataaaaaact tcgtacccca ttgtccagag gctcttcact   5820
atgcgaaggt atgggggagg gatgttgtac gcagccttac ccttgcattt tcataatatt   5880
caatgttaat ttttgtaggt cctggaacat gcctctgttt gtttgacacg aatagctgaa   5940
gcatttgcat catctccaga caaattagat gaattgtgca atcatggact ggtaacacaa   6000
gctgcctctc tcatttctac cagcagttct ggaggtgggc aggcttctct cagcactcca   6060
acatatactg taagtgcaat ctttgccact aaatctgata cttttatcct ttggtgggtt   6120
gttcctttga cttcattggt gcatgcaggg tttgatccgc cttctttcca catgtgcaag   6180
tgggtctcct cttggagcta aaacgttgct tctccttgga actagtggca ttcttaaaga   6240
tatactatcc ggttccggtg tttcttctaa cacctctgtt tcgcctgcat tgagtaggcc   6300
agcggatcag gtatgtgtac ttttgagttc tttatgtctg ttatatgtag ttggtatctc   6360
tatagttcat ttgatagatt gtgacatcga tctcattatt taaatccttg aaaacttttc   6420
agttcccttt ttgtgaaaga tgagtttttc ctaattctct ttcctaatat ttagatattt   6480
gagattgtga acctggcaaa tgaacttctg cctccattgc ctcaaggaac catttccctt   6540
cctgtcagct ccaacttgtt tgtgaaaggg tctgttgtga aaaaatcctc ttctggcaat   6600
tctgggatac aagaagacac aaatggaaat gttcatgaga tattggctcg tgagaaatta   6660
ttaaatgatc agcctgagtt acttcagcaa tttgggatgg atctcctccc agttttaatg   6720
caggttcaat gcttaaattt acttaattgt taaaatgctc aaattatatt ttgtgatttg   6780
tttattaatt tttaacttct taaataaata actggctcta ttttttatat cctcgacttc   6840
ttcattcctt cactcccgtc acttattact agttttgtct tgcttttgaa acagatatat   6900
ggtgctagcg tcaatggtcc agttcggcac aaatgtcttt ctgtcattgg aaaattgatg   6960
```

```
tatttcagca cagctgagat gatccagtct ttactgagtg taacaaatat atcaaggtat   7020
ctagaacttc aattgggttg ctgttgctct atgttctctg tagaatactt atgcattgtc   7080
actttgatga tatagtttct tagctggtgt gttagcatgg aaagatccac atgttttggt   7140
tcctgccttg caaatttcgg aaattcttat ggaaaagctt cctggaacct tctctaagat   7200
gtttgtcaga gaaggtgtgg ttcatgcagt tgaccaactt attttggctg gaaattcaac   7260
caatatatcc acacaaacat catctgctga gaaggataat gattctgtat ctggaacttc   7320
atctcgctct agacgctatc gcctgcgcag tggtaattca aatcccgatg cgaacccttc   7380
agatgattta aagagtccag ttccagtaaa tgttggtttg ccaccaagtt ctgtagaaac   7440
tccaacaact aattctagta tccgtgcatc tgttagctca gttgctagag cttttaaaga   7500
caagtacttt ccttctgatc ctgggtctgt tgaagtgggt gttagtgatg atcttttgca   7560
tctgaaaaat ctatgcacga agttgatcac tggtgttgat gaccaaagaa gcaaggcaaa   7620
gggaaaagtt aaagcttctg gatttggtct ggatgataat tctagtaaca cagaagagta   7680
tttgattggg gtgatatctg acatgctaaa ggaacttggc aaaggagata gtgtatctac   7740
ttttgaattt atcggtagtg gtgttgttga agccttgcta aattattttt cttgtgggta   7800
tttctctaaa gatcgaatat cagaaaccaa tctccccaag cttcgccaac aggcactttc   7860
aaggttcaag tcatttgtag ctgttgcact acctttgagc attgacaatg gggctgttgc   7920
tcctatgact gtcttagttc agaagcttca aaatgcgttg gcctccttgg agcgtttccc   7980
tgttatgctg agtaattcat ctcggtcatc tagtggaagt gcacgtctct cctctgggct   8040
aagtgcatta tctcagccca taaaattacg tctctgccga gcccagggtg aaaagtcact   8100
tagggattat tcatccaatg tggtactgat tgatccatta gcaagtctag cagccatcga   8160
ggaatttcta tgggctcgtg tccagcgtgg tgaatctggt cagaagtcta ctgtaggcac   8220
tgaaaattct gaatctggaa caactcctgc tggggcaggt gtttcatctc cttcctctta   8280
tactccctcc actgcccatc gtcattctac tagaaccaga tcatctgtta atataggaga   8340
tacacctaga aaagaaacat ctcaagacaa aggaacgagc tcatcaaaga gcaagggtaa   8400
agctgtatta aaacctgcgc aggaggaagc gcaaggaccc caaacaagga atacagtgcg   8460
cagaagagca gctcttgata aagtcgctca aatgaaacct gcaaatggcg actcaacttc   8520
tgaggtatgc tgctaaattc tgggaacgag tcataataat taaataatat taatctaaat   8580
tggtttataa cattgaataa tttaatcttt gttggatttt gtttatactt atgcttattc   8640
tccttccctc tttttgttag ataaaaaacc attggtgaga tttcttcatc taatagttag   8700
ttgatgttgg cttttatttt actgctttgg attaaaatga tgctttcagt tgacgtgtct   8760
cctgtagcat cttaaacttg agtggtggct tttattattt aagtcatttt tattgtttga   8820
cattattttc ccctgctttt atgggatagg atgaagaatt ggatatatct cctgttgaaa   8880
ttgctgaggc tttggtgatt gaagatgatg atatttctga tgatgaggat gaagaccatg   8940
aagatgtatg tttcttcttc tgctaagatt tcatcttatt gttgtgatta cttttattca   9000
tatctcattt tgtgatctaa attgtaagat ctcacaatct tgctgccact ttcctttctg   9060
aatcacttgt aaaatcttaa atgagttcgt tgtgagattt caagattgct gaactggtga   9120
gattgtgtaa tcatgtgcag tccaaaaatc tgtcaatttc gagttatgtt tcaagtattt   9180
tcttttgtga cttctggttg tgttatgtat gtgactaatt atgacttgtt ttggatgtta   9240
tggttatgaa atttcaaggc taagtttgct ataatgttat ctatattttt ctttcatatt   9300
```

-continued

```
ttctatgcat acataaacct atataatttt ttggtaggat tttatgatct acattttaca   9360
attttgcatc ccccttccaa tcttaggtag aatctcaatc ttgacaacat tggttgttac   9420
caatattgaa aactatcatt taggcgcatc cattcttgca attgagtttt accaaataga   9480
aatgttattg ttgtttccaa gaatggatac taccattaat tgttgtttag attggatatt   9540
atgatttggt ttagctgttc tgttctagct attgaatttt atcaaataga aatggtacta   9600
ttgtttctta tatttttaat aatcattaat tgatgattcc aagattggat gctatcattt   9660
gattcagttg catccatgct agtaattgaa tttatgatat tattccacta accatcatct   9720
aatgcatcat cagcttgttt tatttatttt attttatttt attttatttt tgagcaggtg   9780
ctgagggatg attctcttcc tgtctgcttg cctgacaaag tgcatgatgt gaaattgggt   9840
gactcagctg aggagagtac tgttgctcca gcaacaagtg atagccagac taatgcagcc   9900
tcaggttcaa gcagcaaagc tggtacagcc aggggttctg actccgctga ttttaggagt   9960
gggttttcat ctagctcaag ggtgcaatg tcatttgctg ctgctgctat ggctggactt  10020
ggatatgcta atagcagagg tttcagggc ggcagagata ggcatgggtg cctgttgttt  10080
ggtagttcta atgatcctcc gaagttgatt tttactactg gtgggaagca gcttaatagg  10140
aatctgagta tatatcaggc aattcaaaga cagcttgtgc tagatgaaga tgatgatgag  10200
agatttgctg gcagtgacta tgtatctggt gatggaagca gtctgtgggg tgatatttac  10260
accatcactt atcaaagggc agaaaaccag ccagataagg cgtctactgg aggatcaagt  10320
tcaaatactt caaaatctgc caaatctggg tctgccttaa attcaagctc agaagctaaa  10380
ttgcatcaga catctgttct agacagtata ttgcagggag aattgccatg tgatctagag  10440
aaatctaatc ccacctacaa tattttggca ctcctgcgtg tgctggaggg tttcaaccaa  10500
cttgcgcctc gtttgagggt cctaatggtt tctgatagct ttgccaaggg aaaaatcttg  10560
gatttagatg agctatgtgt tacaactggt gctagggtgc ttctagagga atttgtaagt  10620
ggtaagctta ctccaaaatt ggctaggcaa atacaagatg cccttgcact atgcagtggt  10680
aatcttccct tatggtgtta ccagttgact aaagcgtgcc ctttcttgtt tccttttgag  10740
acccgacgac agtactttta ttctaccgca tttgggttat ctcgtgcact gtatcgactt  10800
caacagcagc aaggtgctga tggccatggt tcaacaactg agagggaggt gagagttggg  10860
agattgcagc gccaaaaggt tcgtgtctct cgaaatcgtg tcctggattc tgctgcaaaa  10920
gttatggaga tgtattctag ccaaaaagct gtacttgaag tagaatattt tggtgaagtt  10980
ggcactggtc tgggtcccac ccttgagttt tatacaattc taagtcatga tttgcaaaaa  11040
gttggactgc aaatgtggag atcttattct tcagacaaac atcaaatgga aatagatgga  11100
gatgaaaaga aaaagaaaag tgaaggctct gggcctaatt tggctggaga tggagaactt  11160
gttcaagctc ctctggggtt gtttcctcgg ccatggccta caaattctga tgcttcagag  11220
agtagccagt tttcaaaagt cattgagtat ttccggctac taggtcgtgt tatggctaaa  11280
gctcttcaag acggacgact actggacctg ccattgtcag tggcatttta taagcttgtt  11340
ctctgccaag tatgttgtgc aatattgatg ttttaaccat tttcattttt tattgttaat  11400
ctgatggtca atttattcta gtcaatgaac ctaaccttca ctttgtggca ggatcttgat  11460
ttgcatgaca ttctgttcat tgatgctgag cttgggaaga ctttacaaga gttcaatgcc  11520
cttgtttgtc ggaaacatta tatagaatct attggtggta gctatacaga tacaattgtt  11580
aacttgtatt ttcatggtgc accaatcgaa gatctttgct tagattttac tctccctggt  11640
tatcctgaat acaccttgaa gccaggagat gaaattgtat ggagttaaac cctgagctag  11700
```

```
tctatagatc ttggttcttc tgttatgaaa atttccttta acttactctc aaattctcag  11760
gttgatatca acaatttgga ggagtatata tccttggtga tcgatgcaac tgtcaagact  11820
ggaatcatgc ggcaaataga agcatttaga gcagggttta accaggtttt atgctgttct  11880
taataattag taatttaact ttaaatgtac acattgttgg tgtggagcat gttatttttc  11940
taaaacaagg tgtttccctc tcccctttct agtggaaagt atcttttatt gacattatcc  12000
tccttgtcta tatatgctcc catacttatc tcccactgca tccctgagaa tttgtttttt  12060
aaccgtgctt aatggtgttg ttagatccac gtagctgaca tctccttgtg ggataagatt  12120
attgtagttg tagattggaa ttagtttacc tgatgcatga cattaatttg ttaacatgcc  12180
attgaaattc ttaagtgaca ttctgtctca ctaaaagtta tttggtgttt taccgagatc  12240
ttaaatatct ttcctttatc tctcatgctt gaatattcca cttgggatct tataaaatat  12300
atgatcctgt tcttttactt acattggctc ccaatcacca actatacttt ccctgtacaa  12360
aatggaaatt gcaagattca gttattggat gttaaacttt ttacattctg aatatattgt  12420
ttgtgaaatg ggtggggtag ttatggctct gctagactct cttgtggagg atgagaagag  12480
gatattgatg gggaaattag ttacttttgg ctcattttat ttagttcaaa actaaacatc  12540
acttgtatgc ttgtgctgtt taatgcaggt ttttgatatc tcatctttac aaatttttac  12600
tcctcaagaa ctagataatt tgctttgcgg ccgcagggag ttgtgggagg tgatttttgc  12660
ccaattatat tattgctttt aatattagtt aaaatattag atttagaaca aggcattgaa  12720
attaaaagtt ttttgttttt aatcttactg caggctgaga cacttgctga tcatataaaa  12780
ttcgaccatg ggtacaatgc aaagagccct gccattgtta atgtatgttt ttttcctcct  12840
aattataagt aatattgtgt attatagaaa attagagcta gttataattt atgatgcttg  12900
tcctgttgga tgctatttta gttacttgaa attatgggag agttcacacc agagcagcaa  12960
cgtgccttct gtcaatttgt tactggtgca cctaggctgc cacctggagg gctggcagtt  13020
ctaaatccaa aactaacgat tgtgaggaag gtattcagaa atgaattttt gataacgtga  13080
tatttaggct tattcatcta tatttttttt catattaatt tcatggttat atatgcatgt  13140
caatatttgt tattaccgtt gtattcatgc cttatttttt ggccttggtg cagctttcgt  13200
caactgcagt taataattca tctaatggga atggaccttc agaatcagca gatgatgact  13260
tgcctagtgt gatgacatgt gctaattacc tgaaacttcc tccttactct accaaggtac  13320
tgtgatatgg catatgagaa atgattttta cgtcacaatg tcttccaacc catccttaca  13380
ccttgtttgg ggaaaatgtg ttttttttcta agtttctatt gtttttattt tccagaaggg  13440
aaaatggtgc aatgaaaatg gtctccaaat aactgtggca tcataaaatt cttgattata  13500
ttatctctca tgtccatgtt tggctgggat taattctcgg gaaaaaattg cttattttta  13560
taataaaagc tcattttgaa acttggcaaa actaaggaat tatttctcaa aaatacatac  13620
gtatgttcat tactctgata ttgcatcttt tggtattaat ctatgatgtt caattttcaa  13680
caggaaatta tgtacaagaa gttgctctat gcaatcagtg agggccaggg atcctttgat  13740
ttatcatgag tttctgaaac taaccaacct taccctgcat gttaatagat ggatcagggt  13800
ttattgactt tattctcgag ggtcagttgt tttttttggt tggatgtgct ttgctcctcg  13860
cttctcgaat aatagtgtct cattttccgt gctcaatgca aattgcaagg ttgtggaatt  13920
attcaggtga gttgaccttt tctgccagta aggttgtatt gatgggatta atcatatctt  13980
tctgctgcag cacgtgaata atttgttact tttttccctc aaactggctg ggagcttctt  14040
```

-continued

```
ctcatgttgt tctcttttat ttctgacata cttataagga tttctcccat aaattgcagt  14100
tgaatcgggt cgccacattt tcaaagtgta ggggaattta cggagctctt atttgatttt  14160
acctgttaga acttgtaaat agaatagcaa tgatgaaatt ttgattttct tttttctttt  14220
taaaaaagtt cattattctg tttgtaattc caattattgg caattagcat gtacgaagaa  14280
aaatggtaaa gggaaaggaa ataatttaaa atattatgct ttataatctc attctattac  14340
ttagtcacta gtcatttgtt attgtaaaat tttgtcaata tcgtcacatg gggaaatatc  14400
gctaatgtta aagcgaatga catgaagcat tatattattg attttcctac gtttgcagat  14460
ttatctttat gcattaaact aaagtatgtt gttagaaaca tgacttagat ccgtttgttt  14520
caatcttatt ttggaggaaa aatgttttaa ttagtttttt aaaatgagat gttaaggcct  14580
tgtttggggt ggtttttagt tttgaatttt taaaaataac aattagtttt agtttgaaaa  14640
aattagtttt taaaatatga ttagtttcaa ataatttttt tattttaaag cgtaatatta  14700
tactaaaatt agtttaaaag tgattttgtg tggtgatgat tatagtgctt acgagtttaa  14760
tttatttttt ctttaaagat aaaatatttt tattttttaa ttttagtaaa gttggatttg  14820
tatttataaa agatgatccc gtgattataa aaggaaggag ggaggaaaaa gtgattggga  14880
gtttgaattc ttccaatgac attcaaaatg tgtaatgtat gatatccttg ctaaatgatt  14940
aaaaagtgat tgttaggact agatatttta aattgtgaag ctagttttaa aagtagaaag  15000
catatcaaat aaaaagttta aaaagctgtt tttttttttt tgcaatttag tttgataatt  15060
tattcttatt ttgaaaattg aattgaacat atgctttttt taatatcaat tcaacattat  15120
atatgttgat ttttctttta tatataaatt actttatttt aatctaactc acgactcagt  15180
tttgacaatg ttaatatgtg attctatatg cgttagacat ttttagttat ggaaaattat  15240
tagtatataa tattgatttc ttgtttttaa atataaatat taattattaa tttgtcagtg  15300
aaaatgattt aaatatataa actctttttt tcctccttct taatcattaa tcattaagtt  15360
aatcttataa tttcttaata tttaacattc ggtaacatat aaactaactg attgtgattg  15420
gtttgttata ttttataaaa agagtttata atgtagttat aatcagtgtt ttctttaact  15480
agtttatatg aactaattga tttttttttt attcttctat gactgggatt gtgatttaat  15540
tagttattag attttatact ctgcaaaatt atttcattag ttatcaaatt aaattatttt  15600
aaaagttata attttttttt taaaagttaa taactattga actgatcaat caaataaaag  15660
aagttaaaaa atgttgaact gatcaatcaa atagtaaaat atttttttga tatatatttt  15720
tgttagaaag tattcttctt gactaagtat ggttatcaaa ctcttgagtt aacttgttaa  15780
ttcttacgag ttttcgagta tgtgagttga ttcgtgtgta aactattttt ttagtagatt  15840
attggtagat tagataaact ctaaataaac tcttgcgttt atcatggagt caacgagtca  15900
gcaagttaaa aaaattaaac caaaatataa gtcattttac ctccatttag tgtgttgctc  15960
ctgaattaaa aaattatcac ctctaataac atcaaaccct tgttctcaaa taacatcaaa  16020
ctcttgataa gaatgctcta ccactattat aacatccaca agttattatt tagtagtgat  16080
gcattactag acttggttag ctaagtattg tgaaattcat gatttactac tttactttat  16140
tatatttttg aaatgtttaa ttgacatgtt atttatagat attttgttat tatttttata  16200
tgaagtggac tcttacgagt ctatgattaa gtatacgagt caaatctatg aaactcttac  16260
aaatttacgt aaactttcga gtttgataac ctttaactca attattatct atagcattag  16320
ctcttttcaa atatttaaat ttgttgtata ttcatgattc aagatctttg attaagatag  16380
agtattctta ctcacaagtt gattccccta tgtaatcaaa gcttag                16426
```

<210> SEQ ID NO 8
<211> LENGTH: 16429
<212> TYPE: DNA
<213> ORGANISM: Glycine max

<400> SEQUENCE: 8
atggaaaact cgaaatcaag ggtttcaaag taataggagg tacaagaaaa gcttgcaaat 60
ccatcacccg agagaatata aaactcttag aaccaagaaa catctaactt cccctaacct 120
tacaccgtat tttactttca caataaaaaa taattacctg gatagttgct ttcaacccaa 180
atttcttaag agcaacaatg gcattaggat ttccagccca ttttacagaa gactccataa 240
ttaactcttt ttcgtcagtc tcataaactt tcattcttat tgagaataaa ttatgcattc 300
aataagaaaa atggaaaaat tcacatagaa tcacaaataa gttagtaaaa aatagaataa 360
ttgcatttat aaaacaaaca cataagtatt ttgtaggggt cataaagttg acttagtggt 420
gatataaaaa aagagaatag agagattgta tacattaatt cttccactaa caaaaaatga 480
acaactaata tttatcaata aaaaaagtat acgtgatatt ttttttttt taaagagata 540 aaccatttta acaaaaaaaa tattttataa gggttccttt taatgagtga agcccaaaac 600
aagatcttat ggtaaaatgc atcatttgat agatcaaagt ttctttaaac tctaaataaa 660
attcatacca gtatgggttt caaaccttaa taattatcaa ataccagtaa tgtaattgat 720
tttagagatg cagtaaaaac aaatgaaaat tgaactgtct taatatttga tgtattattt 780
tcgaaatgaa tatttgatat attattaaag atgtatttta tgagtattta agatgtttta 840
ttgttctttc aaattaaaac catcttgtta attgttagtt tattacattt ctcccaaaaa 900
aacatgattt atcattagaa ccaaaaataa tttctaaatt gtgatttgta tcctttacag 960
atgataaaaa cgagtgaaat ttaggtatta tcatagttta cacattggta atatttatat 1020
tatttgtgca aaccagtaaa aagtttttat ctaataataa accacatcta aataaactaa 1080
ccttgaaaag ttggcggcaa agaccctagt gagctcttca aactcaacag aatcaatttt 1140
atatttcggt atttgctcat caattattgg ttttgcaata ttctttgcag tcttgcatat 1200
tgcctaaatg aaaaaaccca atcaaacaat cacacaaaaa agaagaaaaa atacatgcta 1260
cttgataatt gtccgaaaat ataataaaac ataccttttc aaggtatggc cacatatatt 1320
caataagctt gttaagccaa tcaaccttca taaaaacacc aataaataat agtgtggttg 1380
ttaaaatact tgtggagtgt gtttggatga gaaattttaa attctaaaaa ttttaaatac 1440
ttcaattcaa attcttttat tttcaaaatt ttgtgtttgg ataaaaaaaa attaaaattg 1500
tgagggtgaa agaaaatgaa tgcaaagaga aaaaaaaata tggttagtgt gcttctaaag 1560
agaagaatat tgatgtgcca tggggagtcg cacggaaacc gggatacaat gacgtacacc 1620
atcatatccg accacaacat taagtcaacg gcgcaaggca tggcccagac ctttcgcacc 1680
gacgagcacc tctatcgcgt gatagacaac gataattgtt cccctgattg gcaccgttct 1740
atgtgtctcc ctatatccgc acccgatcga tgctccgcgt gagctcagac agtgtttcat 1800
gaagtagaga attatcgacg taaggaaaga ttcacgagtt cgagaacgag atttcaaact 1860
caggtgaacg agaggatgaa gatgataaag gaaatataca aacattttgg aatattctct 1920
tatcaagaag agaattttaa tttctcactt ttgaaaaaaa attaaaattt cacattttta 1980
gttgtttaaa attctgtttt aaaattttaa attctccata aaaaaaacat ccaaataatg 2040
aattttaaat taaaaaaatt taaattttct gataaattac ttttcttagt taaaattcgt 2100

-continued

```
agtgcatttt acatattaac aaagagtaac ccattgcttt cccgatcaaa gtctggattt   2160
ttttatccaa aggggtatct caggaatcat tccctgtaaa gttttcgagt cttcctccgc   2220
caatggctgg atatcaggat cctatccaag ccaacaatgt attggtgcaa tacttaaaaa   2280
atgcattaaa aatgtcaaaa tttcaaagat tcacaatcaa ttttcttttt tgattgcttt   2340
ttgacgtata taatagtgtg gcgttaccta ttttaaactt tttttcttat ggttagtgaa   2400
gttactaaag acaaaaatat ttagattcca agataatgtg taagataagg attattataa   2460
tttatgatca taatttacaa aaacttgtta gagaacattg attagcttgt aaaagaaaat   2520
aaaacaaaca aaattagacc cagacattat ctaaaggaaa gagaaaggtt tacaacgggg   2580
tggaatacaa aacaagataa tttgttaaga accatgtttt gtttgtacca tgtaccttaa   2640
cttcagtgga ttgaacgtaa ataaagagaa aataaccaat aacgagaccc atagaaatcc   2700
caaatccaaa tccaaaatga ccaaatatag tgctaaagaa atccatctca gttcttaatt   2760
ttgttttcag accaaacttg ctctgatgac aatcacaatc tctttctctc tccgtgtgct   2820
aaaagtaaaa ttattatgca aatccgttac ttccgatgtc tttgagttct cctcggatca   2880
ccattcctat attcaaacca aaacatgtaa tgcaaatcat tttgacccaa aaaaagacta   2940
tttatacaaa aaaaaaagtt atggttatta ctaaggattt aacacaaatg attacgttat   3000
tcttattaat taaagttact accactattt ttttggagtg acactaccac ataatttgtt   3060
tattcatgtt attatatatt tgaggaaaag tcataaataa attatataat gaataaaaat   3120
aaaataaaat atttaaaaat taaacatgtt actacattat ctttaacata ttttctctat   3180
atttttatgt tacaaaaaat tgtataatat ttaagaaaac aaaaacacta ttaaacacat   3240
agatcaattg atttaaaact attaaagttt aagtaatatt ttcgaattcg aattctatat   3300
atgttacggc atgaaatact tgtaggaaga attagatgct tgtggtctct aaaaaaaact   3360
tccctccctc aaaattttcc ctatggaatg tgaatttttt tgttgggtga tacaaaaatg   3420
attatgtttt ttctttacct ctttatttaa taaatagtaa aattttgatg ttctttcctt   3480
ttatttatca ttttttcctt tttattaaac caaacaataa ctgagaggag gaatggggaa   3540
gtagcaattt ggattattct tttcttgttt tttttttaaa ataaaaaaca taacataaaa   3600
taaaaaatta attttgatgc attgttagtt gaaagatgat tattattata tattaaaagt   3660
taaataataa taataaataa tttatgttaa tttttaatct accaaattat tttaatttaa   3720
atattatttt ctgttttact ttatttatgt tgaatctacc aatatttatt tctcccccac   3780
cacccccatt ttttacatca acatagatta aaacggatag aatttgtagt ggaagattaa   3840
ataaaattga ttaataaaat atatgtatgt ttctggggga caagtattta aatttaaatt   3900
tgataagata tgggtgatat gaaatgtagt aattttcaat gagccgaaaa cgacgcggag   3960
gcagcaagcg agttctcact tagagtgttg ttgttgtgca aacaaagtta agttacgtat   4020
aaaaggggta tttgatatct ctgtcttttt attctctccc tctcgctcct caccttaggg   4080
ttttcatgca acaatttcct cctcctcctc ctctctctct ctctctctac actagattgg   4140
ggattttcct tggatttagg gtttccgccg attttgattt taatttaata catttgtctg   4200
agatgcaacg gattaatcca atcgatcgat cggggatagg tgagacaaat tgaagggtga   4260
gtgtgggttt tgtatggaaa ctcggagtcg gaagcgggcg gaggcttcct cagctgcccc   4320
ttcatcctcg tccaccaccc cttctcgttc agccaagcgc tctcgtcttt cttcttcttc   4380
ttcttccatc ctacctgtta atacacgttc tcgttccgcc aggaataaca acaacaacaa   4440
caactccggt tccatttctt tcatggaccc caccaatgaa tcctccgggt cccgacgtga   4500
```

```
tcgccgtggc aagaatttcg atagggaaaa ttcggacaaa gggaaggaga aggaacagga   4560
tgttaggatt agggatgcgg agcgggagcg agagcgagcc ttggcgttaa acatggagag   4620
tgaagatgtt ggggatgacg atgataatga tagtgacggc ggtgtgggaa ttctgcacca   4680
gaatttgacg tctgccagta gtgcccttca agggcttctt cggaaacttg gtgctggttt   4740
ggatgatttg cttcctgcta ctgctatggg cggttctgcg tcatctcctc atcagagtgg   4800
cagactcaag aagattttgt ctggcttgcg tgccgatggg gaagaaggtc gtcagttgag   4860
gcattgacgc agctttgtga catgctctcc attggcactg aagattccct cagcacattt   4920
tcggttgact catttgttcc tgtgctagtg ggcttgctta atcacgagag caatcccgat   4980
gtcatgcttc ttgcggccag ggcgctaacc catttatgtg atgtgcttcc ttcatcctgt   5040
gctgctgttg tgcattatgg tgctgtctct atcttctgtg cgaggctgct caccatagag   5100
tatatggact tggctgagca ggttattttc tcagtcaatc tcttttgtgc ctttacttat   5160
tatgtatctg tgtcttacga tgtatgagct tcctaagtcc ttaaccctta gttgttgaaa   5220
atgggcttcc gtcttaaacg aggttcttat catttgacac accttacggt tttctacttt   5280
gaattctgat agttgtgatt gttgatgtga acagtctctt caagcactaa agaagatttc   5340
tcaggagcac ccaactgcct gtcttagagc tggagctctg atggctgttc tttcttactt   5400
ggacttcttc tcaacaggag ttcaggtaac taatcaatga aatcctaaca tcaaagggtg   5460
acaattcatt ttgcgtttac caccccttgat tagcaagcct atattgacat aatcatgtgt   5520
ttcagcgggt ggcattgtct actgctgcaa atatgtgcaa gaagcttcct cctgatgcag   5580
ctgactttgt gatggaagct gttccacttt tgacaaacct ccttcagtac cacgactcca   5640
aggtaaggca tgtttgcttg tcatatttgt cataaaatga aaactgcact ttccttgtca   5700
ttccttcctt ttaaggaaat tttgtttgtg taaatattga tccctacaac tgatgttgtc   5760
aattatctat ttgcgttttc ataataaaaa acttcgtacc ccattgtcca gaggctcttc   5820
actatgcgaa ggtatggggg agggatgttg tacgcagcct taccccttgca ttttcataat   5880
attcaatgtt aatttttgta ggtcctggaa catgcctctg tttgtttgac acgaatagct   5940
gaagcatttg catcatctcc agacaaatta gatgaattgt gcaatcatgg actggtaaca   6000
caagctgcct ctctcatttc taccagcagt tctggaggtg ggcaggcttc tctcagcact   6060
ccaacatata ctgtaagtgc aatctttgcc actaaatctg atacttttat cctttggtgg   6120
gttgttcctt tgacttcatt ggtgcatgca gggtttgatc cgccttcttt ccacatgtgc   6180
aagtgggtct cctcttggag ctaaaacgtt gcttctcctt ggaactagtg gcattcttaa   6240
agatatacta tccggttccg gtgtttcttc taacacctct gtttcgcctg cattgagtag   6300
gccagcggat caggtatgtg tacttttgag ttctttatgt ctgttatatg tagttggtat   6360
ctctatagtt catttgatag attgtgacat cgatctcatt atttaaatcc ttgaaaactt   6420
ttcagttccc tttttgtgaa agatgagttt ttcctaattc tctttcctaa tatttagata   6480
tttgagattg tgaacctggc aaatgaactt ctgcctccat tgcctcaagg aaccatttcc   6540
cttcctgtca gctccaactt gtttgtgaaa gggtctgttg tgaaaaaatc ctcttctggc   6600
aattctggga tacaagaaga cacaaatgga aatgttcatg agatattggc tcgtgagaaa   6660
ttattaaatg atcagcctga gttacttcag caatttggga tggatctcct cccagtttta   6720
atgcaggttc aatgcttaaa tttacttaat tgttaaaatg ctcaaattat attttgtgat   6780
ttgtttatta atttttaact tcttaaataa ataactggct ctatttttta tatcctcgac   6840
```

```
ttcttcattc cttcactccc gtcacttatt actagttttg tcttgctttt gaaacagata   6900
tatggtgcta gcgtcaatgg tccagttcgg cacaaatgtc tttctgtcat tggaaaattg   6960
atgtatttca gcacagctga gatgatccag tctttactga gtgtaacaaa tatatcaagg   7020
tatctagaac ttcaattggg ttgctgttgc tctatgttct ctgtagaata cttatgcatt   7080
gtcactttga tgatatagtt tcttagctgg tgtgttagca tggaaagatc cacatgtttt   7140
ggttcctgcc ttgcaaattt cggaaattct tatggaaaag cttcctggaa ccttctctaa   7200
gatgtttgtc agagaaggtg tggttcatgc agttgaccaa cttattttgg ctggaaattc   7260
aaccaatata tccacacaaa catcatctgc tgagaaggat aatgattctg tatctggaac   7320
ttcatctcgc tctagacgct atcgcctgcg cagtggtaat tcaaatcccg atgcgaaccc   7380
ttcagatgat ttaaagagtc cagttccagt aaatgttggt ttgccaccaa gttctgtaga   7440
aactccaaca actaattcta gtatccgtgc atctgttagc tcagttgcta gagcttttaa   7500
agacaagtac tttccttctg atcctgggtc tgttgaagtg ggtgttagtg atgatctttt   7560
gcatctgaaa aatctatgca cgaagttgat cactggtgtt gatgaccaaa gaagcaaggc   7620
aaagggaaaa gttaaagctt ctggatttgg tctggatgat aattctagta acacagaaga   7680
gtatttgatt ggggtgatat ctgacatgct aaaggaactt ggcaaaggag atagtgtatc   7740
tacttttgaa tttatcggta gtggtgttgt tgaagccttg ctaaattatt tttcttgtgg   7800
gtatttctct aaagatcgaa tatcagaaac caatctcccc aagcttcgcc aacaggcact   7860
ttcaaggttc aagtcatttg tagctgttgc actacctttg agcattgaca atggggctgt   7920
tgctcctatg actgtcttag ttcagaagct tcaaaatgcg ttggcctcct tggagcgttt   7980
ccctgttatg ctgagtaatt catctcggtc atctagtgga agtgcacgtc tctcctctgg   8040
gctaagtgca ttatctcagc ccataaaatt acgtctctgc cgagcccagg gtgaaaagtc   8100
acttagggat tattcatcca atgtggtact gattgatcca ttagcaagtc tagcagccat   8160
cgaggaattt ctatgggctc gtgtccagcg tggtgaatct ggtcagaagt ctactgtagg   8220
cactgaaaat tctgaatctg gaacaactcc tgctggggca ggtgtttcat ctccttcctc   8280
ttatactccc tccactgccc atcgtcattc tactagaacc agatcatctg ttaatatagg   8340
agatacacct agaaaagaaa catctcaaga caaaggaacg agctcatcaa agagcaaggg   8400
taaagctgta ttaaaacctg cgcaggagga agcgcaagga ccccaaacaa ggaatacagt   8460
gcgcagaaga gcagctcttg ataaagtcgc tcaaatgaaa cctgcaaatg gcgactcaac   8520
ttctgaggta tgctgctaaa ttctgggaac gagtcataat aattaaataa tattaatcta   8580
aattggttta taacattgaa taatttaatc tttgttggat tttgtttata cttatgctta   8640
ttctccttcc ctctttttgt tagataaaaa accattggtg agatttcttc atctaatagt   8700
tagttgatgt tggcttttat tttactgctt tggattaaaa tgatgctttc agttgacgtg   8760
tctcctgtag catcttaaac ttgagtggtg gcttttatta tttaagtcat ttttattgtt   8820
tgacattatt ttcccctgct tttatgggat aggatgaaga attggatata tctcctgttg   8880
aaattgctga ggctttggtg attgaagatg atgatatttc tgatgatgag gatgaagacc   8940
atgaagatgt atgtttcttc ttctgctaag atttcatctt attgttgtga ttacttttat   9000
tcatatctca ttttgtgatc taaattgtaa gatctcacaa tcttgctgcc actttccttt   9060
ctgaatcact tgtaaaatct taaatgagtt cgttgtgaga tttcaagatt gctgaactgg   9120
tgagattgtg taatcatgtg cagtccaaaa atctgtcaat ttcgagttat gtttcaagta   9180
ttttcttttg tgacttctgg ttgtgttatg tatgtgacta attatgactt gttttggatg   9240
```

```
ttatggttat gaaatttcaa ggctaagttt gctataatgt tatctatatt tttctttcat   9300
attttctatg catacataaa cctatataat tttttggtag gattttatga tctacatttt   9360
acaattttgc atccccccttc caatcttagg tagaatctca atcttgacaa cattggttgt   9420
taccaatatt gaaaactatc atttaggcgc atccattctt gcaattgagt tttaccaaat   9480
agaaatgtta ttgttgtttc caagaatgga tactaccatt aattgttgtt tagattggat   9540
attatgattt ggtttagctg ttctgttcta gctattgaat tttatcaaat agaaatggta   9600
ctattgtttc ttatattttt aataatcatt aattgatgat tccaagattg gatgctatca   9660
tttgattcag ttgcatccat gctagtaatt gaatttatga tattattcca ctaaccatca   9720
tctaatgcat catcagcttg ttttatttat tttattttat tttattttat ttttgagcag   9780
gtgctgaggg atgattctct tcctgtctgc ttgcctgaca aagtgcatga tgtgaaattg   9840
ggtgactcag ctgaggagag tactgttgct ccagcaacaa gtgatagcca gactaatgca   9900
gcctcaggtt caagcagcaa agctggtaca gccaggggtt ctgactccgc tgattttagg   9960
agtgggtttt catctagctc aaggggtgca atgtcatttg ctgctgctgc tatggctgga  10020
cttggatatg ctaatagcag aggtttcagg ggcggcagag ataggcatgg gtgcctgttg  10080
tttggtagtt ctaatgatcc tccgaagttg atttttacta ctggtgggaa gcagcttaat  10140
aggaatctga gtatatatca ggcaattcaa agacagcttg tgctagatga agatgatgat  10200
gagagatttg ctggcagtga ctatgtatct ggtgatggaa gcagtctgtg ggtgatatt   10260
tacaccatca cttatcaaag ggcagaaaac cagccagata aggcgtctac tggaggatca  10320
agttcaaata cttcaaaatc tgccaaatct gggtctgcct taaattcaag ctcagaagct  10380
aaattgcatc agacatctgt tctagacagt atattgcagg gagaattgcc atgtgatcta  10440
gagaaatcta atcccaccta caatattttg gcactcctgc gtgtgctgga gggtttcaac  10500
caacttgcgc ctcgtttgag ggtcctaatg gtttctgata gctttgccaa gggaaaaatc  10560
ttggatttag atgagctatg tgttacaact ggtgctaggg tgcttctaga ggaatttgta  10620
agtggtaagc ttactccaaa attggctagg caaatacaag atgcccttgc actatgcagt  10680
ggtaatcttc ccttatggtg ttaccagttg actaaagcgt gcccttttctt gtttcctttt  10740
gagacccgac gacagtactt ttattctacc gcatttgggt tatctcgtgc actgtatcga  10800
cttcaacagc agcaaggtgc tgatggccat ggttcaacaa ctgagaggga ggtgagagtt  10860
gggagattgc agcgccaaaa ggttcgtgtc tctcgaaatc gtgtcctgga ttctgctgca  10920
aaagttatgg agatgtattc tagccaaaaa gctgtacttg aagtagaata ttttggtgaa  10980
gttggcactg gtctgggtcc cacccttgag ttttatacaa ttctaagtca tgatttgcaa  11040
aaagttggac tgcaaatgtg gagatcttat tcttcagaca aacatcaaat ggaaatagat  11100
ggagatgaaa agaaaaagaa aagtgaaggc tctgggccta atttggctgg agatggagaa  11160
cttgttcaag ctcctctggg gttgtttcct cggccatggc ctacaaattc tgatgcttca  11220
gagagtagcc agttttcaaa agtcattgag tatttccggc tactaggtcg tgttatggct  11280
aaagctcttc aagacggacg actactggac ctgccattgt cagtggcatt ttataagctt  11340
gttctctgcc aagtatgttg tgcaatattg atgttttaac cattttcatt ttttattgtt  11400
aatctgatgg tcaatttatt ctagtcaatg aacctaacct tcactttgtg gcaggatctt  11460
gatttgcatg acattctgtt cattgatgct gagcttggga agactttaca agagttcaat  11520
gcccttgttt gtcggaaaca ttatatagaa tctattggtg gtagctatac agatacaatt  11580
```

```
gttaacttgt attttcatgg tgcaccaatc gaagatcttt gcttagattt tactctccct  11640
ggttatcctg aatacacctt gaagccagga gatgaaattg tatggagtta aaccctgagc  11700
tagtctatag atcttggttc ttctgttatg aaaatttcct ttaacttact ctcaaattct  11760
caggttgata tcaacaattt ggaggagtat atatccttgg tgatcgatgc aactgtcaag  11820
actggaatca tgcggcaaat agaagcattt agagcagggt ttaaccaggt tttatgctgt  11880
tcttaataat tagtaattta actttaaatg tacacattgt tggtgtggag catgttattt  11940
ttctaaaaca aggtgtttcc ctctcccctt tctagtggaa agtatctttt attgacatta  12000
tcctccttgt ctatatatgc tcccatactt atctcccact gcatccctga gaatttgttt  12060
tttaaccgtg cttaatggtg ttgttagatc cacgtagctg acatctcctt gtgggataag  12120
attattgtag ttgtagattg gaattagttt acctgatgca tgacattaat ttgttaacat  12180
gccattgaaa ttcttaagtg acattctgtc tcactaaaag ttatttggtg ttttaccgag  12240
atcttaaata tctttccttt atctctcatg cttgaatatt ccacttggga tcttataaaa  12300
tatatgatcc tgttctttta cttacattgg ctcccaatca ccaactatac tttccctgta  12360
caaaatggaa attgcaagat tcagttattg gatgttaaac tttttacatt ctgaatatat  12420
tgtttgtgaa atgggtgggg tagttatggc tctgctagac tctcttgtgg aggatgagaa  12480
gaggatattg atggggaaat tagttacttt tggctcattt tatttagttc aaaactaaac  12540
atcacttgta tgcttgtgct gtttaatgca ggtttttgat atctcatctt tacaaatttt  12600
tactcctcaa gaactagata atttgctttg cggccgcagg gagttgtggg aggtgatttt  12660
tgcccaatta tattattgct tttaatatta gttaaaatat tagatttaga acaaggcatt  12720
gaaattaaaa gtttttgtt tttaatctta ctgcaggctg agacacttgc tgatcatata  12780
aaattcgacc atgggtacaa tgcaaagagc cctgccattg ttaatgtatg ttttttttcct  12840
cctaattata agtaatattg tgtattatag aaaattagag ctagttataa tttatgatgc  12900
ttgtcctgtt ggatgctatt ttagttactt gaaattatgg gagagttcac accagagcag  12960
caacgtgcct tctgtcaatt tgttactggt gcacctaggc tgccacctgg agggctggca  13020
gttctaaatc caaaactaac gattgtgagg aaggtattca gaaatgaatt tttgataacg  13080
tgatatttag gcttattcat ctatattttt tttcatatta atttcatggt tatatatgca  13140
tgtcaatatt tgttattacc gttgtattca tgccttattt tttggccttg gtgcagcttt  13200
cgtcaactgc agttaataat tcatctaatg ggaatggacc ttcagaatca gcagatgatg  13260
acttgcctag tgtgatgaca tgtgctaatt acctgaaact tcctccttac tctaccaagg  13320
tactgtgata tggcatatga gaaatgattt ttacgtcaca atgtcttcca acccatcctt  13380
acaccttgtt tggggaaaat gtgttttttt ctaagtttct attgttttta ttttccagaa  13440
gggaaaatgg tgcaatgaaa atggtctcca aataactgtg gcatcataaa attcttgatt  13500
atattatctc tcatgtccat gtttggctgg gattaattct cgggaaaaaa ttgcttattt  13560
ttataataaa agctcatttt gaaacttggc aaaactaagg aattatttct caaaaataca  13620
tacgtatgtt cattactctg atattgcatc ttttggtatt aatctatgat gttcaatttt  13680
caacaggaaa ttatgtacaa gaagttgctc tatgcaatca gtgagggcca gggatccttt  13740
gatttatcat gagtttctga aactaaccaa ccttaccctg catgttaata gatggatcag  13800
ggtttattga ctttattctc gagggtcagt tgtttttttt ggttggatgt gctttgctcc  13860
tcgcttctcg aataatagtg tctcattttc cgtgctcaat gcaaattgca aggttgtgga  13920
attattcagg tgagttgacc ttttctgcca gtaaggttgt attgatggga ttaatcatat  13980
```

```
ctttctgctg cagcacgtga ataatttgtt actttttttcc ctcaaactgg ctgggagctt  14040
cttctcatgt tgttctcttt tatttctgac atacttataa ggatttctcc cataaattgc  14100
agttgaatcg ggtcgccaca ttttcaaagt gtaggggaat ttacggagct cttatttgat  14160
tttacctgtt agaacttgta aatagaatag caatgatgaa attttgattt tcttttttct  14220
ttttaaaaaa gttcattatt ctgtttgtaa ttccaattat tggcaattag catgtacgaa  14280
gaaaaatggt aaagggaaag gaaataattt aaaatattat gctttataat ctcattctat  14340
tacttagtca ctagtcattt gttattgtaa aattttgtca atatcgtcac atggggaaat  14400
atcgctaatg ttaaagcgaa tgacatgaag cattatatta ttgattttcc tacgtttgca  14460
gatttatctt tatgcattaa actaaagtat gttgttagaa acatgactta gatccgtttg  14520
tttcaatctt attttggagg aaaaatgttt taattagttt tttaaaatga gatgttaagg  14580
ccttgtttgg ggtggttttt agttttgaat ttttaaaaat aacaattagt tttagtttga  14640
aaaaattagt ttttaaaata tgattagttt caaataattt ttttatttta aagcgtaata  14700
ttatactaaa attagtttaa aagtgatttt gtgtggtgat gattatagtg cttacgagtt  14760
taatttattt tttctttaaa gataaaatat ttttattttt taattttagt aaagttggat  14820
ttgtatttat aaaagatgat cccgtgatta taaaaggaag gagggaggaa aaagtgattg  14880
ggagtttgaa ttcttccaat gacattcaaa atgtgtaatg tatgatatcc ttgctaaatg  14940
attaaaaagt gattgttagg actagatatt ttaaattgtg aagctagttt taaaagtaga  15000
aagcatatca aataaaaagt ttaaaaagct gttttttttt ttttgcaatt tagtttgata  15060
atttattctt attttgaaaa ttgaattgaa catatgcttt ttttaatatc aattcaacat  15120
tatatatgtt gatttttctt ttatatataa attactttat tttaatctaa ctcacgactc  15180
agttttgaca atgttaatat gtgattctat atgcgttaga catttttagt tatggaaaat  15240
tattagtata taatattgat ttcttgtttt taaatataaa tattaattat taatttgtca  15300
gtgaaaatga tttaaatata taaactcttt ttttcctcct tcttaatcat taatcattaa  15360
gttaatctta taatttctta atatttaaca ttcggtaaca tataaactaa ctgattgtga  15420
ttggtttgtt atattttata aaaagagttt ataatgtagt tataatcagt gttttcttta  15480
actagtttat atgaactaat tgattttttt tttattcttc tatgactggg attgtgattt  15540
aattagttat tagattttat actctgcaaa attatttcat tagttatcaa attaaattat  15600
tttaaaagtt ataatttttt ttttaaaagt taataactat tgaactgatc aatcaaataa  15660
aagaagttaa aaaatgttga actgatcaat caaatagtaa aatatttttt tgatatatat  15720
ttttgttaga aagtattctt cttgactaag tatggttatc aaactcttga gttaacttgt  15780
taattcttac gagttttcga gtatgtgagt tgattcgtgt gtaaactatt tttttagtag  15840
attattggta gattagataa actctaaata aactcttgcg tttatcatgg agtcaacgag  15900
tcagcaagtt aaaaaaatta aaccaaaata taagtcattt tacctccatt tagtgtgttg  15960
ctcctgaatt aaaaaattat cacctctaat aacatcaaac ccttgttctc aaataacatc  16020
aaactcttga taagaatgct ctaccactat tataacatcc acaagttatt atttagtagt  16080
gatgcattac tagacttggt tagctaagta ttgtgaaatt catgatttac tactttactt  16140
tattatattt ttgaaatgtt taattgacat gttatttata gatattttgt tattattttt  16200
atatgaagtg gactcttacg agtctatgat taagtatacg agtcaaatct atgaaactct  16260
tacaaattta cgtaaacttt cgagtttgat aacctttaac tcaattatta tctatagcat  16320
```

```
tagctctttt caaatattta aatttgttgt atattcatga ttcaagatct ttgattaaga  16380

tagagtattc ttactcacaa gttgattccc ctatgtaatc aaagcttag              16429


<210> SEQ ID NO 9
<211> LENGTH: 14158
<212> TYPE: DNA
<213> ORGANISM: Glycine max

<400> SEQUENCE: 9

aagtggtatc tcaggaatca ttctctgtaa agtttccgag tcttcctccg ccaatggttg     60

aatttcagga tcctatccaa gccaacaata atgtattagt gcaatactta aaaattgcat    120

taaaaatgtc aaaatttcaa agatttacca tcaattttat attttttatt gctttttttgc   180

atatataata gtgtgattat acctatttta aatttttttt cttatgggta gtgaagttgc    240

taaagacaaa aaaaattgaa ttccaagatg acatgtaaga aaaggattat ttattataat    300

ttatgatctt aatttacaaa aacttgttag agagcattgc ttagcttgta aaaatgaata    360

aaacaaataa aatcagactc aaacatggat ctaaaggaaa gagaaaggtt tacaattggg    420

tggaatacaa aataagataa tgtgttaaga atcatgtttt gtttgtacta cgcaccttaa    480

catcagtggg ttgaacatat ataaagagaa aatagccaat aacgaaacca atagaaatcc    540

caattccaaa gccaaaaaaa ccaaatatgg tgccaaagaa acccatgtca gttcttaatt    600

ttgtttcaac ttgctctgag gacaatccca atctctttct ctctccttat gctacaagta    660

aaattatcat gcaaatgcgc cacttccgat gtacttgagc tctcctcgga tcaccattcc    720

tatgttcaaa ccaaaacgtg gaatgcgaac cattttgacc ctaaaaaaag actatttata    780

ccaaaaaaaa taaaaacaaa gtatggttat cactaaggat ttaacacaaa tgattatgtt    840

attcttatta attaaagtta ctaccacaac ttttttttcgg aatgatacta tcacataatt   900

tgtttattca tgatattata tatttgagga aaagtcacat gatatttaat tattttatct    960

cttaattatg tactatgcga tttagttaat ctttgacttt cttgtttgat atccaatttt   1020

aaaagtcagt ttacatttca taatgaataa aatcaaaata agatatttaa aaaataaaac   1080

atgttactgt attattttaa catattttta aaataatttt aagttaaaaa atgatttaat   1140

attttaagaa aacaaaaata ctattaaaca tgtaaatcaa ttcacataaa attatttgag   1200

tttaattaat attctttaat tcgagattta tacatatgaa cacatgatta aacatctact   1260

atcataaata ctatcttaat acccgttata tttgtagaaa attatttact tgtttagatg   1320

aacgaaatat ttttttttttc agagacgaat ggaagaatga gttaaaataa acaaattata  1380

taatttttat aaagaaaaaa atatatttaa aaattaaaca tgttactaca tcatttctaa   1440

caattttttt tatattttta tgttaaaaaa gatttaatat ttcagaaaaa aaacactgaa   1500

tcatgtaaaa aaattgacat gaaattgttt aagtttattc atcttttttc cttttcatca   1560

aaccaaataa taagtgagag aaggagtgga gagttagcaa tttggattat ttatattttg   1620

tttttaaat aaaaaatcat atttaatatt tttgtgtcta ttttaattta tttatcttta    1680

atcaaacaat cttcattttc atcatatttt ttacctatta acttttgttt tctccccttt   1740

atttctcaca actaaaacaa acaaggagag attaaattaa attgataaat aaaagataca   1800

gtgttgctgc ttttgttgag gttgagaggg caagtattta atatataaaa aatgggtgat   1860

atgaaatgta ataattttca atgagctgaa aacgacgcgg agggagcaag cgagttgtga   1920

cttctgactc agtgttttag agtgacgagt ggatgtatgt gcaaacaacg tatataaggc   1980

gtatttgata tatctctgtc tttcttgttc ctttttttatt ccctctccct ctcaccttag  2040
```

```
ggttttcatg caacaatttc ctcctctctc tgtacactat attgggaatt ttcctttgat   2100
ttagggtttt cgccgatttt aatttaatac atttaatctg agatgcaagg gattaatcca   2160
atcgatcgat ctaggatagg tgagacaaat tgaagggtga ttctgggttt tgtatggaaa   2220
ctcgtagtcg taagcgggcg gaggcttcct cagctgcccc ttcatcatcc tcgtccacca   2280
ccaccaccac cgcctctcgt tccgccaagt gctctcgtct ttcttcttct tcttcttcca   2340
tcccaaacac aactactgct aatacacgtt ctcgttccgc caggaacaac aacaacaact   2400
ccgtttctcc catggacccc accaatgaat cctccggttc cagacgtgat cgccgcggca   2460
agaatttcga tagggacaat tcggacaaag ggaaggagaa agaacatgat gttaggatta   2520
gggatgcgga gcgggagcga gccttggcgt tgaacttgga ggctgaagat gttggggatg   2580
acgacgatga taatgatagt gagggcggtg tcggaattct gcaccagaat ttgatttctg   2640
ccagtacctt tcgagggctt cttcggaaac ttggtgctgg tttggatgat ttgcttcctg   2700
ctacggctat gggcggttct gtgccctctt ctcaccagac tggcggactc aagcagatat   2760
tgtctggttt gcgtgccgat ggggaagaag gtcgtcaggt tgaggcattg acgcatcttt   2820
gtgacatgct ctccattggc actgaagatt cattaagtac attttcggtt gattcatttg   2880
ttcctgtgct agtgggcttg cttaatcatg agagcaatcc cgatgtcatg cttcttgcgg   2940
ccagggcgct aacccattta tgtgatgtgc ttccttcatc ctgtgctgct gttgtgcatt   3000
atggtgcagt ctctatcttc tgtgcgaggc tgcttaccat agagtatatg gacttggctg   3060
agcaggttat tttctcactc aatctctttt atgcctttag ttattatgta tctggaattc   3120
tttttagaat tttgtcttac tttgaattct gatagatgtg attgttgatg tgagcagtct   3180
cttcaagcac taaagaagat ttctcaggag cacccaactg cctgtcttcg agctggagct   3240
ctgatggctg ttctttctta cttggacttc ttctcgacag gagttcaggt aactcatcaa   3300
tgaaatccta atatcaaagg gtgatgattc attttgcatt tgccaccctt gattggcaag   3360
cctatattga cacaatcatg tttcagcggg tggcattgtc tactgctgca aatatgtgca   3420
agaagcttcc tcctgatgca gctgactttg tgatggaagc tgttccactt ttgacaaacc   3480
tccttcagta ccacgactcc aaggtaaggc caaggccatg tttgcttgtc ataaaaatga   3540
aaactgcact ttccttgtca ttccttccct ttaaggaaat tttgtttatg taaatattga   3600
ttcctacaat gttgtcaatt atctatttga gtcttcataa tattcaatgt taatttttgt   3660
aggtcctgga acatgcctct gtttgtttga cacgaatagc taaagcgttt gcatcatctc   3720
cagacaaatt agatgaattg tgcaatcatg gactggtaac acaagctgcc tctctcattt   3780
ctaccagcgg ttctggaggt gggcaggctt ctctcagcac cccaacatat actgtaagtg   3840
caatctttgc cactaaatct gatattttta tcctttggtg ggttgttcat ttgacttcat   3900
tggtgcttgc agggtttgat ccgccttctt tccacatgtg caagtgggtc tcctcttgga   3960
gctaaaacgt tgcttctcca tggagctagt ggcatactta aagatatact atccggttcc   4020
ggtgtttctt ctaacacctc tgtttcgcct gcattgagta ggccagcgga tcaggtatga   4080
tgtgcttttg agttcttttg gtctattaga tgtagttggt atctctatag ttcatttgat   4140
agactgtgac attgatctca tcatttaaat ctcagaaaac ttttcagttc tctttttgtg   4200
aaagatgagt ttatcctaat tctcttttct aatatttaga tatttgagat tgtgaacctg   4260
gcaaatgaac ttctgcctcc attgcctcaa ggaaccattt ctcttcctgt cagctccaac   4320
ttgtttgtga aagagtctgt tgtgaaaaaa tctcctcctt ctgggaatcc cgggatacaa   4380
```

-continued

```
gaagacacaa atggaaatgt tcatgaaata tcagctcgtg caaaattatt aaatgataag   4440
cctgagttac ttaagcaatt tgggatggat ctcctcccag ttttaatgca ggttcaatgt   4500
ttaaatttac tcatcgttaa aatgctcaaa ttgtattttg tgatttgttt ataaattttt   4560
aatttttaa ataaataacc agctctattt tttatatcct tgacttcttc attccttcac   4620
tcctgtgact tattaatagt tttgtcttac ttttgaagta gatatatggt gctagcgtca   4680
atggtccagt tcggcacaaa tgtctttctg tcattggaaa attgatgtat ttcagcacag   4740
ctgagatgat ccagtctttg ttgagtgtaa caaatatatc aaggtattta gaacttcaat   4800
tgggttgctg ttgctctatg ttctctgtag aaaacttatg cattgtcact ttgatgatat   4860
agtttcttag ctggtgtgtt agcatggaaa gatccacatg ttttggttcc tgccttgcaa   4920
atttcagaaa ttcttatgga aaagcttcct ggaattttct ctaaaatgtt tgtcagagaa   4980
ggtgtggttc atgcagttga ccaacttatt ttggctggaa atgcaactaa tatatctaca   5040
caaacatcat ctgctgagaa ggatactgat tctgtatctg gaacttcatc tcgctctaga   5100
cgctatcgcc tgcgcagtgg taattcaaat cccgatgcga accgttcgga tgatttgaag   5160
agtccagttc cagtaaatgt tggtttgcca ccaagttctg tggaaactcc aacaactaat   5220
tctagtatcc gtgcatccat tagctcagtt gctaatgctt ttaaagacaa gtactttcct   5280
tctgatcctg ggtctgttga agtgggtgtt agtgatgatc ttttgcatct gaaaaatcta   5340
tgctcgaagt tgaacactgg tgttgatgac caaagaagta aggccaaggg aaaagttgaa   5400
gcttctggat ttgatctgga tgatgattct actaacacag aagagtattt gattggggtg   5460
atatctgaca tgctaaagga acttggcaaa ggagatagtg tatctacttt tgaatttatc   5520
ggtagtggtg ttgttgaagc cttgctaaat tatttttctt gtgggtattt ctctaaagat   5580
cgaatatcag aaaccaatct ccccaagctt cgccaacagg cacttacaag gttcaagtca   5640
tttgttgctg ttgcattacc tttgagcatt gacaatgggg ctgttgctcc tatgactgtc   5700
ttggttcaga agcttcaaaa tgtgttgtcc tccttggagc gtttccctgt aatgctgagt   5760
aattcatctc ggtcatctag tggaagtgga cgtctctcct ctgggctaag tgcattatct   5820
cagcccataa aattacgttt ctgtcgagcc cagggtgaaa agtcacttaa ggattattca   5880
tccagtgtgg tactgattga tccgttagca agtctagcag ccatcgagga atttctatgg   5940
gctcgtgtcc agcgtggtga atctggtcta aagtctactg taggcactga aaattctgaa   6000
tctggaacaa ctcctgcagg ggctggtgtt tcatctcctt cctcttatat tccctccact   6060
gcctttcgtt attcaaccgg atccagatcc agatcatctg ttaatatagg agatacacct   6120
agaaaagaaa tatttcaaga caatggcacg agctcatcta agagcaaggg taaagctgta   6180
ttaaaacctg cgcaggagga agcacgggga ccccaaacaa ggaatgcagt gcgcagaaga   6240
gcagctctag ataaagacgc tcaaatgaaa cctgcaaatg gcgactcaac ttctgaggta   6300
tgttgctaaa ttttgggaat gagtcataat agttaaataa ttttaatcta aattggttta   6360
taatactgaa taatttaatc cttgttgtat tttgtttata cttatactta ttgtccttcc   6420
ctctttttgt tagataaaaa accattggtg tgacttcttc atctaatagt tagttgatga   6480
tggcttttat tttactgctt tagattaaaa tgatgctttt cagttgatgt gtttcctgta   6540
gcatcttaaa cttgagtcgt ggcttttatt gtttaagccg ttttttattg tttgacacta   6600
ttttccactg cctttatggg ataggatgaa gaattggata tatctcctgt tgaaattgat   6660
gaggctttgg tgattgaaga tgatgatatt tctgatgatg aggatgaaga ccgtgaagat   6720
gtatgtttct tcttcttctt cttcttcttc ttctaagatt tcatcttatg gttgttatta   6780
```

```
cttttattca catctcattt tgtgatctaa atggtaagat ctcacaatct agctgacaca   6840
ttcctttctg aatcacatgt aaaatcttaa atgagtttgt tgtgagattt aaagatcact   6900
gaactagtga gattgtgcaa tccaaaaatc tgtctaattt cgagttatgt ttgaagtatt   6960
ttcttttgtg gtcttctggt tgtgttatgt atgtgactaa ttatgacttg ttttggatgc   7020
tacaagtatg aaatttcaat tttaagtttg ctataatgtt atctactttt ttctttcata   7080
ttttctatgc atacataaac ctatataatt tgtttgctag gattttatga tctacatttt   7140
acgattttgc aaccttcttt caaactaggt agaatctcga tcttgacaaa attggttgct   7200
accaggattg aaaactatca tttaggtgct tccgttcttg gagttgagtt ttacctaata   7260
gaaatgttat tgttgtttcc aagaatggat gctaccgtta attgttgttt agattggata   7320
ctatgatttg gtttagctgt tttgttctag ctattgaatt ttatcaaata gaaatggtat   7380
ttattgtttc ttatattttt aataatcatt aattgttgat tccaagattg gatgatatcg   7440
tttgatttgg ctgcatccat gctattaatt gaatgttatc aaacagaaat gatattattt   7500
cactaaccat catctaatgc atcatcagct tgctttattt atttatttat tttatttttg   7560
tgcaggtacg gagggattat tatcttcctg tctacttgcc tgacgaagtg catgatgtga   7620
aattgggtga ctcagctgag gagagtactg ttgctcctgc aacaagtgat agccagacta   7680
atgcagcttc aggttctagc agcaaagcgg gtacagccag gggttgtgac tctgctgatt   7740
ttaggagtgg gtattcatct agctcaaggg gtgcaatgtc atttgctgct gctgctatgg   7800
ctggacttgg atatgctaat agcagaggtt tcaggggtgg cagagatagg catgggcgcc   7860
tgttgtttgg tagttctaat gatcctccaa agttgatttt tactgctggt gggaagcatc   7920
ttaataggaa tttgactata tatcaggcaa ttcaaagaca gctcatgcta gatgaagatg   7980
atgatgagag acttgctggc agtgaccgtg tatctagtga tggaagcagc ctgtggggtg   8040
atatttacac catcacttat caaagggcag aaaaccagcc agataaggca tccaatggtg   8100
gatcaagttc aaatacttca aaatctgcca aatctgggtc tgcattaaat tccagctcag   8160
aagctaaatt gcatcagaca tctgttctag acagtatatt gcagggagac ttgccatgtg   8220
atctagagaa atctaatcct acctacaata ttttggcact cctgcgtgtg ctggagggtt   8280
tgaaccagct tgcgcctcat ttgaggaccc aaatggtttc tgatagcttc gccaagggaa   8340
aaatcttgga tttagatgag ctaggtgtta caactggtgc tagggtgctt ccagaggaat   8400
ttgtgagtgg taagcttact ccaaaattgg ctaggcaaat acaagatgcc cttgcactat   8460
gcagtggtag tcttccctta tggtgttgcc agttgactaa agcatgccct ttcttgtttc   8520
cttttgacac ccgacgacag tacttttatt ctaccgcatt tgggttatct cgtgcattgt   8580
atcgacttca gcagcagcaa ggcgctgatg gtcatggatc aacaactgag agggaggtga   8640
gagttgggag attgcagcgc caaaaggttc gtgtctctcg aaatcgtgtc ttggattctg   8700
ctgcaaaagt tatggggatg tattctagcc aaaaagctgt acttgaagta gaatattttg   8760
gtgaagttgg gactggcctg ggtcccaccc ttgagtttta tacaattcta agtcatgatt   8820
tgcaacaagt tggattgcaa atgtggagat cttattcttc agaaaaacat caaatggaaa   8880
ttgatagaga tgaaaagaaa aagaaaagtg atggctctgg gcctaatttg gctggagatg   8940
gagaacttgt tgaagctcct ctggggttgt ttcctcggcc ttggcctaca aattctgatg   9000
catcagaggg tagccggttt tcaaaagtcg ttgagtattt ccggctgcta ggtcgtgtta   9060
tggctaaagc tcttcaagac ggacgacttt tggacctgcc attgtcagtg gcattttata   9120
```

-continued

```
agcttgttct cggccaagta tgttgtgcaa tattgatgtt ttaaccattt tcatttgtat   9180
tgttaatctg atggtcaatt tcttctagtc tatgtaccta accttcactt tgtggcagga   9240
tcttgatttg catgacattc tgtccattga tgctgagctt gggaagactt tgcaagagtt   9300
caatgccctt gtttgtcgga aacattatat agaatctatt ggtggtagct atacagatac   9360
aattgttaac ttgcattttc atggggtgcc aatcgaagat ctttgcttag attttacact   9420
ccctggttat cctgaataca ccttgaagcc aggagatgaa attgtatgga gttaaactct   9480
gagctagtct ttagatattg gttcttgtgt tacagaaatt tcctttaact tactctcaaa   9540
ttctcaggtt gatatcaaca atttggagga gtatatatcc ttggtggcag atgcaactgt   9600
caagactgga atcatgcggc aaatagaagc atttagagca gggtttaacc aggttctatg   9660
ctgttcttaa taattagtaa tttaacttta aacgtatgca ttgttggcgt ggagcatgtt   9720
attattctaa aacaaggtgt ttccctctcc cctttccatt ggaaaatagc ttttattgac   9780
attatcatcc ttgtctatgc atgctcctat acttaagtcc caccacatcc ctgagaattt   9840
gtttttaact gcacacaatg tagatccatg tagctgacac cacctagtgg gataagatta   9900
ttgtagttgt agattggaat tagtttacct gatgcatgac attaatttgt taacatgtca   9960
ttgaaatgct taagtgacat tctgtctcac taaaaattat ttggtgtttt actgagatct  10020
taaatatctt ctgtttatct ctaatgcttg aatattccac ttgggagctt atatatgctc  10080
ctgttctttt acttacattg gctcccaacc accaaccata ctttccctgc acaaaatgga  10140
aattgcaaga ttcagttatt ggatgttaaa ttttttacat tctgaaatct gaatatattg  10200
tttgtgaaat gggtgggtag ttatggttct ggtagactct cttgtggatg agaagaggat  10260
attgatgggg aaattagtta cttttggctc atttaattta gttgaaaact aaacatcact  10320
tgtatgcttg tgctgtttaa tacaggtttt tgacatctcg tctttacaaa tttttactcc  10380
tcaagaacta gataatttgc tttgcggctg cagggagttg tgggaggtat ttttgcccaa  10440
ttttattatt gcttttaata ttagttaaaa tattagaaca aggcattgaa attacaagtt  10500
tttttgttat ttatcttact gcagtctgag acacttgctg atcatataaa attcgaccat  10560
gggtacaatg caaagagccc tgccattatt aatgtatgct tttttcccct aattataagg  10620
aatattgtgt atgacggaaa attagagcta gttatatatg atgctgttct gttggatgct  10680
atttcagtta cttgaaatta tgggagggtt cacaccagag cagcaacgtg ccttctgtca  10740
atttgttact ggtgcaccta ggctgccacc tggagggctg gcagttctaa atccaaaact  10800
aacgattgtg aggaaggtat tcagaaatgg atttttgata acgtgatatt aggtttattc  10860
atcttgtact ttaataattc ttttccatat taatttcatg gttatatatg catgtttatt  10920
ttttgttatt tccattatat tcatgcctta ttttgggtct tggtgtagct ttcgtcaacc  10980
gcagttaata cttcatctaa tgggaatgga ccttcagaat cagcagatga tgacttgcct  11040
agtgtgatga catgtgctaa ttacctgaaa cttcctcctt actctaccaa ggtactgtga  11100
tatgacatac gagaaatgat ttttacgtca caatgtcttc ctacctttac ttacaccttg  11160
ttgggggaaa atgtgttttt ctaagtttct attgttttta ttctccagaa gggaaatggt  11220
gcaatgaaaa tggtgtccaa ataactgttg catcataaat ttattgatta tattatctct  11280
catgtccatg tttggttgga attaattcta gaaaaaattg cttgttttta taatatctca  11340
ttttgaaact agacaaaact aaacaattat ttctccaaaa ttcatacgta tgttcattac  11400
tctgatattg catcttttgg tattaatcta tgttcatttt ttaacaggaa attatgtaca  11460
agaagctact ctatgcaatc aacgagggcc ggggatcctt tgatttatca tgagtttctg  11520
```

```
aaactaacca accttaccct gcatgttaat agatggttca gggtttatag actttattct  11580
cgaggctcag ttatttattt attttggttg gatctgcttt gctcctcgtt tctcgcttct  11640
cgaataatag tctcattttc cgtgctcaat gcaaattgca aggttgtgga attgttcagg  11700
tgagtaactt gttacttttt ccccccgaac tggctgggag gttcttctca tattgttctc  11760
ttttatttct gacatactta caagaatttc tcccataaat tgcagttgaa tcgggtagcc  11820
acattttcga agtgtagggg actttacgga gctcttaatt taattttacc tgttagaact  11880
tgtaaataga atagcaatga tgaaattttg attttctttt ttctttttaa aaaatttcat  11940
tattctgttt gtaattccaa ttattggcaa ttagcatgta cgaaaaaatg gtaaagggaa  12000
aataaataat ttaaaatatt ttgctttata atctcgttat attacttagt tacttgtcat  12060
ttggagtttt attgtaaaat tttgtcgacc tcattcgctt atgttaagtg aatgacttca  12120
agcattatat tattgatttt cctacgtttg cagtttttat ttttatgcat taaactaaag  12180
tatgttgtta gaaacgtgac ttagatccgt ttgttccaat cttattattt tgaataaaaa  12240
aatggtctag cgttttaaaa aataagattt tgtttattgt ttttctaaaa gataaatctt  12300
acgagtaaca ttttgaataa aaaataaagt tgtgtaatac ctttttttca aaataatgat  12360
taaaaaggtg gatttatatt tatatattta ggttttgttt gaattcaaat tgtgtgatgc  12420
gtgatatact tggtaaatga ttaaaaagtg attgttacga ctcaaccagt ttaatttatc  12480
tagctggttt taaaagtaga atgcagatca aataaaaagt taaaaggctg acttaatttt  12540
tttattgtaa tttagtttgg taattattct tattttaaaa attgaattga gcattacact  12600
ttcttttata tcaattgaac attatactat gttgtaatgt agttattatt ttattaagag  12660
tttgtaacgt agttattatc agtgttttta taactacttt atatgaacta attgattttt  12720
ttattcatct atgatagtga ttgtgatttt tatactgtgt gaacttattt cattagttat  12780
caaattaaaa taattttaaa atttataaaa ctttttttaa aaaaaggtaa aaaaaaaaaa  12840
ctgttgaatt catcaatcaa atagtaagag attttgtttt atgaaattat atatattttt  12900
tgttagagac aattcttctt aactcagata ttatctcttg cattagttct ttttaaatgt  12960
ttaaagatgt atattgatga tttaaattta agatatttaa tagagataaa ataatctcat  13020
atcaattgat tcattcatat gggtaataag aatttgaatt agtttgattt aaattttact  13080
ttacattgac ttaaattaca cattattttt agggcaaaat gtgtttatcc ttttaaaaaa  13140
ttgaaattct tttttgaaat gtgtcacctt tgaatcttaa attaaatgct aacttgaaga  13200
tagaatgtgg gatatattta tattttcttt ccatctaata aaaaaagttg aatatattcc  13260
aaaattagag ggactaaaat aaagtgtttt taaaaataac taaaatagaa ctttaaaatt  13320
tttagttgga ctgcaaatat gttattagct ctaatatttt tttttgtcta aacataaatt  13380
aattgcacaa actcaaatca aaataattat ttaaaaaaat aatcagaata tccaatgacc  13440
caaaccgaat caactcattt attatctagt tggtttggtt taggttagac aaaaaaaatg  13500
aatttaaacc aattaaaatt aattaattca aatatttttt tctctcaaat acgaattaaa  13560
tcaacccata aacacccccct aacaacgcaa ataccgtggt aattatgtac tacgtgatta  13620
taaatttggg atgcttgcaa gttgcatgag aattgggatt aattatagtg ttggaagtga  13680
taaatttagt gttcatttag ttaaatatta aaattattct tttttattaa agtagacagt  13740
agacgtttca aattaaaatt tattgacata ttttaattat atttacctaa ttttgccaag  13800
tcattaattg gacaatggac attcatatgt tgatcgagtg attaaggatg aaaatattat  13860
```

```
tattactgat atgacaaagt taatggtaaa atcaagaaat attcttcaaa ctctagagcc  13920

aaatttctat accttccttt catgggagaa caacttcaac taagaacgtt cctcaaaata  13980

aaaataaaaa tcatttgaat aataataaga actagttatg aaaatattat ttatttaaaa  14040

atataaatac atcttcattc caaattatca tcgtcacatg atgaacataa tccatcaaaa  14100

ctgatgtgtc gtgaggtctg cctgaaaaac cctcagcatt aataactaca tcagcagc    14158


<210> SEQ ID NO 10
<211> LENGTH: 14158
<212> TYPE: DNA
<213> ORGANISM: Glycine max

<400> SEQUENCE: 10

aagtggtatc tcaggaatca ttctctgtaa agtttccgag tcttcctccg ccaatggttg     60

aatttcagga tcctatccaa gccaacaata atgtattagt gcaatactta aaaattgcat    120

taaaaatgtc aaaatttcaa agatttacca tcaattttat atttttttatt gctttttttgc    180

atatataata gtgtgattat acctatttta aatttttttt cttatgggta gtgaagttgc    240

taaagacaaa aaaaattgaa ttccaagatg acatgtaaga aaaggattat ttattataat    300

ttatgatctt aatttacaaa aacttgttag agagcattgc ttagcttgta aaaatgaata    360

aaacaaataa aatcagactc aaacatggat ctaaaggaaa gagaaaggtt tacaattggg    420

tggaatacaa aataagataa tgtgttaaga atcatgtttt gtttgtacta cgcaccttaa    480

catcagtggg ttgaacatat ataaagagaa aatagccaat aacgaaacca atagaaatcc    540

caattccaaa gccaaaaaaa ccaaatatgg tgccaaagaa acccatgtca gttcttaatt    600

ttgtttcaac ttgctctgag gacaatccca atctctttct ctctccttat gctacaagta    660

aaattatcat gcaaatgcgc cacttccgat gtacttgagc tctcctcgga tcaccattcc    720

tatgttcaaa ccaaaacgtg gaatgcgaac cattttgacc ctaaaaaaag actatttata    780

ccaaaaaaaa taaaaacaaa gtatggttat cactaaggat ttaacacaaa tgattatgtt    840

attcttatta attaaagtta ctaccacaac tttttttcgg aatgatacta tcacataatt    900

tgtttattca tgatattata tatttgagga aaagtcacat gatatttaat tattttatct    960

cttaattatg tactatgcga tttagttaat ctttgacttt cttgtttgat atccaatttt   1020

aaaagtcagt ttacatttca taatgaataa aatcaaaata agatatttaa aaaataaaac   1080

atgttactgt attattttaa catattttta aaataatttt aagttaaaaa atgatttaat   1140

attttaagaa aacaaaaata ctattaaaca tgtaaatcaa ttcacataaa attatttgag   1200

tttaattaat attctttaat tcgagattta tacatatgaa cacatgatta aacatctact   1260

atcataaata ctatcttaat acccgttata tttgtagaaa attatttact tgtttagatg   1320

aacgaaatat tttttttttc agagacgaat ggaagaatga gttaaaataa acaaattata   1380

taatttttat aaagaaaaaa atatatttaa aaattaaaca tgttactaca tcatttctaa   1440

caattttttt tatattttta tgttaaaaaa gatttaatat ttcagaaaaa aaacactgaa   1500

tcatgtaaaa aaattgacat gaaattgttt aagtttattc atcttttttc cttttcatca   1560

aaccaaataa taagtgagag aaggagtgga gagttagcaa tttggattat ttatattttg   1620

ttttttaaat aaaaaatcat atttaatatt tttgtgtcta ttttaattta tttatcttta   1680

atcaaacaat cttcattttc atcatatttt ttacctatta acttttgttt tctccccttt   1740

atttctcaca actaaaacaa acaaggagag attaaattaa attgataaat aaaagataca   1800

gtgttgctgc ttttgttgag gttgagaggg caagtattta atatataaaa aatgggtgat   1860
```

-continued

```
atgaaatgta ataattttca atgagctgaa aacgacgccc tgacgacctt cttccccatc   1920
ggcacgcaaa ccagacaata tctgcttgag tccgccagtc tggtgagaag agggcacaga   1980
accgcccata gccgtagcag gaagcaaatc atccaaacca gcaccaagtt tccgaagaag   2040
ccctcgaaag gtactggcag aaatcaaatt ctggtgcaga attccgacac cgccctcact   2100
atcattatca tcgtcgtcat ccccaacatc ttcagcctcc aagttcaacg ccaaggctcg   2160
ctcccgctcc gcatccctaa tcctaacatc atgttctttc tccttccctt tgtccgaatt   2220
gtccctatcg aaattcttgc cgcggcgatc acgtctggaa ccggaggatt cattggtggg   2280
gtccatggga gaaacggagt tgttgttgtt gttcctggcg gaacgagaac gtgtattagc   2340
agtagttgtg tttgggatgg aagaagaaga agaagaaaga cgagagcact tggcggaacg   2400
agaggcggtg gtggtggtgg tggacgagga tgatgaaggg gcagctgagg aagcctccgc   2460
ccgcttacga ctacgagttt ccatacaaaa cccagaatca cccttcaatt tgtctcacct   2520
atcctagatc gatcgattgg attaatccct tgcatctcag attaaatgta ttaaattaaa   2580
atcggcgaaa accctaaatc aaaggaaaat tcccaatata gtgtacagag agaggaggaa   2640
attgttgcat gaaaacccta aggtgagagg gagagggaat aaaaaaggaa caagaaagac   2700
agagatatat caaatacgcc ttatatacgt tgtttgcaca tacatccact cgtcactcta   2760
aaacactgag tcagaagtca caactcgctt gctccctcct tgaggcattg acgcatcttt   2820
gtgacatgct ctccattggc actgaagatt cattaagtac attttcggtt gattcatttg   2880
ttcctgtgct agtgggcttg cttaatcatg agagcaatcc cgatgtcatg cttcttgcgg   2940
ccagggcgct aacccattta tgtgatgtgc ttccttcatc ctgtgctgct gttgtgcatt   3000
atggtgcagt ctctatcttc tgtgcgaggc tgcttaccat agagtatatg gacttggctg   3060
agcaggttat tttctcactc aatctctttt atgcctttag ttattatgta tctggaattc   3120
tttttagaat tttgtcttac tttgaattct gatagatgtg attgttgatg tgagcagtct   3180
cttcaagcac taaagaagat ttctcaggag cacccaactg cctgtcttcg agctggagct   3240
ctgatggctg ttctttctta cttggacttc ttctcgacag gagttcaggt aactcatcaa   3300
tgaaatccta atatcaaagg gtgatgattc attttgcatt tgccaccctt gattggcaag   3360
cctatattga cacaatcatg tttcagcggg tggcattgtc tactgctgca aatatgtgca   3420
agaagcttcc tcctgatgca gctgactttg tgatggaagc tgttccactt ttgacaaacc   3480
tccttcagta ccacgactcc aaggtaaggc caaggccatg tttgcttgtc ataaaaatga   3540
aaactgcact ttccttgtca ttccttccct ttaaggaaat tttgtttatg taaatattga   3600
ttcctacaat gttgtcaatt atctatttga gtcttcataa tattcaatgt taatttttgt   3660
aggtcctgga acatgcctct gtttgtttga cacgaatagc taaagcgttt gcatcatctc   3720
cagacaaatt agatgaattg tgcaatcatg gactggtaac acaagctgcc tctctcattt   3780
ctaccagcgg ttctggaggt gggcaggctt ctctcagcac cccaacatat actgtaagtg   3840
caatctttgc cactaaatct gatattttta tcctttggtg ggttgttcat ttgacttcat   3900
tggtgcttgc agggtttgat ccgccttctt tccacatgtg caagtgggtc tcctcttgga   3960
gctaaaacgt tgcttctcca tggagctagt ggcatactta aagatatact atccggttcc   4020
ggtgtttctt ctaacacctc tgtttcgcct gcattgagta ggccagcgga tcaggtatga   4080
tgtgcttttg agttcttttg gtctattaga tgtagttggt atctctatag ttcatttgat   4140
agactgtgac attgatctca tcatttaaat ctcagaaaac ttttcagttc tctttttgtg   4200
```

-continued

```
aaagatgagt ttatcctaat tctcttttct aatatttaga tatttgagat tgtgaacctg   4260
gcaaatgaac ttctgcctcc attgcctcaa ggaaccattt ctcttcctgt cagctccaac   4320
ttgtttgtga aagagtctgt tgtgaaaaaa tctcctcctt ctgggaatcc cgggatacaa   4380
gaagacacaa atggaaatgt tcatgaaata tcagctcgtg caaaattatt aaatgataag   4440
cctgagttac ttaagcaatt tgggatggat ctcctcccag ttttaatgca ggttcaatgt   4500
ttaaatttac tcatcgttaa aatgctcaaa ttgtattttg tgatttgttt ataaattttt   4560
aattttttaa ataaataacc agctctattt tttatatcct tgacttcttc attccttcac   4620
tcctgtgact tattaatagt tttgtcttac ttttgaagta gatatatggt gctagcgtca   4680
atggtccagt tcggcacaaa tgtctttctg tcattggaaa attgatgtat ttcagcacag   4740
ctgagatgat ccagtctttg ttgagtgtaa caaatatatc aaggtattta gaacttcaat   4800
tgggttgctg ttgctctatg ttctctgtag aaaacttatg cattgtcact ttgatgatat   4860
agtttcttag ctggtgtgtt agcatggaaa gatccacatg ttttggttcc tgccttgcaa   4920
atttcagaaa ttcttatgga aaagcttcct ggaattttct ctaaaatgtt tgtcagagaa   4980
ggtgtggttc atgcagttga ccaacttatt ttggctggaa atgcaactaa tatatctaca   5040
caaacatcat ctgctgagaa ggatactgat tctgtatctg gaacttcatc tcgctctaga   5100
cgctatcgcc tgcgcagtgg taattcaaat cccgatgcga accgttcgga tgatttgaag   5160
agtccagttc cagtaaatgt tggtttgcca ccaagttctg tggaaactcc aacaactaat   5220
tctagtatcc gtgcatccat tagctcagtt gctaatgctt ttaaagacaa gtactttcct   5280
tctgatcctg ggtctgttga agtgggtgtt agtgatgatc ttttgcatct gaaaaatcta   5340
tgctcgaagt tgaacactgg tgttgatgac caaagaagta aggccaaggg aaaagttgaa   5400
gcttctggat ttgatctgga tgatgattct actaacacag aagagtattt gattggggtg   5460
atatctgaca tgctaaagga acttggcaaa ggagatagtg tatctacttt tgaatttatc   5520
ggtagtggtg ttgttgaagc cttgctaaat tatttttctt gtgggtattt ctctaaagat   5580
cgaatatcag aaaccaatct ccccaagctt cgccaacagg cacttacaag gttcaagtca   5640
tttgttgctg ttgcattacc tttgagcatt gacaatgggg ctgttgctcc tatgactgtc   5700
ttggttcaga agcttcaaaa tgtgttgtcc tccttggagc gtttccctgt aatgctgagt   5760
aattcatctc ggtcatctag tggaagtgga cgtctctcct ctgggctaag tgcattatct   5820
cagcccataa aattacgttt ctgtcgagcc cagggtgaaa agtcacttaa ggattattca   5880
tccagtgtgg tactgattga tccgttagca agtctagcag ccatcgagga atttctatgg   5940
gctcgtgtcc agcgtggtga atctggtcta aagtctactg taggcactga aaattctgaa   6000
tctggaacaa ctcctgcagg ggctggtgtt tcatctcctt cctcttatat tccctccact   6060
gcctttcgtt attcaaccgg atccagatcc agatcatctg ttaatatagg agatacacct   6120
agaaaagaaa tatttcaaga caatggcacg agctcatcta agagcaaggg taaagctgta   6180
ttaaaacctg cgcaggagga agcacgggga ccccaaacaa ggaatgcagt gcgcagaaga   6240
gcagctctag ataaagacgc tcaaatgaaa cctgcaaatg gcgactcaac ttctgaggta   6300
tgttgctaaa ttttgggaat gagtcataat agttaaataa ttttaatcta aattggttta   6360
taatactgaa taatttaatc cttgttgtat tttgtttata cttatactta ttgtccttcc   6420
ctctttttgt tagataaaaa accattggtg tgacttcttc atctaatagt tagttgatga   6480
tggcttttat tttactgctt tagattaaaa tgatgctttt cagttgatgt gtttcctgta   6540
gcatcttaaa cttgagtcgt ggcttttatt gtttaagccg ttttttattg tttgacacta   6600
```

```
ttttccactg cctttatggg ataggatgaa gaattggata tatctcctgt tgaaattgat   6660
gaggctttgg tgattgaaga tgatgatatt tctgatgatg aggatgaaga ccgtgaagat   6720
gtatgtttct tcttcttctt cttcttcttc ttctaagatt tcatcttatg gttgttatta   6780
cttttattca catctcattt tgtgatctaa atggtaagat ctcacaatct agctgacaca   6840
ttcctttctg aatcacatgt aaaatcttaa atgagtttgt tgtgagattt aaagatcact   6900
gaactagtga gattgtgcaa tccaaaaatc tgtctaattt cgagttatgt ttgaagtatt   6960
ttcttttgtg gtcttctggt tgtgttatgt atgtgactaa ttatgacttg ttttggatgc   7020
tacaagtatg aaatttcaat tttaagtttg ctataatgtt atctactttt ttctttcata   7080
ttttctatgc atacataaac ctatataatt tgtttgctag gattttatga tctacatttt   7140
acgattttgc aaccttcttt caaactaggt agaatctcga tcttgacaaa attggttgct   7200
accaggattg aaaactatca tttaggtgct tccgttcttg gagttgagtt ttacctaata   7260
gaaatgttat tgttgtttcc aagaatggat gctaccgtta attgttgttt agattggata   7320
ctatgatttg gtttagctgt tttgttctag ctattgaatt ttatcaaata gaaatggtat   7380
ttattgtttc ttatattttt aataatcatt aattgttgat tccaagattg gatgatatcg   7440
tttgatttgg ctgcatccat gctattaatt gaatgttatc aaacagaaat gatattattt   7500
cactaaccat catctaatgc atcatcagct tgctttattt atttatttat tttatttttg   7560
tgcaggtacg gagggattat tatcttcctg tctacttgcc tgacgaagtg catgatgtga   7620
aattgggtga ctcagctgag gagagtactg ttgctcctgc aacaagtgat agccagacta   7680
atgcagcttc aggttctagc agcaaagcgg gtacagccag gggttgtgac tctgctgatt   7740
ttaggagtgg gtattcatct agctcaaggg gtgcaatgtc atttgctgct gctgctatgg   7800
ctggacttgg atatgctaat agcagaggtt tcaggggtgg cagagatagg catgggcgcc   7860
tgttgtttgg tagttctaat gatcctccaa agttgatttt tactgctggt gggaagcatc   7920
ttaataggaa tttgactata tatcaggcaa ttcaaagaca gctcatgcta gatgaagatg   7980
atgatgagag acttgctggc agtgaccgtg tatctagtga tggaagcagc ctgtggggtg   8040
atatttacac catcacttat caaagggcag aaaaccagcc agataaggca tccaatggtg   8100
gatcaagttc aaatacttca aaatctgcca aatctgggtc tgcattaaat tccagctcag   8160
aagctaaatt gcatcagaca tctgttctag acagtatatt gcagggagac ttgccatgtg   8220
atctagagaa atctaatcct acctacaata ttttggcact cctgcgtgtg ctggagggtt   8280
tgaaccagct tgcgcctcat ttgaggaccc aaatggtttc tgatagcttc gccaagggaa   8340
aaatcttgga tttagatgag ctaggtgtta caactggtgc tagggtgctt ccagaggaat   8400
ttgtgagtgg taagcttact ccaaaattgg ctaggcaaat acaagatgcc cttgcactat   8460
gcagtggtag tcttccctta tggtgttgcc agttgactaa agcatgccct ttcttgtttc   8520
cttttgacac ccgacgacag tacttttatt ctaccgcatt tgggttatct cgtgcattgt   8580
atcgacttca gcagcagcaa ggcgctgatg gtcatggatc aacaactgag agggaggtga   8640
gagttgggag attgcagcgc caaaaggttc gtgtctctcg aaatcgtgtc ttggattctg   8700
ctgcaaaagt tatggggatg tattctagcc aaaaagctgt acttgaagta gaatattttg   8760
gtgaagttgg gactggcctg ggtcccaccc ttgagtttta tacaattcta agtcatgatt   8820
tgcaacaagt tggattgcaa atgtggagat cttattcttc agaaaaacat caaatggaaa   8880
ttgatagaga tgaaaagaaa aagaaaagtg atggctctgg gcctaatttg gctggagatg   8940
```

```
gagaacttgt tgaagctcct ctggggttgt ttcctcggcc ttggcctaca aattctgatg   9000
catcagaggg tagccggttt tcaaaagtcg ttgagtattt ccggctgcta ggtcgtgtta   9060
tggctaaagc tcttcaagac ggacgacttt tggacctgcc attgtcagtg gcattttata   9120
agcttgttct cggccaagta tgttgtgcaa tattgatgtt ttaaccattt tcatttgtat   9180
tgttaatctg atggtcaatt tcttctagtc tatgtaccta accttcactt tgtggcagga   9240
tcttgatttg catgacattc tgtccattga tgctgagctt gggaagactt tgcaagagtt   9300
caatgccctt gtttgtcgga aacattatat agaatctatt ggtggtagct atacagatac   9360
aattgttaac ttgcattttc atggggtgcc aatcgaagat ctttgcttag attttacact   9420
ccctggttat cctgaataca ccttgaagcc aggagatgaa attgtatgga gttaaactct   9480
gagctagtct ttagatattg gttcttgtgt tacagaaatt tcctttaact tactctcaaa   9540
ttctcaggtt gatatcaaca atttggagga gtatatatcc ttggtggcag atgcaactgt   9600
caagactgga atcatgcggc aaatagaagc atttagagca gggtttaacc aggttctatg   9660
ctgttcttaa taattagtaa tttaacttta aacgtatgca ttgttggcgt ggagcatgtt   9720
attattctaa aacaaggtgt ttccctctcc cctttccatt ggaaaatagc ttttattgac   9780
attatcatcc ttgtctatgc atgctcctat acttaagtcc caccacatcc ctgagaattt   9840
gtttttaact gcacacaatg tagatccatg tagctgacac cacctagtgg gataagatta   9900
ttgtagttgt agattggaat tagtttacct gatgcatgac attaatttgt taacatgtca   9960
ttgaaatgct taagtgacat tctgtctcac taaaaattat ttggtgtttt actgagatct  10020
taaatatctt ctgtttatct ctaatgcttg aatattccac ttgggagctt atatatgctc  10080
ctgttctttt acttacattg gctcccaacc accaaccata ctttccctgc acaaaatgga  10140
aattgcaaga ttcagttatt ggatgttaaa ttttttacat tctgaaatct gaatatattg  10200
tttgtgaaat gggtgggtag ttatggttct ggtagactct cttgtggatg agaagaggat  10260
attgatgggg aaattagtta cttttggctc atttaattta gttgaaaact aaacatcact  10320
tgtatgcttg tgctgtttaa tacaggtttt tgacatctcg tctttacaaa tttttactcc  10380
tcaagaacta gataatttgc tttgcggctg cagggagttg tgggaggtat ttttgcccaa  10440
ttttattatt gcttttaata ttagttaaaa tattagaaca aggcattgaa attacaagtt  10500
tttttgttat ttatcttact gcagtctgag acacttgctg atcatataaa attcgaccat  10560
gggtacaatg caaagagccc tgccattatt aatgtatgct tttttcccct aattataagg  10620
aatattgtgt atgacggaaa attagagcta gttatatatg atgctgttct gttggatgct  10680
atttcagtta cttgaaatta tgggagggtt cacaccagag cagcaacgtg ccttctgtca  10740
atttgttact ggtgcaccta ggctgccacc tggagggctg gcagttctaa atccaaaact  10800
aacgattgtg aggaaggtat tcagaaatgg atttttgata acgtgatatt aggtttattc  10860
atcttgtact ttaataattc ttttccatat taatttcatg gttatatatg catgtttatt  10920
ttttgttatt tccattatat tcatgcctta ttttgggtct tggtgtagct ttcgtcaacc  10980
gcagttaata cttcatctaa tgggaatgga ccttcagaat cagcagatga tgacttgcct  11040
agtgtgatga catgtgctaa ttacctgaaa cttcctcctt actctaccaa ggtactgtga  11100
tatgacatac gagaaatgat ttttacgtca caatgtcttc ctacctttac ttacaccttg  11160
ttgggggaaa atgtgttttt ctaagtttct attgttttta ttctccagaa gggaaatggt  11220
gcaatgaaaa tggtgtccaa ataactgttg catcataaat ttattgatta tattatctct  11280
catgtccatg tttggttgga attaattcta gaaaaaattg cttgttttta taatatctca  11340
```

```
ttttgaaact agacaaaact aaacaattat ttctccaaaa ttcatacgta tgttcattac  11400
tctgatattg catcttttgg tattaatcta tgttcatttt ttaacaggaa attatgtaca  11460
agaagctact ctatgcaatc aacgagggcc ggggatcctt tgatttatca tgagtttctg  11520
aaactaacca accttaccct gcatgttaat agatggttca gggtttatag actttattct  11580
cgaggctcag ttatttattt attttggttg gatctgcttt gctcctcgtt tctcgcttct  11640
cgaataatag tctcattttc cgtgctcaat gcaaattgca aggttgtgga attgttcagg  11700
tgagtaactt gttacttttt ccccccgaac tggctgggag gttcttctca tattgttctc  11760
ttttatttct gacatactta caagaatttc tcccataaat tgcagttgaa tcgggtagcc  11820
acattttcga agtgtagggg actttacgga gctcttaatt taattttacc tgttagaact  11880
tgtaaataga atagcaatga tgaaattttg attttctttt ttctttttaa aaaatttcat  11940
tattctgttt gtaattccaa ttattggcaa ttagcatgta cgaaaaaatg gtaaagggaa  12000
aataaataat ttaaaatatt ttgctttata atctcgttat attacttagt tacttgtcat  12060
ttggagtttt attgtaaaat tttgtcgacc tcattcgctt atgttaagtg aatgacttca  12120
agcattatat tattgatttt cctacgtttg cagtttttat ttttatgcat taaactaaag  12180
tatgttgtta gaaacgtgac ttagatccgt ttgttccaat cttattattt tgaataaaaa  12240
aatggtctag cgttttaaaa aataagattt tgtttattgt ttttctaaaa gataaatctt  12300
acgagtaaca ttttgaataa aaaataaagt tgtgtaatac cttttttca aaataatgat  12360
taaaaaggtg gatttatatt tatatattta ggttttgttt gaattcaaat tgtgtgatgc  12420
gtgatatact tggtaaatga ttaaaaagtg attgttacga ctcaaccagt ttaatttatc  12480
tagctggttt taaaagtaga atgcagatca aataaaaagt taaaaggctg acttaatttt  12540
tttattgtaa tttagtttgg taattattct tattttaaaa attgaattga gcattacact  12600
ttcttttata tcaattgaac attatactat gttgtaatgt agttattatt ttattaagag  12660
tttgtaacgt agttattatc agtgttttta taactacttt atatgaacta attgattttt  12720
ttattcatct atgatagtga ttgtgatttt tatactgtgt gaacttattt cattagttat  12780
caaattaaaa taattttaaa atttataaaa cttttttttaa aaaaaggtaa aaaaaaaaaa  12840
ctgttgaatt catcaatcaa atagtaagag attttgtttt atgaaattat atatattttt  12900
tgttagagac aattcttctt aactcagata ttatctcttg cattagttct ttttaaatgt  12960
ttaaagatgt atattgatga tttaaattta agatatttaa tagagataaa ataatctcat  13020
atcaattgat tcattcatat gggtaataag aatttgaatt agtttgattt aaattttact  13080
ttacattgac ttaaattaca cattattttt agggcaaaat gtgtttatcc ttttaaaaaa  13140
ttgaaattct tttttgaaat gtgtcacctt tgaatcttaa attaaatgct aacttgaaga  13200
tagaatgtgg gatatattta tattttcttt ccatctaata aaaaaagttg aatatattcc  13260
aaaattagag ggactaaaat aaagtgtttt taaaaataac taaaatagaa ctttaaaatt  13320
tttagttgga ctgcaaatat gttattagct ctaatatttt tttttgtcta aacataaatt  13380
aattgcacaa actcaaatca aaataattat ttaaaaaaat aatcagaata tccaatgacc  13440
caaaccgaat caactcattt attatctagt tggtttggtt taggttagac aaaaaaaatg  13500
aatttaaacc aattaaaatt aattaattca aatatttttt tctctcaaat acgaattaaa  13560
tcaacccata aacacccccct aacaacgcaa ataccgtggt aattatgtac tacgtgatta  13620
taaatttggg atgcttgcaa gttgcatgag aattgggatt aattatagtg ttggaagtga  13680
```

```
taaatttagt gttcatttag ttaaatatta aaattattct tttttattaa agtagacagt  13740

agacgtttca aattaaaatt tattgacata ttttaattat atttacctaa ttttgccaag  13800

tcattaattg gacaatggac attcatatgt tgatcgagtg attaaggatg aaaatattat  13860

tattactgat atgacaaagt taatggtaaa atcaagaaat attcttcaaa ctctagagcc  13920

aaatttctat accttccttt catgggagaa caacttcaac taagaacgtt cctcaaaata  13980

aaaataaaaa tcatttgaat aataataaga actagttatg aaaatattat ttatttaaaa  14040

atataaatac atcttcattc caaattatca tcgtcacatg atgaacataa tccatcaaaa  14100

ctgatgtgtc gtgaggtctg cctgaaaaac cctcagcatt aataactaca tcagcagc    14158


<210> SEQ ID NO 11
<211> LENGTH: 20
<212> TYPE: DNA
<213> ORGANISM: Artificial Sequence
<220> FEATURE:
<223> OTHER INFORMATION: Synthetic

<400> SEQUENCE: 11

ggaagaaggt cgtcaggttg                                                 20


<210> SEQ ID NO 12
<211> LENGTH: 20
<212> TYPE: DNA
<213> ORGANISM: Artificial Sequence
<220> FEATURE:
<223> OTHER INFORMATION: Synthetic

<400> SEQUENCE: 12

gcatagaacg gtgccaatca                                                 20


<210> SEQ ID NO 13
<211> LENGTH: 20
<212> TYPE: DNA
<213> ORGANISM: Artificial Sequence
<220> FEATURE:
<223> OTHER INFORMATION: Synthetic

<400> SEQUENCE: 13

gaagataaat ctgcaaacgt                                                 20


<210> SEQ ID NO 14
<211> LENGTH: 20
<212> TYPE: DNA
<213> ORGANISM: Artificial Sequence
<220> FEATURE:
<223> OTHER INFORMATION: Synthetic

<400> SEQUENCE: 14

ggagctgaaa acgacgcgga                                                 20


<210> SEQ ID NO 15
<211> LENGTH: 20
<212> TYPE: DNA
<213> ORGANISM: Artificial Sequence
<220> FEATURE:
<223> OTHER INFORMATION: Synthetic

<400> SEQUENCE: 15

gcggtatttg cgttgttagg                                                 20


<210> SEQ ID NO 16
<211> LENGTH: 504
```

```
<212> TYPE: PRT
<213> ORGANISM: Glycine max

<400> SEQUENCE: 16

Met Ala Ile Ser Asp Glu Pro Glu Ser Val Ala Thr Ala Leu Asn His
1               5                   10                  15

Ser Ser Leu Arg Arg Arg Pro Ser Ala Thr Ser Thr Ala Gly Leu Phe
            20                  25                  30

Asn Ser Pro Glu Thr Thr Thr Asp Ser Ser Gly Asp Asp Leu Ala Lys
        35                  40                  45

Asp Ser Gly Ser Asp Asp Ser Ile Asn Asn Asp Asp Ala Ala Val Asn
    50                  55                  60

Ser Gln Gln Gln Asn Glu Lys Gln Asp Thr Asp Phe Ser Val Leu Lys
65                  70                  75                  80

Phe Ala Tyr Arg Pro Ser Val Pro Ala His Arg Lys Val Lys Glu Ser
                85                  90                  95

Pro Leu Ser Ser Asp Thr Ile Phe Arg Gln Ser His Ala Gly Leu Phe
            100                 105                 110

Asn Leu Cys Ile Val Val Leu Val Ala Val Asn Ser Arg Leu Ile Ile
        115                 120                 125

Glu Asn Leu Met Lys Tyr Gly Trp Leu Ile Lys Ser Gly Phe Trp Phe
    130                 135                 140

Ser Ala Lys Ser Leu Arg Asp Trp Pro Leu Phe Met Cys Cys Leu Ser
145                 150                 155                 160

Leu Val Val Phe Pro Phe Ala Ala Phe Met Val Glu Lys Leu Ala Gln
                165                 170                 175

Arg Lys Cys Ile Pro Glu Pro Val Val Val Val Leu His Ile Ile Ile
            180                 185                 190

Thr Ser Thr Ser Leu Phe Tyr Pro Val Leu Val Ile Leu Lys Cys Asp
        195                 200                 205

Ser Ala Phe Val Ser Gly Val Thr Leu Met Leu Phe Ser Cys Val Val
    210                 215                 220

Trp Leu Lys Leu Val Ser Phe Ala His Thr Asn Tyr Asp Met Arg Ala
225                 230                 235                 240

Leu Thr Lys Leu Val Glu Lys Gly Glu Ala Leu Leu Asp Thr Leu Asn
                245                 250                 255

Met Glu Tyr Pro Tyr Asn Val Thr Phe Lys Ser Leu Ala Tyr Phe Leu
            260                 265                 270

Leu Ala Pro Thr Leu Cys Tyr Gln Pro Ser Tyr Pro Arg Thr Pro Tyr
        275                 280                 285

Ile Arg Lys Gly Trp Leu Phe Arg Gln Leu Val Lys Leu Ile Val Phe
    290                 295                 300

Thr Gly Val Met Gly Phe Ile Ile Glu Gln Tyr Ile Asn Pro Ile Val
305                 310                 315                 320

Gln Asn Ser Gln His Pro Leu Lys Gly Asn Leu Leu Tyr Ala Thr Glu
                325                 330                 335

Arg Val Leu Lys Leu Ser Val Pro Asn Leu Tyr Val Trp Leu Cys Met
            340                 345                 350

Phe Tyr Cys Phe Phe His Leu Trp Leu Asn Ile Val Ala Glu Leu Leu
        355                 360                 365

Arg Phe Gly Asp Arg Glu Phe Tyr Lys Asp Trp Trp Asn Ala Lys Thr
    370                 375                 380

Val Glu Asp Tyr Trp Arg Met Trp Asn Met Pro Val His Lys Trp Met
385                 390                 395                 400
```

-continued

```
Ile Arg His Leu Tyr Phe Pro Cys Leu Arg His Gly Leu Pro Lys Ala
                405                 410                 415

Ala Ala Leu Leu Ile Ser Phe Leu Val Ser Ala Leu Phe His Glu Leu
            420                 425                 430

Cys Ile Ala Val Pro Cys His Met Phe Lys Leu Trp Ala Phe Gly Gly
        435                 440                 445

Ile Met Phe Gln Val Pro Leu Val Leu Ile Thr Asn Tyr Leu Gln Asn
    450                 455                 460

Lys Phe Lys Asn Ser Met Val Gly Asn Met Ile Phe Trp Phe Ile Phe
465                 470                 475                 480

Ser Ile Val Gly Gln Pro Met Cys Val Leu Leu Tyr Tyr His Asp Leu
                485                 490                 495

Met Asn Arg Lys Gly Lys Leu Asp
            500
```